US012173308B2

(12) United States Patent
Kyostio-Moore

(10) Patent No.: US 12,173,308 B2
(45) Date of Patent: Dec. 24, 2024

(54) HUMAN PAH EXPRESSION CASSETTE FOR TREATMENT OF PKU BY LIVER-DIRECTED GENE REPLACEMENT THERAPY

(71) Applicant: Genzyme Corporation, Cambridge, MA (US)

(72) Inventor: Sirkka R. M. Kyostio-Moore, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 289 days.

(21) Appl. No.: 17/490,416

(22) Filed: Sep. 30, 2021

(65) Prior Publication Data

US 2022/0112520 A1    Apr. 14, 2022

Related U.S. Application Data

(60) Provisional application No. 63/121,797, filed on Dec. 4, 2020, provisional application No. 63/086,537, filed on Oct. 1, 2020.

(51) Int. Cl.
| | | |
|---|---|---|
| *A61P 1/16* | (2006.01) | |
| *A61K 31/519* | (2006.01) | |
| *A61K 38/44* | (2006.01) | |
| *A61K 38/51* | (2006.01) | |
| *A61P 3/00* | (2006.01) | |
| *C12N 9/02* | (2006.01) | |
| *C12N 15/86* | (2006.01) | |

(52) U.S. Cl.
CPC ............ *C12N 15/86* (2013.01); *A61K 31/519* (2013.01); *A61K 38/44* (2013.01); *A61K 38/51* (2013.01); *A61P 1/16* (2018.01); *A61P 3/00* (2018.01); *C12N 9/0071* (2013.01); *C12Y 114/16001* (2013.01); *C12Y 403/01024* (2013.01); *C12N 2750/14123* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 6,566,118 B1 | 5/2003 | Atkinson et al. | |
| 6,596,535 B1 | 7/2003 | Carter | |
| 6,723,551 B2 | 4/2004 | Kotin et al. | |
| 6,989,264 B2 | 1/2006 | Atkinson et al. | |
| 7,125,717 B2 | 10/2006 | Carter | |
| 7,765,583 B2 | 7/2010 | Kalonji et al. | |
| 7,785,888 B2 | 8/2010 | Carter | |
| 7,790,154 B2 | 9/2010 | Samulski et al. | |
| 7,846,729 B2 | 12/2010 | Carter | |
| 8,093,054 B2 | 1/2012 | Carter | |
| 8,137,948 B2 | 3/2012 | Guang et al. | |
| 8,283,151 B2 | 10/2012 | Schmidt et al. | |
| 8,361,457 B2 | 1/2013 | Samulski et al. | |
| 10,610,606 B2 | 4/2020 | Seymour et al. | |
| 11,377,642 B2 | 7/2022 | Derosa et al. | |
| 11,382,941 B2* | 7/2022 | Wilson | A61P 3/00 |
| 2004/0224411 A1 | 11/2004 | Reed et al. | |
| 2012/0066783 A1 | 3/2012 | Mark et al. | |
| 2012/0087862 A1* | 4/2012 | Hood | G01N 33/6845 424/9.1 |
| 2013/0323226 A1 | 12/2013 | Wilson et al. | |
| 2017/0356009 A1* | 12/2017 | Lu | C12N 15/86 |
| 2019/0376081 A1 | 12/2019 | Berguig et al. | |
| 2020/0318081 A1 | 10/2020 | Lahusen et al. | |
| 2021/0040456 A1 | 2/2021 | Rajendran et al. | |
| 2021/0130794 A1 | 5/2021 | Seymour et al. | |
| 2021/0246467 A1* | 8/2021 | Xiao | A61K 48/00 |

FOREIGN PATENT DOCUMENTS

| | | |
|---|---|---|
| EP | 3938515 A2 | 1/2022 |
| WO | WO 2003/042397 A2 | 5/2003 |
| WO | WO 2010/148143 A1 | 12/2010 |
| WO | WO 2013/029030 A1 | 2/2013 |
| WO | WO 2019/241324 A1 | 12/2019 |
| WO | WO 2020/077250 A1 | 4/2020 |
| WO | WO 2021/144649 A2 | 7/2021 |
| WO | WO 2021/146260 A1 | 7/2021 |
| WO | WO 2021/202943 A1 | 10/2021 |
| WO | WO 2021/243364 A1 | 12/2021 |
| WO | WO 2021/247507 A1 | 12/2021 |
| WO | WO 2021/252952 A1 | 12/2021 |
| WO | WO 2022/061000 A1 | 3/2022 |

OTHER PUBLICATIONS

Grisch-Chan, H.M., Schwank, G., Harding, C.O. and Thony, B., 2019. State-of-the-art 2019 on gene therapy for phenylketonuria. Human gene therapy, 30(10), pp. 1274-1283. (Year: 2019).*
Morgenstern, P.F., Marongiu, R., Musatov, S.A. and Kaplitt, M.G., 2011. Adeno-associated viral gene delivery in neurodegenerative disease. Neurodegeneration: Methods and Protocols, pp. 443-455. (Year: 2011).*
Rosas, L.E., Grieves, J.L., Zaraspe, K., La Perle, K.M., Fu, H. and McCarty, D.M., 2012. Patterns of scAAV vector insertion associated with oncogenic events in a mouse model for genotoxicity. Molecular Therapy, 20(11), pp. 2098-2110. (Year: 2012).*

(Continued)

*Primary Examiner* — Nancy J Leith
*Assistant Examiner* — Khaleda B Hasan
(74) *Attorney, Agent, or Firm* — LATHROP GPM LLP; James H. Velema, Esq.; Michael J. Spellberg, Esq.

(57) ABSTRACT

Provided herein are expression cassettes for expressing a transgene in a liver cell, wherein the transgene encodes a PAH polypeptide. Also provided are methods to treat phenylketonuria (PKU) and/or to reduce levels of phenylalanine in an individual in need thereof. Further provided herein are vectors (e.g., rAAV vectors), viral particles, pharmaceutical compositions and kits for expressing a PAH polypeptide in an individual in need thereof.

37 Claims, 34 Drawing Sheets

Specification includes a Sequence Listing.

(56) References Cited

OTHER PUBLICATIONS

Anderson, "White matter pathology in phenylketonuria", Mol. Gen. Metab., 2010, 99: S3-S9.
Blau, "Alternative therapies to address the unmet medical needs of patients with phenylketonuria", Expert Opin. Pharmaco. Ther., 2015, 16(6): 791-800.
Charron, "Evidence for dominant negative interference in the Pahenu2 mouse model of PKU", Mol. Ther., 2004, 9: S334.
Chatterjee et al., "AAV and Hematopoietic Stem Cells: The Potential of AAVHSCs in Genetic Medicines", Human Gene Ther., 2020, 31(9-10): 542-552.
Chuah et al., "Liver specific transcriptional modules identified by genome wide in silico analysis enable efficient gene therapy in mice and nonhuman primates", Mol. Ther., 2014, 22(9): 1605-1613.
Clark et al., "Highly Purified Recombinant Adeno-Associated Virus Vectors Are Biologically Active and Free of Detectable Helper and Wild-Type Viruses", Hum. Gene Ther., Apr. 1999, 10: 1031-1039.
Conway et al., "Recombinant adeno-associated virus type 2 replication and packaging is entirely supported by a herpes simplex virus type 1 amplicon expressing Rep and Cap," J. Virology, 1997, 71(11): 8780-8789.
Davidson et al., "Recombinant adeno-associated virus type 2, 4, and 5vectors: Transduction of variant cell types and regions in the mammalian central nervous system", PNAS, 2000, 97(7): 3428-3432.
Deacon, "Assessing nest building in mice", Nature Protocols, 2006, 1: 1117-1119.
Ding et al., "Correction of Murine PKU Following AAV-mediated Intramuscular Expression of a Complete Phenylalanine Hydroxylating System", Mol. Ther., Apr. 2008, 16(4): 673-681.
Ding, "Administration route and gender independent long term therapeutic correction of phenylketonuria in a mouse model by recombinant adeno associated virus 8 pseudo typed vector mediated gene transfer", Gene Therapy, 2006, 13: 587-593.
Enns et al., "Suboptimal outcomes in patients with PKU treated early with diet alone: revisiting the evidence", Mol. Genet. Metab., 2010, 101: 99-109.
Erlandsen et al., "Structural studies on phenylalanine hydroxylase and implications towards understanding and treating phenylketonuria", Pediatrics, Dec. 2003, 112(6): 1557-1565.
Ferreira et al., "Immune Responses to Intramuscular Administration of Alipogene Tiparvovec (AAV1-LPLS447X) in a Phase II Clinical Trial of Lipoprotein Lipase Deficiency Gene Therapy", Hum. Gene Ther., Mar. 2014, 25: 180-188.
Fisher et al., "Transduction with recombinant adeno-associated virus for gene therapy is limited by leading-strand synthesis", J. Virol., Jan. 1996, 70(1): 520-532.
Gao et al., "Adeno-associated viruses undergo substantial evolution in primates during natural infections", PNAS, May 2003, 100(10): 6081-6086.
Gao et al., "Clades of Adeno-Associated Viruses Are Widely Disseminated in Human Tissues", J. Virol., Jun. 2004, 78(12): 6381-6388.
Gao et al., "Novel adeno-associated viruses from rhesus monkeys as vectors for human gene therapy", PNAS, Sep. 2002, 99(18): 11854-11856.
Garcia, "Treatment adherence during childhood in individuals with phenylketonuria: Early signs of treatment discontinuation", Mol. Gen. Metab. Reports, Jun. 2017, 11: 54-58.
Grimm et al., "In Vitro and In Vivo Gene Therapy Vector Evolution via Multispecies Interbreeding and Retargeting of Adeno-Associated Viruses", J. Virol., Jun. 2008, 82(12): 5887-5911.
Groth et al., "A phage integrase directs efficient site-specific integration in human cells", Proc. Natl. Acad. Sci., May 2000, 97: 5995-6000.
Hamman, "Hepatocytes from wildtype or heterozygous donors are equally effective in achieving successful therapeutic liver repopulation in murine phenylketonuria (PKU)", Mol. Genet. Metab., 2011, 104: 235-240.
Harding et al., "Complete correction of hyperphenylalaninemia following liver-directed, recombinant AAV2/8 vector mediated gene therapy in murine phenylketonuria", Gene Therapy, Mar. 2006, 13(5): 457-462.
Heintz et al., "Quantification of phenylalanine hydroxylase activity by isotope-dilution liquid chromatography-electrospray ionization tandem mass spectrometry", Mol Genet Metab., Apr. 2012, 105(4): 559-565.
Ho, "Phenylketonuria: translating research into novel therapies", Transl. Pediatr., Apr. 2014, 3(2): 49-62.
International Search Report and Written Opinion for PCT International Patent Application No. PCT/US2021/052913, dated Mar. 3, 2022.
International Preliminary Report on Patentability for PCT International Patent Application No. PCT/US2021/052913, dated Mar. 28, 2023.
Jacobs et al., "Direct comparison of hepatocyte specific expression cassettes following adenoviral hydrodynamic gene transfer", Gene Ther, Feb. 2008, 15: 594-603.
Jiang et al., "Multiyear therapeutic benefit of AAV serotypes 2, 6, and 8 delivering factor VIII to hemophilia A mice and dogs", Blood, Mar. 2006, 108: 107-115.
Kankaanpaa et al., "Oxalic acid stabilizes dopamine, serotonin, and their metabolites in automated liquid chromatography with electrochemical detection", J. Chromatogr. B. Biomed. Sci. Appl, Apr. 2001, 753(2): 413-419.
Kim, "Mammalian cell transfection: the present and the future", Anal. Bioanal. Chem., 2010, 397: 3173-3178.
Kochhar, "Clinical therapeutics for phenylketonuria", Drug Deliv. Transl. Res., 2012, 2: 223-237.
Kotin, "Large-scale recombinant adeno-associated virus production", Hum Mol Genet., 2011, 20(R1): R2-R6.
Kotin, "Prospects for the Use of Adeno-Associated Virus as a Vector for Human Gene Therapy", Hum. Gene Ther., 1994, 5(7): 793-801.
Kramer, "In vitro and in vivo comparative study of liver specific promoters", Mol. Ther., Mar. 2003, 7(3): 375-385.
Krysan et al., "Isolation of Human Sequences That Replicate Autonomously in Human Cells", Mol. Cell Biol., Mar. 1989, 9(3): 1026-1033.
Kyostio-Moore, "The impact of minimally oversized adeno associated viral vectors encoding human Factor VIII on vector potency in vivo", Mol. Ther. Methods Clin. Dev., 2016, 3: 16006, 12 pages.
Ledley, "Mouse phenylalanine hydroxylase. Homology and divergence from human phenylalanine hydroxylase", Biochem J, 1990, 267: 399-406.
Levitt et al., "Definition of an efficient synthetic poly(A) site", Genes Develop., 1989, 3: 1019-1025.
Lisowski et al., "Selection and evaluation of clinically relevant AAV variants in a xenograft liver model", Nature, Feb. 2014, 506(7488): 382-386.
Liu et al., "Production of recombinant adeno-associated virus vectors using a packaging cell line and a hybrid recombinant adenovirus", Gene Ther., Feb. 1999, 6: 293-299.
Longo et al., "Single dose, subcutaneous recombinant phenylalanine ammonia lyase conjugated with polyethylene glycol in adult patients with phenylketonuria: an open label, multicenter, phase 1 dose escalation trial", Lancet, 2014, 384: 37-44.
Martin et al., "Generation and Characterization of Adeno-Associated Virus Producer Cell Lines for Research and Preclinical Vector Production", Human Gene Therapy Methods, Jul. 2013, 24: 253-269.
McDonald, "Characterization of mutations at the mouse phenylalanine hydroxylase locus", Genomics, 1996, 39: 402-405.
McEachern et al., "AAV8-mediated expression of glucocerebrosidase ameliorates the storage pathology in the visceral organs of a mouse model of Gaucher disease", J. Gene Med., 2006, 8(6): 719-729.
McLaughlin et al., "Adeno-Associated Virus General Transduction Vectors: Analysis of Proviral Structures", J. Virol., 1988, 62(6): 1963-1973.
Miyazaki, J. et al., "Expression vector system based on the chicken B-actin promoter directs efficient production of interleukin-5", Gene, 1989, vol. 79, 2, 269-277.

(56) References Cited

OTHER PUBLICATIONS

Mochizuki et al., "Long-term correction of hyperphenylalanemia by AAV-mediated gene transfer leads to behavioral recovery in phenylketonuria mice", Gene Ther., 2004, 11: 1081-1086.
Nakamura et al., "Codon usage tabulated from international DNA sequence databases: status for the year 2000", Nucleic Acids Res., 2000, 28(1); 292.
Nambiar et al., "Characteristics of minimally oversized adeno associated virus vectors encoding human Factor VIII generated using producer cell lines and triple transfection", Hum Gene Ther. Methods, 2017, 28: 23-38.
Nathwani et al., "Adeno associated virus vector mediated gene transfer in hemophilia B", Genet Metab., NEJM, 2011, 365: 2357-2365.
NCBI GenBank, "*Homo sapiens* phenylalanine hydroxylase (PAH), transcript variant 1, mRNA", Database accession No. NM_000277.3, Aug. 27, 2023.
NCBI GenBank, "phenylalanine hydroxylase [*Homo sapiens*]", Database accession No. AAA60082.1, Jan. 7, 1995.
O'Gorman et al., "Recombinase-Mediated Gene Activation and Site-Specific Integration in Mammalian Cells", Science, 1991, 251(4999): 1351-1355.
Oh et al., "Long-term enzymatic and phenotypic correction in the phenylketonuria mouse model by adeno associated virus vector-mediated gene transfer", Pediatric Research, Aug. 2004, 56: 278-284.
Park et al., "Tissue-specific activation of mitogen-activated kinases for expression of transthyretin by phenylalanine and its metabolite, phenyl pyruvic acid", Exp. Mol. Med., 2010, 42: 105-115.
Passini et al., "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of-Glucuronidase-Deficient Mice", J. Virol., 2003, 77(12): 7034-7040.
Pechan et al., "Novel anti-VEGF chimeric molecules delivered by AAV vectors for inhibition of retinal neovascularization", Gene Ther., 2009, 16: 10-16.
Sabatino et al., "Efficacy and safety of long term prophylaxis in severe hemophilia A dogs following liver gene therapy using AAV vectors", Mol. Ther., Mar. 2011, 19(3): 442-449.
Sauer, "Site-specific DNA recombination in mammalian cells by the Cre recombinase of bacteriophage P1", Proc. Natl. Acad. Sci., Mar. 1988, 85: 5166-5170.
Singh et al., "CRISPR/Cas9 generated knockout mice lacking phenylalanine hydroxylase protein as a novel preclinical model for human phenylketonuria", Scientific Reports, 2021(11): 7254, 15 pages.
Smith et al., "Gene Transfer Properties and Structural Modeling of Human Stem Cell-derived AAV", Mol. Ther., 2014, 22(9): 1625-1634.
Thomas et al., "Strategies for successful long-term engagement of adults with phenylalanine hydroxylase deficiency returning to clinic", J Inborn Errors Metabolism & Screening, 5: 1-9, 2019.
Urabe et al., "Insect Cells as a Factory to Produce Adeno-Associated Virus Type 2 Vectors", Human Gene Therapy, 2002, 13(16): 1935-1943.
Veldwijk et al., "Development and Optimization of a Real-Time Quantitative PCR-Based Method for the Titration of AAV-2 Vector Stocks", Mol. Ther., 2002, 6(2): 272-278.
Viecelli et al., "Treatment of phenylketonuria using minicircle based naked DNA gene transfer to murine liver", Hepatology, Feb. 2014, 60: 1035-1043.
Waisbren et al., "Phenylalanine blood levels and clinical outcomes in phenylketonurea: a systemic literature review and meta analysis", Mol. Genet. Metab, 2007, 92: 63-70.
Walter et al., "how practical are recommendations for dietary control in phenylketonuria?", The Lancet, 2002, 360: 55-56.
Wang et al., "Rapid and highly efficient transduction by double-stranded adeno-associated virus vectors in vitro and in vivo", Gene Ther, Dec. 2003, 10: 2105-2111.
Winn et al., "Blood phenylalanine reduction corrects CNS dopamine and serotonin deficiencies and partially improves behavioral performance in adult phenylketonuric mice", Mol Gen Metabolism, 2018, 123: 6-20.
Wooddell et al., "Sustained liver specific transgene expression from the albumin promoter in mice following hydrodynamic plasmid DNA delivery", J Gene Med, 2008, vol. 10, pp. 551-563.
Xiao et al., "Gene transfer by adeno-associated virus vectors into the central nervous system", Exp. Neurobiol., 1997, 144(1): 113-124.
Xiao et al., "Production of High-Titer Recombinant Adeno-Associated Virus Vectors in the Absence of Helper Adenovirus", Journal of Virology, Mar. 1998, 72(3): 2224-2232.
Xie et al., "The atomic structure of adeno-associated virus (AAV-2), a vector for human gene therapy", Proc. Natl. Acad. Sci. USA, 2002, 99(16): 10405-10410.
Yagi et al., "Complete restoration of phenylalanine oxidation in phenylketonuria mouse by a self-complementary adeno associated virus vector", J Gene Med, 2011, vol. 13, pp. 114-122.
Yagi et al., "Recovery of neurogenic amines in phenylketonuria mice after liver targeted gene therapy", NeuroReport, 2012, 23: 30-34.
Yew et al., "Erythrocytes encapsulated with phenylalanine hydroxylase exhibit improved pharmacokinetics and lowered plasma phenylalanine levels in normal mice", Mol Gen Metab, 2013, vol. 109: 339-344.
Zhong et al., "Next generation of adeno-associated virus 2 vectors: Point mutations in tyrosines lead to high-efficiency transduction at lower doses", Proc. Natl. Acad. Sci. USA, 2008, 105(22): 7827-7832.

\* cited by examiner

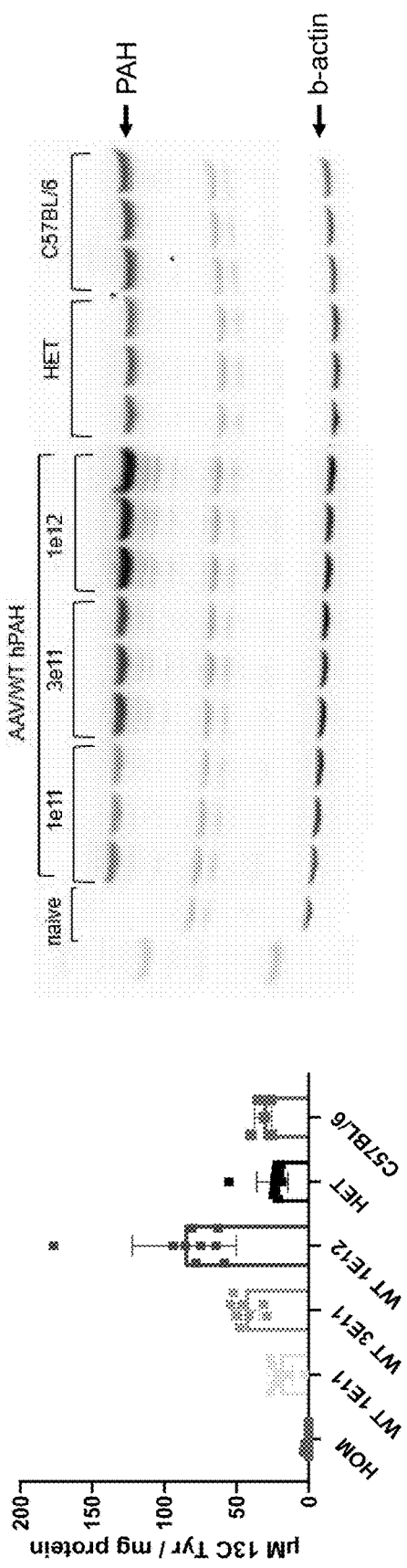
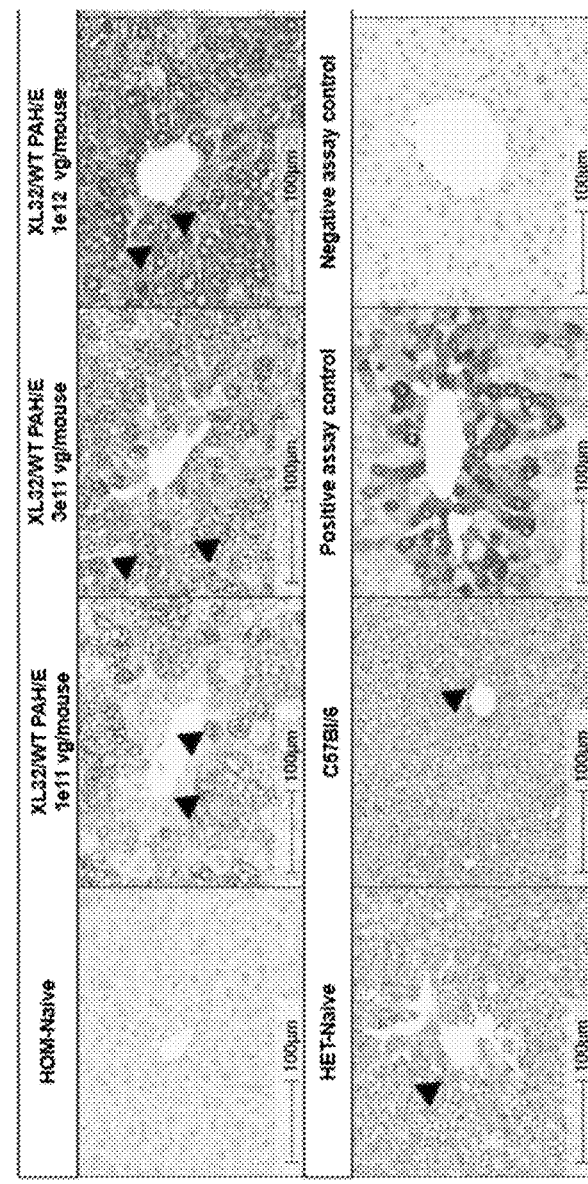
FIG. 8A
FIG. 8B
FIG. 8C

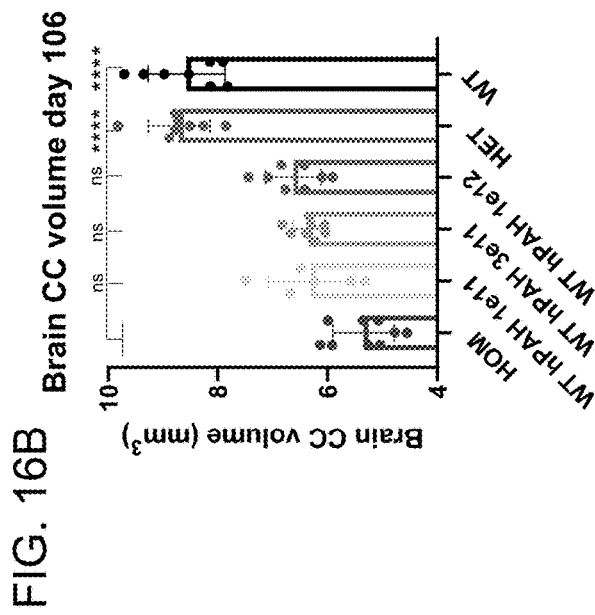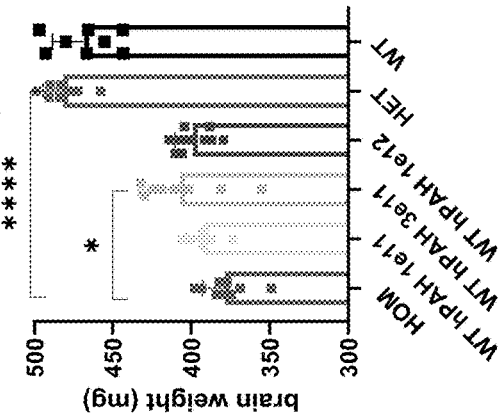
FIG. 16A  FIG. 16B  FIG. 16C  FIG. 16D

Score: 1  2  3  4  5

HUMAN PAH EXPRESSION CASSETTE FOR TREATMENT OF PKU BY LIVER-DIRECTED GENE REPLACEMENT THERAPY

CROSS-REFERENCE TO RELATED APPLICATIONS

This application claims the priority benefit of U.S. Provisional Application No. 63/086,537, filed Oct. 1, 2020, and U.S. Provisional Application No. 63/121,797, filed Dec. 4, 2020, the contents of each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792017800SEQLIST.TXT, date recorded: Sep. 22, 2021, size: 31,028 bytes).

FIELD OF THE INVENTION

The present disclosure relates to expression cassettes for expressing phenylalanine hydroxylase polypeptides. In some aspects, the disclosure relates to compositions and methods for treating phenylketonuria using gene therapy.

BACKGROUND

Phenylketonuria (PKU) is a genetic deficiency of liver enzyme phenylalanine hydroxylase (PAH) that catalyzes hydroxylation of phenylalanine (Phe) to tyrosine (Tyr). This disease is the most common inborn error of amino acid metabolism, with an overall incidence of 1:10-15,000 in North America, and it is detected by newborn screening programs in most developed countries. In the absence of any treatment, the severe form of PKU leads to highly elevated blood Phe levels that are neurotoxic and associated with intellectual disability (Kochhar 2012, Ho 2014, Blau 2015). The affected protein, PAH, is a multi-domain protein consisting of N-terminal regulatory (1-117), central catalytic (118-410) and C-terminal tetramerization domains (411-452) (Flydal 2013). To date over 560 disease-causing mutations have been mapped to each domain with the catalytic region being the most frequently affected site (Erlandsen 2003). The homo-multimeric enzyme is subject to complex regulation with phosphorylation and allosteric activation by substrate Phe binding to the N-terminal domain which fine-tunes PAH enzyme activity by altering various conformational and multimerization states of the enzyme (Knappskog 1996, Jaffe 2013, Arturo 2016).

The current treatment for PKU is a life-long dietary restriction of Phe using a low protein diet and liquid medical formula (Kochhar 2012, Ho 2014, Blau 2015). Although efficacious, the poor taste of the medical food and the severe limitations on food choices make adherence to the diet difficult and non-compliance increases steadily during childhood, and by late teens nearly 80% of patients have higher than recommended blood Phe levels (Waisbren 2007, Thomas 2017). There is also emerging evidence that despite good adherence to Phe-restricted diet, many patients experience deficiencies in various neurocognitive and neuropsychiatric functions as well as have a high incidence of attention deficit-hyperactivity disorder (ADHD). While the reasons for this are unclear, potential explanations include amino acid imbalances in brain, nutritional deficiencies in certain vitamins and trace elements as well as fluctuations in blood Phe levels normally maintained stable by liver PAH activity (Cleary 2013, Gonzales 2016, Vogel 2017). Interestingly, treatment of patients with milder forms of PKU with a synthetic form of a cofactor tetrahydrobiopterin (BH4) (Sapropterin dihydrochloride) has been shown efficacious not only in lowering of blood Phe levels, but also has demonstrated improvement in neurological outcomes such as reduction in ADHD symptoms (Burton 2015). This therapy increases residual PAH enzyme activity by acting as a pharmacological chaperone and hence can provide partial correction of the genetic defect by providing normal Phe regulated PAH activity (Blau 2015). Another therapy recently approved consists of an enzyme substitution therapy using a PEGylated form of bacterial phenylalanine ammonia lyase (PAL) that metabolizes Phe into trans-cinnamic acid. This therapy provides significant reduction in blood Phe levels but appears to be less efficacious on neurological endpoints (Longo 2014). It remains unclear whether this or any other therapies based on mainly lowering blood Phe levels in the absence of correcting the PAH function as a regulator of systemic Phe levels and a producer of Tyr can address the cognitive and neuropsychiatric issues observed even in diet compliant PKU patients.

Restoring the Phe hydroxylase activity into livers of PKU patients by gene Pah gene transfer is an attractive approach to treat the disease. Provided that sufficient PAH expression can be restored, it should provide stable and low blood Phe levels. Several studies have shown that rAAV-mediated delivery of a cDNA encoding PAH to the livers of $Pah^{enu2}$ mice reduces blood Phe levels to within the normal range and corrects behavior (Mochizuki 2004; Ding 2006; Harding 2006, Yagi 2011, Winn 2018). On average, one rAAV copy/cell or minimum of 10% of normal PAH activity in liver is enough to correct the defect in liver (Hamman 2010, Yagi 2011, Viecelli 2014). Hepatocyte repopulation studies using wild-type hepatocytes or hepatocytes from heterozygous $Pah^{enu2/+}$ donors into PKU mice showed that 3-10% of liver repopulation with either hepatocytes partially reduced blood Phe levels and blood Phe levels were completely corrected with 10% of liver repopulation (Hamman 2010). Proof of this concept was recently shown with gene therapy trial delivering a functional Pah gene copy to liver; however, a relatively large vector dose was needed (Chatterjee 2020). What is needed is an improved rAAV vector for efficient gene transfer to liver, robust expression of hPAH in liver and subsequent correction of the PKU pathology.

All references cited herein, including patent applications and publications, are incorporated by reference in their entirety.

BRIEF SUMMARY OF THE INVENTION

The present invention is based at least in part on the Inventor's development of an expression cassette that encodes phenylalanine hydroxylase (PAH). The expression cassette was able to drive transgene expression in liver cells in both human cell culture, livers of PKU mouse models, and the livers of non-human primates. Further, the expression cassette produced wild type, human PAH polypeptide that was enzymatically active. Thus, rAAV vectors with this expression cassette could provide a path for PKU gene therapy by allowing efficacy with reduced vector doses.

In some aspects, the invention provides a recombinant adeno-associated virus (rAAV) particle comprising an rAAV vector, wherein the rAAV vector comprises an expression cassette for expressing a transgene in a liver cell, wherein the expression cassette comprises a transgene operably linked to a promoter and enhancer, wherein the promoter comprises a mouse transthyretin (mTTR) promoter and the enhancer comprises one or two modified prothrombin enhancers (pPrT2), one or two modified alpha1-microbikunin enhancers (mA1MB2), a modified mouse albumin enhancer (mEalb), a hepatitis B virus enhancer II (HEII) or a CRM8 enhancer, wherein the transgene encodes a PAH polypeptide; wherein the AAV viral particle comprises an AAV-XL32 or an AAV-XL32.1 capsid. In some embodiments, the mTTR promoter is a mTTR482 promoter. In some embodiments, the enhancer is 5' to the mTTR promoter.

In some aspects, the invention provides a recombinant adeno-associated virus (rAAV) particle comprising an rAAV vector, wherein the rAAV vector comprises an expression cassette for expressing a transgene in a liver cell, wherein the expression cassette comprises a transgene operably linked to a promoter and a 3' element, wherein the promoter comprises a mouse transthyretin (mTTR) promoter and the 3' element is an albumin 3' element (3'Alb) or an albumin 3' element linked to a human alpha 1 antitrypsin scaffold/matrix attachment region (SMAR) (3'AlbSMAR), wherein the transgene encodes a PAH polypeptide; wherein the AAV viral particle comprises an AAV-XL32 or an AAV-XL32.1 capsid. In some embodiments, the mTTR promoter is a mTTR482 promoter. In some embodiments, the 3' element is located 3' to the transgene.

In some aspects, the invention provides a recombinant adeno-associated virus (rAAV) particle comprising an rAAV vector, expression cassette for expressing a transgene in a liver cell, wherein the expression cassette comprises a transgene operably linked to a promoter and enhancer and a 3' element, wherein the promoter comprises a mouse transthyretin (mTTR) promoter and the enhancer comprises one or two modified prothrombin enhancers (pPrT2), one or two modified alpha1-microbikunin enhancers (mA1MB2), a modified mouse albumin enhancer (mEalb), a hepatitis B virus enhancer II (HEII) or a CRM8 enhancer; and wherein the 3' element is an albumin 3' element (3'Alb) or an albumin 3' element linked to a human alpha 1 antitrypsin scaffold/matrix attachment region (SMAR) (3'AlbSMAR), wherein the transgene encodes a PAH polypeptide; wherein the AAV viral particle comprises an AAV-XL32 or an AAV-XL32.1 capsid. In some embodiments, the mTTR promoter is a mTTR482 promoter. In some embodiments, the enhancer is 5' to the mTTR promoter. In some embodiments, the 3' element is located 3' to the transgene.

In some embodiments of the above aspects, the the expression cassette further comprises an intron. In some embodiments, the intron is a chicken β-actin/rabbit β-globin hybrid intron. In some embodiments, the expression cassette further comprises a polyadenylation signal. In some embodiments, the polyadenylation signal is a bovine growth hormone polyadenylation signal.

In some embodiments of the above aspects, the PAH polypeptide is a wild type PAH polypeptide. In some embodiments, the PAH polypeptide is a human PAH polypeptide. In some embodiments, the PAH polypeptide comprises the amino acid sequence of SEQ ID NO:1. In some embodiments, the transgene is at least 80% identical to the nucleic acid sequence of SEQ ID NO:2.

In some embodiments of the above aspects, the rAAV vector comprises the expression cassette flanked by one or more AAV inverted terminal repeat (ITR) sequences. In some embodiments, the expression cassette of any one of claims 1-18 is flanked by two AAV ITRs. In some embodiments, the AAV ITRs are AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the vector is a self-complimenting vector. In some embodiments, the vector comprises first nucleic acid sequence encoding the PAH polypeptide and a second nucleic acid sequence encoding a complement of the PAH polypeptide, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence.

In some embodiments of the above aspects, the AAV capsid is an AAV-XL32 capsid. In some embodiments, the AAV-XL32 capsid comprises an AAV-XL32 capsid protein comprising an amino acid sequence at least 90%, 95%, 99% or 100% identical to SEQ ID NO:3. In some embodiments, the AAV-XL32 capsid comprises a VP1, a VP2, and a VP3, wherein the VP1, VP2, and VP3 are encoded by the nucleic acid sequence of SEQ ID NO: 4. In some embodiments, the AAV capsid is an AAV-XL32.1 capsid. In some embodiments, the AAV-XL32.1 capsid comprises an amino acid sequence at least 90%, 95%, 99%, or 100% identical to SEQ ID NO:3. In some embodiments, the AAV-XL32.1 capsid comprises a VP1, a VP2, and a VP3, wherein the VP1, VP2, and VP3 are encoded by the nucleic acid sequence of SEQ ID NO:6.

In some aspects, the invention provides a composition comprising any of the rAAV particles described herein. In some embodiments, the composition further comprises a pharmaceutically acceptable carrier.

In some aspects, the invention provides a cell comprising any of the rAAV particles described herein. In some aspects, the invention provides a method of producing a PAH polypeptide, the method comprising culturing a cell as described herein under conditions to produce the PAH polypeptide. In some embodiments, the methods further comprise the step of purifying the PAH polypeptide.

In some aspects, the invention provides methods for treating phenylketonuria in an individual in need thereof, comprising administering to the individual a rAAV particle as described herein. In some aspects, the invention provides methods for treating phenylketonuria in an individual in need thereof, comprising administering to the individual a composition as described herein. In some embodiments, the invention provides methods for treating phenylketonuria in an individual in need thereof, comprising administering to the individual the cell as described herein. In some embodiments, the individual lacks PAH activity.

In some aspects, the invention provides methods for reducing the level of phenylalanine in the blood of in an individual in need thereof, comprising administering to the individual the rAAV particle as described herein. In some aspects, the invention provides methods for reducing the level of phenylalanine in the blood of in an individual in need thereof, comprising administering to the individual the composition as described herein. In some aspects, the invention provides methods for reducing the level of phenylalanine in the blood of in an individual in need thereof, comprising administering to the individual the cell as described herein. In some embodiments, the level of phenylalanine in the blood of the individual prior to treatment is elevated compared to the level of phenylalanine in the blood of peer-matched control individuals. In some embodiments, the rAAV particle, composition or cell is administered intravenously, intraarterially, intrahepatically, intraportally, intraperitoneally, or subcutaneously.

In some embodiments, the administration is in combination with another therapy. In some embodiments, the another therapy is treatment with tetrahydribiopterin, treatment with phenylalanine ammonia lyase (PAL) or pegylated PAL, or a phenylalanine-restricted diet.

In some embodiments, the invention provides kits comprising any of the rAAV particles, the compositions, or the cell as described herein. In some embodiments, the kit further comprises instructions for use; buffers and/or pharmaceutically acceptable excipients; and/or bottles, vials and/or syringes.

BRIEF DESCRIPTION OF THE DRAWINGS

FIG. 1A shows PAH activity levels. 13C-Phe was used as a substrate and assay was run for 30 min. The amount of product (13C-Tyr) generated was measured by LC-MS/MS and values were normalized for total protein. The identities of the samples are indicated on the x-axis, including, from left to right, a mock control, hPAH/G, hPAH-V1/G, hPAH/E (wild-type hPAH), hPAH-Vl/E, and murine PAH (mPAH). The y-axis shows the level of PAH activity (µM 13C Tyr/mg protein). FIG. 1B shows a Western blot showing PAH protein levels. Cell lysates (15 µg/lane) were run on a SDS-PAGE gel, transferred to a membrane and then probed with anti-PAH antibody, reactive to both human and mouse PAH protein The identities of the samples are indicated above the blot, including, from left to right, hPAH-V1/G, wild type hPAH/E, hPAH-Vl/E, hPAH/G, and mPAH. FIG. 1C shows a quantification of PAH protein levels as determined by Western blot using AzureSpot software. The identities of the samples are indicated on the x-axis, including, from left to right, hPAH-V1/G, wild type hPAH/E, hPAH-Vl/E, hPAH/G, and mPAH. In FIGS. 1A-1C, "hPAH-V1/G" indicates human PAH variant 1 with an E183G amino acid substitution; "WT hPAH/E" indicates wild type human PAH with an E183 residue; "hPAH-V1/G" indicates human PAH variant 1 with an E183 residue; "hPAH/G" indicates mutant human PAH with an E183G amino acid substitution; and "mPAH" indicates FLAG-tagged mouse PAH, used as a positive control.

FIG. 2A shows EGFP protein levels in human liver cell line (Huh7 cells) transduced with AAV vectors containing a CBA-EGFP expression cassette using, from left to right, AAV8, AAV-DJ, AAV-LK03, AAV-XL14, and AAV-XL32 capsid vectors. FIG. 2B shows the level of vector genomes/cell in NHP liver (dark gray) and spleen (light gray). Vector genome copies were measured 2 weeks later by qPCR after IV delivery of 5e12 vg/kg. VG copies in liver and spleen in each animal 14 days post vector administration are shown. Values for liver represent the average of four samples collected from various locations. Values for spleen are the average of two adjacent samples collected from the middle section of the spleen. FIG. 2C shows the level of vector genomes/cell in NHP kidney (dark gray), muscle (light gray), and heart (medium gray). Values represent the average of two adjacent samples collected from each tissue. The identity of the capsid protein is indicated along the x-axis, including, from left to right, AAV8, AAV-DJ, AAV-LK03, AAV-XL14, or AAV-XL32. FIG. 2D shows a summary of vector biodistribution comparison of the five capsids compared. The level of vector genomes/cell is shown on the y-axis for the liver, spleen, muscle, heart, or kidney of NHPs administered with vectors with AAV8, AAV-DJ, AAV-LK03, AAV-XL14, or AAV-XL32 capsid vectors, as indicated from left to right on the x-axis. FIG. 2E shows expression of EGFP in three portions of the right medial lobe and one portion of the left medial lobe following administration of AAV8, AAV-DJ, AAV-LK03, AAV-XL14, or AAV-XL32 capsid vectors.

FIG. 3A shows the abundance of vector genomes in NHP livers, as indicated on the y-axis, in NHPs that were administered a vehicle only control, or 5e11, 2e12, 5e12 and 2e13 vg/kg doses of XL32.1/mA1MB2-mTTR482-, as indicated on the x-axis. Average vector genome copies/cell are indicated in bottom X-axis panel (n=3/dosing cohort). M, male NHPs, F, female NHPs (Significance: *, $p<0.05$; **, $p<0.01$). FIG. 3B. shows the level of vector derived transcripts in NHP liver, as indicated on the y-axis, in NHPs that were administered a vehicle only control, or 5e11, 2e12, 5e12 and 2e13 vg/kg doses of XL32.1/mA1MB2-mTTR482-EGFP, as indicated on the x-axis. FIG. 3C shows EGFP protein levels, as indicated on the y-axis, in NHPs that were administered a vehicle only control, or 5e11, 2e12, 5e12 and 2e13 vg/kg doses of XL32.1/mA1MB2-mTTR482-EGFP, as indicated on the x-axis. FIG. 3D shows correlation between liver vector genome and vector derived mRNA copies (high dose 2e13 vg/kg omitted in this analysis). FIG. 3E shows correlation between vector derived mRNA copies and eGFP protein levels in liver.

FIG. 4A shows an image of a representative in situ hybridization to detect the vector in liver. Detection in animal #203 (2e12 vg/kg group) is shown as an example on the right (3 vg/cell by qPCR). FIG. 4B shows the percentage of EGFP-vector DNA positive cells in the liver detected by in situ hybridization as indicated on the y-axis, in NHPs that were administered a vehicle only control, or 5e11, 2e12, 5e12 and 2e13 vg/kg doses of XL32.1/mA1MB2-mTTR482-EGFP, as indicated on the x-axis. FIG. 4C shows the correlation between the average number of VG copies, as determined by qPCR (y-axis), to the percentage of VG positive cells, as determined by in situ hybridization (x-axis).

FIG. 5A shows the level of vector genomes/cell in liver and various other organs. Values for liver represent the average of 3 animals in each group (with each animal tested for one sample from right and left medial lobes), and values for other organs are an average of three animals (with one sample/animal). FIG. 5B shows the level of vector derived mRNA in the liver. Each value represents an average per treatment group (with each animal n=2).

FIG. 6A shows a time-course for blood Phe levels. FIG. 6B shows blood Phe levels on day 36 (HOM not included for observation of differences). FIG. 6C shows a time-course for blood Tyr levels. FIG. 6D shows blood Tyr levels on day 36. The vector (with mA1MB2-mTTR482 promoter) was administered into adult male homozygous Pah-KO mice at doses of 1e11, 3e11 and 1e12 vg/mouse by IV route. The vector treatment cohorts contain n=8-10 animals/group, HETs, n=10 and C57BL66, n=5. Abbreviations: HOM, homozygous Pah-KO mice; HETs, heterozygous Pah-KO mice; C57BL/6, wild-type mice.

FIG. 7A shows vector DNA copies in liver. FIG. 7B shows vector DNA in all tissues tested (liver, spleen, muscle, kidney and lung). FIG. 7C shows vector derived mRNA levels in liver. FIG. 7D shows the correlation of vector genomes to vector derived mRNA levels per cell in liver. FIG. 7E shows the correlation of vector genomes in liver to blood Phe levels. Each data point represents one animal. Normalization per cells based on 5 pg DNA/cell (vg/cell) and 30 pg/cell (mRNA/cell). Abbreviations: HOM, homozygous PAH-KO mice FIGS. 8A-8C show the analysis of PAH activity and protein levels after delivery with XL32.1/WT hPAH in livers of Pah-KO mice. FIG. 8A shows PAH activity in liver homogenates. FIG. 8B shows PAH protein detection by Western blot. FIG. 8C shows the localization of PAH positive cells by PAH immunohistochemistry. The vector treatment cohorts contain n=8-10 animals/group, HETs, n=10 and C57BL, n=5. For the Western blot, three representative animals in each cohort were used for analysis and their equal protein loading is indicated by b-actin probing.

FIG. 9A shows brain Phe, Tyr and Trp levels. FIG. 9B shows brain neurotransmitter dopamine, norepinephrine and serotonin levels. Each data point represents one animal. For brain amino acid analysis, the vector treatment cohorts contain n=7-10 animals/group, HETs, n=9 and C57BL/6, n=5. For brain neurotransmitter analysis, the vector treatment cohorts contain n=7 animals/group, HETs, n=6 and C57BL/6, n=4. Statistical analysis by 1-way ANOVA.

FIG. 10A shows images of nest quality for each score ranging from sore of 1 (poor quality) to 5 (high quality). FIG. 10B shows the scoring of animals prior and post rAAV-XL32.1/WT hPAH treatment. Each data point represents one animal. The vector treatment cohorts contain n=8-10 animals/group, HETs, n=10 and C57BL/6, n=5 Statistical analysis by 1-way ANOVA.

FIG. 11A show that body weights were significantly different in Pah-KO mice (HOM and treatment cohorts) compared to HET and WT (C57BL/6) mice prior to treatment. FIG. 11B shows that after 4-months of treatment with WT PAH, there was a significant increase in body weights at two higher dose cohorts compared to untreated HOM mice. FIG. 11C shows the liver weighs increased in the treatment groups and were similar to the HET and WT mice. Significance, *, $p<0.05$; , $p<0.01$, *, $p<0.001$ and ****, $p<0.0001$ by One-way ANOVA with Tukey's multiple comparison. Each data point represents one animal (n per group, HOM=9; low dose, n=6; med dose, n=8, high dose, n=8, HET, n=8 and WT, n=8). Abbreviations: HOM, homozygous Pah-KO mice; HETs, heterozygous Pah-KO mice; WT, wild-type C57BL/6 mice. Doses vg/mouse.

FIG. 12A shows the average blood Phe levels in each cohort over 120 days. Blood Phe levels in individual mice 7 days (FIG. 12B) and 120 days post treatment (FIG. 12C). All treatment groups (doses vg/mouse) significantly reduced blood Phe levels compared to untreated HOM mice. There was no significant difference between WT PAH treatment groups at 3e11 and 1e12 doses compared to HET and WT mice at either timepoint. Dose 1e11 exhibit variability and was not comparable to HET/WT. Animal number, statistical analysis and abbreviations as in FIG. 11A-11C legend.

FIG. 13A shows vector DNA copies in liver and FIG. 13B shows vector derived mRNA levels in liver. Both endpoints showed dose-responsive increase. There was a good correlation of vector genomes to vector derived mRNA levels per cell in liver (FIG. 13C) and correlation of vector genomes in liver to blood Phe levels (FIG. 13D). The latter showed that blood Phe normalization (100 uM) required at minimum 0.1 VG/cell. FIG. 13E shows representative images on in situ detection for vector DNA (red) and transcripts (green) are shown in H&E-stained sections for each treatment cohort. Animal numbers, statistical analysis and abbreviations as in FIGS. 11A-11C.

FIG. 14A shows PAH activity in liver homogenates. The PAH enzymatic activity in 1e11 and 3e11 treatment cohorts was not significantly different from activity in HET mice while 1e12 treatment generated significantly more PAH activity than observed in normal mice. FIG. 14B shows production of PAH protein was confirmed by PAH IHC in liver sections and the HALO analysis was used to quantitate the percentage of PAH positive cells. FIG. 14C shows the correlation of this to vector DNA copies in liver showed that blood Phe normalization (100 μM) required at minimally 20% of PAH positive cells. FIG. 14D shows representative images of PAH IHC for all study cohorts. Percent PAH positive cells in each image (animal #) are: HOM (#4), 0%; 1e11 (#19), 38%; 3e11 (#21), 62%; 1e12 (#34), 72%; HET (#46), 94% and WT (#56), 99%.

FIG. 15A shows brain Phe, Tyr and Trp levels. All treatment cohorts significantly reduced brain Phe levels though variability was observed in the low (1e11 vg/mouse) dose cohort. In this group, the three animals with higher brain Phe levels correlated to higher blood Phe and lower gene transfer to liver. FIG. 15B shows brain neurotransmitter dopamine, norepinephrine and serotonin levels. Again, the three animals in low dose group with lower neurotransmitter levels represent the animals with higher blood Phe levels. Animal numbers, statistical analyses and abbreviations as in FIGS. 11A-11C legend.

FIG. 16A-16C show the effect of AAVXL32.1/WT hPAH delivery to liver on brain white matter content. The white matter content was analyzed by quantitating corpus callosum volume by MRI. This was measured prior to treatment (FIG. 16A) and 106 days (FIG. 16B) post treatment in live animals. FIG. 16C shows the percentage change in corpus callosum volume for each animal. All the treated animals had a significant increase while no change was observed in HET and WT animals within the 4-month study. The untreated Pah-KO mice (HOM) showed a slight decrease during this time. FIG. 16D shows Brain weights at the end of the study (day 120 post treatment). Only 3e11 dose cohort showed significant increase in brain weight and did not reach the brain weights of normal animals. Animal numbers, statistical analysis and abbreviations as in FIG. 11A-11C legend.

FIG. 17A shows behavior assessed by nest building assay where the quality of the nest is scored (score of 1, no nest or poor quality to 5, high quality). FIG. 17B shows the results of a nest building assay that was performed prior to treatment and 35 and 97 days post treatment. Improved in nesting scores was already observed on 35 and persistent until day 97 after the treatment. The three animals in low dose group with lower scores represent the animals with higher blood Phe levels. Animal numbers, statistical analysis and abbreviations as in FIG. 11A-11C legend.

FIG. 18A shows a diagram of vectors. The rAAVXL32.1/mA1MB2-mTTR482-WT hPAH (A1MB2) represents the same vector as used in the 4-month study. The rAAVXL32.1/LP1-HI2 contains LP1 promoter with same intron as used for rAAVXL32.1/mA1MB2-mTTR482-WT hPAH. The rAAVXL32.1/LP1-SI construct has identical promoter and intron as used for hemophilia B trial (Nathwani 2011). For in vitro analysis in human liver line, each ITR containing plasmid construct was transiently transfected into Huh7 cells in triplicate and cell lysates were generated 3 days later. FIG. 18B shows PAH protein levels in human cells in vitro. Ten μg of cell lysates were run per lane and PAH levels were analyzed by Western blot using anti-PAH antibody. Equal loading is shown with β-actin detection. FIG. 18C shows PAH activity assay in human cells in vitro. The Phe to Tyr conversion was measured by colorimetric assay and was normalized to total protein measured by BCA. The data demonstrated higher PAH protein and activity generated by A1MB2 construct in human liver cells. For in vivo analysis, each vector was administered IV at 3e11 vg/mouse into PAH-KO mice and evaluated for 5 weeks. FIG. 18D shows plasma Phe levels 36 days post vector delivery. FIG. 18E shows liver vector derived transcript levels in each treatment cohort. FIG. 18F shows liver PAH activity in each treatment cohort. FIG. 18G shows PAH activity normalized by vector DNA in each animal. PAH activity was normalized by vector DNA due to observed variability in vector DNA levels in liver. Significance, *, $p<0.05$; , $p<0.01$, *, $p<0.001$ and ****, $p<0.0001$ by One-way ANOVA with Tukey's multiple comparison. Each data point represents one animal (all grps n=10 except HOM, n=4).

DETAILED DESCRIPTION

Figure 1A:
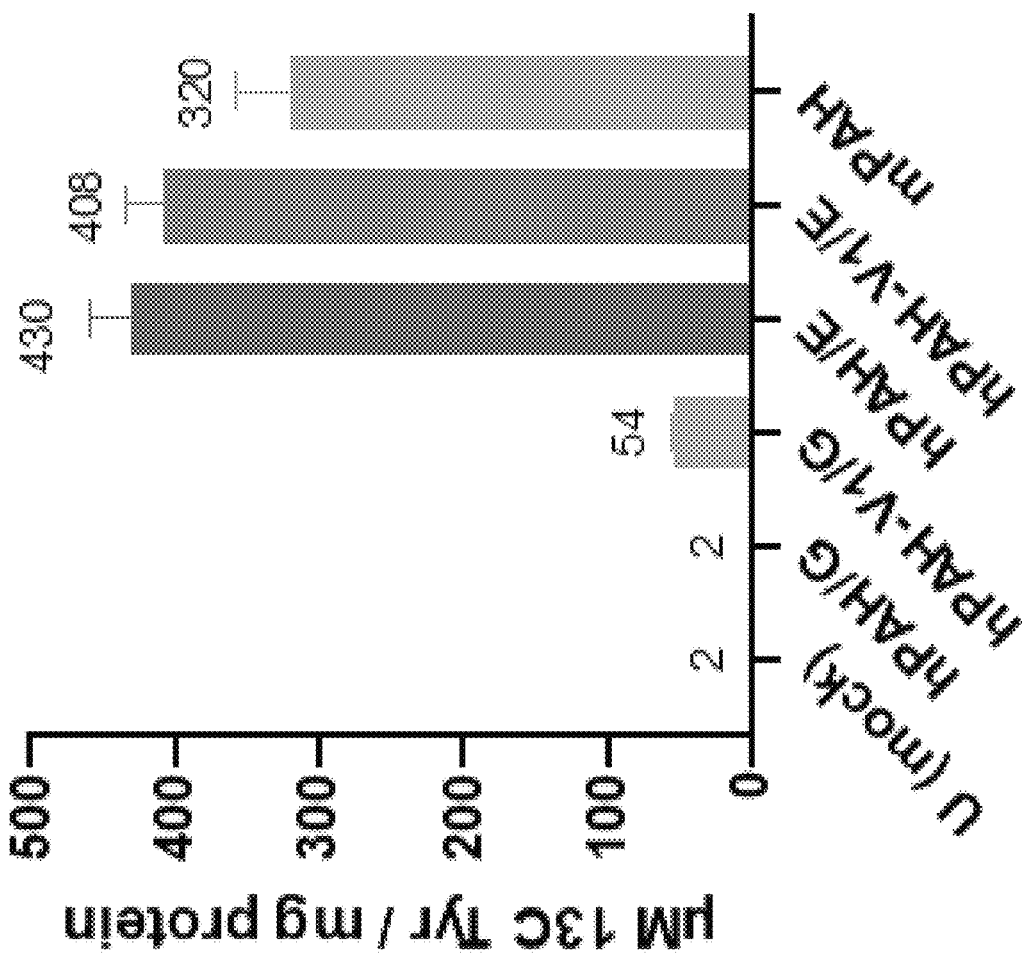
FIGS. 1A-1C show in vitro comparisons of PAH protein and activity levels of wild type PAH and PAH variants. Four expression plasmids (n=2/plasmid) were transfected into Huh7 cells, a human liver cell line, and 72 hours later, cells were collected to prepare a lysate.

In some aspects, the invention provides expression cassettes, recombinant adeno-associated virus (rAAV) vectors, and viral particles and pharmaceutical compositions comprising the a transgene encoding a PAH polypeptide. In further aspects, the invention provides methods for treating phenylketonuria (PKU); for example, by increasing PAH activity, increasing tyrosine and tryptophan transport into the brain, and normalizing brain neurotransmitter levels including dopamine and serotonin. In yet further aspects, the invention provides kits for treating PKU in an individual with an expression cassette of the present disclosure.

General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., $4^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); PCR 2: *A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, $6^{th}$ ed., J. Wiley and Sons, 2010); *Oligonucleotide Synthesis* (M. J. Gait, ed., 1984); *Methods in Molecular Biology, Humana Press; Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—$NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one and in embodiments two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, and in embodiments two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV vector can be in any of a number of forms, including, but not limited to, plasmids, linear artificial chromosomes, complexed with lipids, encapsulated within liposomes, and encapsidated in a viral particle, particularly an AAV particle. A rAAV vector can be packaged into an AAV virus capsid to generate a "recombinant adeno-associated viral particle (rAAV particle)".

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome.

"Chicken β-actin (CBA) promoter" refers to a polynucleotide sequence derived from a chicken β-actin gene (e.g., *Gallus gallus* beta actin, represented by GenBank Entrez Gene ID 396526). As used herein, "chicken β-actin promoter" may refer to a promoter containing a cytomegalovirus (CMV) early enhancer element, the promoter and first exon and intron of the chicken β-actin gene, and the splice acceptor of the rabbit beta-globin gene, such as the sequences described in Miyazaki, J. et al. (1989) *Gene* 79(2):269-77. As used herein, the term "CAG promoter" may be used interchangeably. As used herein, the term "CMV early enhancer/chicken beta actin (CAG) promoter" may be used interchangeably.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The term "vector genome (vg)" as used herein may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a stuffer, a sequence of interest (e.g., an RNAi), and a polyadenylation sequence. A complete vector genome may include a complete set of the polynucleotide sequences of a vector. In some embodiments, the nucleic acid titer of a viral vector may be measured in terms of vg/mL. Methods suitable for measuring this titer are known in the art (e.g., quantitative PCR).

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

"AAV helper functions" refer to functions that allow AAV to be replicated and packaged by a host cell. AAV helper functions can be provided in any of a number of forms, including, but not limited to, helper virus or helper virus genes which aid in AAV replication and packaging. Other AAV helper functions are known in the art such as genotoxic agents.

A "helper virus" for AAV refers to a virus that allows AAV (which is a defective parvovirus) to be replicated and packaged by a host cell. A helper virus provides "helper functions" which allow for the replication of AAV. A number of such helper viruses have been identified, including adenoviruses, herpesviruses and, poxviruses such as vaccinia and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Examples of adenovirus helper functions for the replication of AAV include E1A functions, E1B functions, E2A functions, VA functions and E4orf6 functions. Baculoviruses available from depositories include *Autographa californica* nuclear polyhedrosis virus.

A preparation of rAAV is said to be "substantially free" of helper virus if the ratio of infectious AAV particles to infectious helper virus particles is at least about $10^2$:1; at least about $10^4$:1, at least about $10^6$:1; or at least about $10^8$:1 or more. In some embodiments, preparations are also free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or MEGALIGN™ (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this disclosure, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

As used herein, "phenylalanine hydroxylase (PAH)" is an enzyme (EC 1.14.16.1) that catalyzes the hydroxylation of the aromatic side-chain of phenylalanine to generate tyrosine. PAH is a monooxygenase that uses tetrahydrobiopterin (BH4, a pteridine cofactor) and a non-heme iron for catalysis. During the reaction, molecular oxygen is heterolytically cleaved with sequential incorporation of one oxygen atom into BH4 and phenylalanine substrate. The hydroxylation of phenylalanine to tyrosine and is the rate-limiting step in phenylalanine catabolism and a deficiency of this enzyme activity results in the autosomal recessive disorder phenylketonuria. PAH may also be referred to as PH, PKU, or PKU1. PAH is a multi-domain protein consisting of N-terminal regulatory (1-117), central catalytic (118-410) and C-terminal tetramerization domains (411-452). Human PAH is provided in GenBank; for example, GenBank: AAA60082.1, NCBI Reference Sequence: NP_000268.1 (protein), and NCBI Reference Sequence: NM_000277.3 (mRNA). An example of a wild type human PAH is provided as SEQ ID NO: 1.

As used herein, "Phenylketonuria (PKU)" refers to a genetic deficiency of liver enzyme phenylalanine hydroxylase (PAH). In the absence of any treatment, the severe form of PKU leads to highly elevated blood Phe levels that are neurotoxic and associated with severe mental retardation.

"mTTR promoter" refers to a polynucleotide sequence derived from the murine transthyretin gene. An example of a mTTR promoter, mTTR482, is provided by Kyostio-Moore, (2016) and Nambiar (2017).

"Modified prothrombin enhancer (mPrT2)" refers to two copies of polynucleotide sequence derived from a human prothrombin gene. An example of a mPrT2 enhancer is provided by (McEachern 2006, Jacobs 2008). An example of a mPrT2 sequence is provided by SEQ ID NO:7.

"Modified alpha1-microbikunin (mA1MB2)" refers to two copies of polynucleotide sequence derived from a human alphal-microglobulin/bikunin gene. An example of a mA1MB2 is enhancer by (McEachern 2006, Jacobs 2008). An example of a mA1MB2 sequence is provided by SEQ ID NO:8.

"Modified mouse albumin enhancer (mEalb)" refers to a polynucleotide sequence derived from the murine albumin gene. An example of a mEalb enhancer is provided by (Kramer 2003). An example of a mEalb sequence is provided by SEQ ID NO:9.

"Hepatitis B virus enhancer II (HEII)" refers to a polynucleotide sequence derived from hepatitis B virus, located upstream of the PreCore promoter. An example of a hEII enhancer is provided by (Kramer 2003). An example of a HEII sequence is provided by SEQ ID NO:10.

"CRM8" refers to a cis-acting regulatory module derived from a polynucleotide sequence from the human Serpinal gene (Chuah 2014). An example of a CRM8 sequence is provided by SEQ ID NO:11.

"Alb 3'" refers to a polynucleotide sequence 3' to the coding region of the human albumin gene. An example of an Alb 3' element is provided by Wooddell (2008). An example of an Alb 3' sequence is provided by SEQ ID NO:12. "Alb3'/SMAR" refers to Alb3' linked to a scaffold/matrix attachment region of the human alphal-antitrypsin gene (AF156542). An example of a Alb3'/SMAR sequence is provided by SEQ ID NO:13.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the disclosure described herein include "comprising," "consisting," and/or "consisting essentially of" aspects and embodiments.

Liver Specific Expression Cassettes

In some aspects, the invention provides expression cassettes for expressing a transgene in a liver cell, wherein the expression cassette comprises a transgene operably linked to a promoter and enhancer, wherein the promoter comprises a mouse transthyretin (mTTR) promoter and the enhancer comprises one or two modified prothrombin enhancers (mPrT2), one or two modified alpha1-microbikunin enhancers (mA1MB2), a modified mouse albumin enhancer (mEalb), a hepatitis B virus enhancer II (HE11) or a CRM8 enhancer. In some embodiments, the mTTR promoter is a mTTR482 promoter. In some embodiments, the promoter comprises an mTTR core promoter and an mTTR upstream enhancer. In some embodiments, the enhancer is 5' to the mTTR promoter. In some embodiments, the transgene encodes a PAH polypeptide as described herein.

In some embodiments, the invention provides expression cassettes for expressing a transgene in a liver cell, wherein the expression cassette comprises a transgene operably linked to a promoter and a 3' element, wherein the promoter comprises a mouse transthyretin (mTTR) promoter and the 3' element is an albumin 3' element (3'Alb) or an albumin 3' element linked to a human alpha 1 antitrypsin scaffold/matrix attachment region (SMAR) (3'AlbSMAR). In some embodiments, the mTTR promoter is a mTTR482 promoter. In some embodiments, the 3' element is located 3' to the transgene. In some embodiments, the transgene encodes a PAH polypeptide as described herein.

In some embodiments, the invention provides expression cassettes for expressing a transgene in a liver cell, wherein the expression cassette comprises a transgene operably linked to a promoter and enhancer and a 3' element, wherein the promoter comprises a mouse transthyretin (mTTR) promoter and the enhancer comprises one or two modified prothrombin enhancers (mPrT2), one or two modified alpha1-microbikunin enhancers (mA1MB2), a modified mouse albumin enhancer (mEalb), a hepatitis B virus enhancer II (HE 11) or a CRM8 enhancer; and wherein the 3' element is an albumin 3' element (3'Alb) or an albumin 3' element linked to a human alpha 1 antitrypsin scaffold/matrix attachment region (SMAR) (3'AlbSMAR). In some embodiments, the mTTR promoter is a mTTR482 promoter. In some embodiments, the enhancer is 5' to the mTTR promoter. In some embodiments, the 3' element is located 3' to the transgene. In some embodiments, the transgene encodes a PAH polypeptide as described herein.

In some embodiments, the invention provides an expression cassette for expressing a transgene in a liver cell, wherein the transgene encodes a PAH polypeptide. In some embodiments, the PAH polypeptide is a wild type PAH polypeptide. In some embodiments, the PAH polypeptide is a human PAH polypeptide. In some embodiments, the PAH polypeptide comprises the amino acid sequence of SEQ ID NO:1. In some embodiments, the PAH polypeptide is at least 90%, 91%, 92%, 93%, 94%, 95%, 96%, 97%, 98%, or 99% identical the amino acid sequence of SEQ ID NO:1. In some embodiments, the transgene is at least 80%, 85%, 90%, 91%, 92%, 93%, 94%, 95%, 96%, 97%, 98%, or 99% identical to the nucleic acid sequence of SEQ ID NO:2. In some embodiments, the PAH polypeptide comprises an E183 residue. In some embodiments, the PAH polypeptide comprises a glutamic acid residue at amino acid residue number 183. In some embodiments, the PAH polypeptide shows a higher level of PAH activity than a PAH polypeptide comprising an E183G amino acid substitution.

In some embodiments, the transgene encoding a PAH polypeptide is codon-optimized. In some embodiments, the transgene encoding a PAH polypeptide is codon optimized for expression in a particular cell, such as a eukaryotic cell. Eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon usage tables are readily available, for example, at the "Codon Usage Database", and these tables can be adapted in a number of ways (see, e.g., Nakamura, Y. et al. (2000) *Nucleic Acids Res.* 28:292). Computer algorithms for codon optimizing a particular sequence for expression in a particular host cell are also available, such as Gene Forge (Aptagen; Jacobus, Pa.), DNA2.0, GeneArt (GA) or Genscript (GS) and a GS algorithm combined with reduction in CpG content. In some embodiments, a transgene encoding the PAH polypeptide is codon optimized using the GA algorithm.

In some embodiments, the expression cassette further comprises an intron. A variety of introns for use in the invention are known to those of skill in the art, and include the MVM intron, the F IX truncated intron 1, the β-globin SD/immunoglobin heavy chain SA, the adenovirus SD/immunoglobin SA, the SV40 late SD/SA (19S/16S), and the hybrid adenovirus SD/IgG SA. (Wu et al. 2008, Kurachi et al., 1995, Choi et al. 2014, Wong et al., 1985, Yew et al. 1997, Huang and Gorman (1990). In some embodiments, the intron is a chicken β-actin (CBA)/rabbit β-globin hybrid intron. In some embodiments, intron is a chicken β-actin (CBA)/rabbit β-globin hybrid promoter and intron where all the ATG sites are removed to minimize false translation start sites (SEQ ID NO:15). In some embodiments the intron is an MVM intron, a F IX truncated intron 1, a β-globin SD/immunoglobin heavy chain SA, an adenovirus SD/immunoglobin SA, a SV40 late SD/SA (19S/16S), or a hybrid adenovirus SD/IgG SA. In some embodiments, the intron is a chicken β-actin (CBA)/rabbit β-globin hybrid intron.

In some embodiments, the expression cassette further comprises a polyadenylation signal. In some embodiments, the polyadenylation signal is a bovine growth hormone polyadenylation signal, an SV40 polyadenylation signal, or a HSV TK pA. In some embodiments, the polyadenylation signal is a synthetic polyadenylation signal as described in Levitt, N et al. (1989), *Genes Develop.* 3:1019-1025.

In some embodiments, the expression cassette comprises a stuffer nucleic acid. In some embodiments, the stuffer nucleic acid may comprise a sequence that encodes a reporter polypeptide. As will be appreciated by those of skill in the art, the stuffer nucleic acid may be located in a variety of regions within the nucleic, and may be comprised of a continuous sequence (e.g., a single stuffer nucleic acid in a single location) or multiple sequences (e.g., more than one stuffer nucleic acid in more than one location (e.g., 2 locations, 3 locations, etc.) within the nucleic acid. In some embodiments, the stuffer nucleic acid may be located downstream of the transgene encoding the PAH polypeptide. In embodiments, the stuffer nucleic acid may be located upstream of the transgene encoding the PAH polypeptide (e.g., between the promoter and the transgene). As will also be appreciated by those of skill in the art a variety of nucleic acids may be used as a stuffer nucleic acid. In some embodiments, the stuffer nucleic acid comprises all or a portion of a human alpha-i-antitrypsin (AAT) stuffer sequence or a C16 P1 chromosome 16 P1 clone (human C16) stuffer sequence. In some embodiments, the stuffer sequence comprises all or a portion of a gene. For example, the stuffer sequence comprises a portion of the human AAT sequence. One skilled in the art would recognize that different portions of a gene (e.g., the human AAT sequence) can be used as a stuffer fragment. For example, the stuffer fragment may be from the 5' end of the gene, the 3' end of the gene, the middle of a gene, a non-coding portion of the gene (e.g., an intron), a coding region of the gene (e.g. an exon), or a mixture of non-coding and coding portions of a gene. One skilled in the art would also recognize that all or a portion of stuffer sequence may be used as a stuffer sequence. In some embodiments, the stuffer sequence is modified to remove internal ATG codons. In some embodiments, the stuffer sequence comprises the nucleotide sequence of SEQ ID NO:16.

In some embodiments, the expression cassette is incorporated into a vector. In some embodiments, the expression cassette is incorporated into a viral vector. In some embodiments, the vector comprises the nucleic acid sequence of SEQ ID NO: 14. In some embodiments, the viral vector is an rAAV vector as described herein.

Vectors and Viral Particles

In certain aspects, the expression cassette for expressing a PAH polypeptide (e.g., a wild type human PAH polypeptide) is contained in a vector. In some embodiments, the present invention contemplates the use of a recombinant viral genome for introduction of nucleic acid sequences encoding the PAH polypeptide for packaging into a viral particle, e.g., a viral particle described below. The recombinant viral genome may include any element to establish the expression of the PAH polypeptide, for example, a promoter, an ITR, a ribosome binding element, terminator, enhancer, selection marker, intron, polyA signal, and/or origin of replication. Exemplary viral genome elements and delivery methods for viral particles are described in greater detail below.

Non-Viral Delivery Systems

Conventional non-viral gene transfer methods may also be used to introduce nucleic acids into cells or target tissues. Non-viral vector delivery systems include DNA plasmids, naked nucleic acid, and nucleic acid complexed to a delivery system. For example, the vector may be complexed to a lipid (e.g., a cationic or neutral lipid), a liposome, a polycation, a nanoparticle, or an agent that enhances the cellular uptake of nucleic acid. The vector may be complexed to an agent suitable for any of the delivery methods described herein. In some embodiments, the nucleic acid comprises one or more viral ITRs (e.g., AAV ITRs).

Viral Particles

In some embodiments, the vector comprising the expression cassette for expressing a PAH polypeptide (e.g., a wild type human PAH polypeptide) is a recombinant adeno-associated virus (rAAV) vector, a recombinant adenoviral vector, a recombinant lentiviral vector or a recombinant herpes simplex virus (HSV) vector.

rAAV particles

In some embodiments, the vector is a recombinant AAV (rAAV) vector. In some embodiments, the expression cassette for expressing a PAH polypeptide (e.g., a wild type human PAH polypeptide) is flanked by one or more AAV inverted terminal repeat (ITR) sequences. In some embodiments, the viral particle is a recombinant AAV particle comprising an expression cassette for expressing a PAH polypeptide flanked by one or two ITRs. In some embodiments, the expression cassette for expressing a PAH polypeptide is flanked by two AAV ITRs. In some embodiments, the vector comprises the nucleic acid sequence of SEQ ID NO: 14.

In some embodiments, the expression cassette for expressing a PAH polypeptide of the present disclosure operatively linked components in the direction of transcription, control sequences including transcription initiation and termination sequences, thereby forming an expression cassette. The expression cassette is flanked on the 5' and 3' end by at least one functional AAV ITR sequence. By "functional AAV ITR sequences" it is meant that the ITR sequences function as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10):6081-6; and Bossis et al., *J. Virol.*, 2003, 77(12): 6799-810.

Use of any AAV serotype is considered within the scope of the present invention. In some embodiments, a rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV 11, AAV12, a goat AAV, bovine AAV, or mouse AAV ITRs or the like. In some embodiments, the nucleic acid in the AAV comprises an ITR of AAV ITRs are AAV1, AAV2, AAV3, AAV4, AAV5, AAV6, AAV7, AAV8, AAVrh8, AAVrh8R, AAV9, AAV10, AAVrh10, AAV 11, AAV12, a goat AAV, bovine AAV, or mouse AAV or the like. In certain embodiments, the AAV ITRs are AAV2 ITRs.

In some embodiments, a vector may include a stuffer nucleic acid. In some embodiments, the stuffer nucleic acid may encode a green fluorescent protein. In some embodiments, the stuffer nucleic acid may be located 3' to expression cassette for expressing a PAH polypeptide of the present disclosure.

In some aspects, the invention provides viral particles comprising a recombinant self-complementing genome. In some embodiments, the vector is a self-complementary vector. AAV viral particles with self-complementing genomes and methods of use of self-complementing AAV genomes are described in U.S. Pat. Nos. 6,596,535; 7,125, 717; 7,765,583; 7,785,888; 7,790,154; 7,846,729; 8,093, 054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., the coding strand of the PAH polypeptide of the invention) and a second heterologous polynucleotide sequence (e.g., the noncoding or antisense strand of the PAH polypeptide of the present disclosure) wherein the first heterologous polynucleotide sequence can form intrastrand base pairs with the second polynucleotide sequence along most or all of its length.

In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR (e.g., the right ITR). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

In some embodiments, the first heterologous nucleic acid sequence and a second heterologous nucleic acid sequence are linked by a mutated ITR (e.g., the right ITR). In some embodiments, the ITR comprises the polynucleotide sequence 5'-CACTCCCTCTCTGCGCGCT CGCTCGCT-CACTGAGGCCGGGCGACCAAAGGTCGCC-CACGCCCGGGCTTTGCCCGG GCG-3' (SEQ ID NO:17). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

In some embodiments, the vector is encapsidated in a viral particle. In some embodiments, the viral particle is a recombinant AAV viral particle comprising a recombinant AAV vector. Different AAV serotypes are used to optimize transduction of particular target cells or to target specific cell types within a particular target tissue (e.g., a liver tissue). A rAAV particle can comprise viral proteins and viral nucleic acids of the same serotype or a mixed serotype. For example, in some embodiments a rAAV particle can comprise AAV2 capsid proteins of the invention and at least one AAV2 ITR or it can comprise AAV2 capsid proteins and at least one AAV1 ITR. Any combination of AAV serotypes for production of a rAAV particle is provided herein as if each combination had been expressly stated herein. In some embodiments, the invention provides rAAV particles comprising an AAV2 capsid of the invention. In some embodiments, the invention provides rAAV particles comprising an AAVrh8R capsid of the invention. In some embodiments, the invention provides rAAV particles comprising an engineered AAV capsid of the invention. In some embodiments, the invention provides rAAV particles comprising an AAV-XL32 capsid of the invention. In some embodiments, the invention provides rAAV particles comprising an AAV-XL32.1 capsid of the invention.

In some embodiments, the rAAV particles comprise an AAV1 capsid, an AAV2 capsid, an AAV3 capsid, an AAV4 capsid, an AAV5 capsid, an AAV6 capsid (e.g., a wild-type AAV6 capsid, or a variant AAV6 capsid such as ShH10, as described in U.S. PG Pub. 2012/0164106), an AAV7 capsid, an AAV8 capsid, an AAVrh8 capsid, an AAVrh8R capsid, an AAV9 capsid (e.g., a wild-type AAV9 capsid, or a modified AAV9 capsid as described in U.S. PG Pub. 2013/0323226), an AAV10 capsid, an AAVrh10 capsid, an AAV11 capsid, an AAV12 capsid, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, a mouse AAV capsid, a rAAV2/HBoV1 capsid, or an AAV capsid described in U.S. Pat. No. 8,283,151 or International Publication No. WO/2003/042397. In some embodiments, the AAV particles comprise an AAV-XL32.1 capsid. In some embodiments, the AAV particles comprise an AAV-XL32 capsid. In some embodiments, the AAV particles comprise an AAV capsid described in International Publication No. WO 2019241324 A1. In some embodiments, a mutant capsid protein maintains the ability to form an AAV capsid. In some embodiments, the rAAV particle comprises AAV5 tyrosine mutant capsid (Zhong L. et al., (2008) *Proc Natl Acad Sci USA* 105(22):7827-7832. In further embodiments, the rAAV particle comprises capsid proteins of an AAV serotype from Clades A-F (Gao, et al., *J. Virol.* 2004, 78(12):6381). In some embodiments, the rAAV particle comprises an AAV1 capsid protein or mutant thereof. In other embodiments, the rAAV particle comprises an AAV2 capsid protein or mutant thereof. In some embodiments, the AAV serotype is AAV1, AAV2, AAV5, AAV6, AAV7, AAV8, AAVrh8, AAVrh8R, AAV9, AAV10, or AAVrh10. In some embodiments, the rAAV particle comprises an AAV serotype 1 (AAV1) capsid. In some embodiments, the rAAV particle comprises an AAV serotype 2 (AAV2) capsid. In some embodiments, the recombinant AAV viral particle comprises an AAV1, AAV2, AAV8, AAVrh8R, AAV9, and/or AAVrh10 capsid. In some embodiments, the AAV1, AAV2, AAV8, AAVrh8R, AAV9, and/or AAVrh10 capsid comprises a tyrosine mutation or a heparan binding mutation, e.g., as described below. In some embodiments, the capsid is a liver targeting capsid; for example but not limited to, a LK03 capsid, a HSC15 capsid, a 17 capsid, an AAV-XL-32, or an AAV-XL32.1 capsid. In some embodiments, the capsid is an engineered AAV capsid (e.g., a shuffled capsid). Examples of engineered AAV capsids include, but are not limited to DJ (Grimm D et al., *J Virol.* 2008, 82:5887-911), LK03 (Lisowski L et al., *Nature,* 2014, 506:382-6) and HSC15 and HSC17 (Smith U et al., *Mol Ther,* 2014 September; 22(9):1625-34).

The capsid of AAV (e.g., AAV2, AAV8 etc.) is known to include three capsid proteins: VP1, VP2, and VP3. These proteins contain significant amounts of overlapping amino acid sequence and unique N-terminal sequences. An AAV2 capsid includes 60 subunits arranged by icosahedral symmetry (Xie, Q., et al. (2002) *Proc. Natl. Acad. Sci. USA* 99(16):10405-10). VP1, VP2, and VP3 have been found to be present in a 1:1:10 ratio.

In some embodiments, the rAAV particle comprises a) a rAAV capsid comprising rAAV capsid proteins comprising one or more amino acid substitutions at one or more positions that interacts with a heparan sulfate proteoglycan, and b) a rAAV vector comprising the heterologous nucleic acid and at least one AAV inverted terminal repeat.

In some embodiments, the rAAV particles comprise one or more amino acid substitutions of capsid proteins that reduce or ablate binding of the rAAV particle to the heparan sulfate proteoglycan, and/or wherein the one or more amino acid substitutions is at position 484, 487, 532, 585 or 588, numbering based on VP1 numbering of AAV2. As used herein, "numbering based on VP1 of AAV2" refers to the amino acid of the recited capsid protein corresponding to the recited amino acid of VP1 of AAV2. For example, if one or more amino acid substitutions are at position 347, 350, 390, 395, 448, 451, 484, 487, 527, 532, 585 and/or 588, numbering based on VP1 of AAV2, then the one or more amino acid substitutions are at the amino acid(s) of the recited capsid protein corresponding to amino acids 347, 350, 390, 395, 448, 451, 484, 487, 527, 532, 585 and/or 588 of VP1 of AAV2. In some embodiments, the one or more amino acid substitutions is at position 484, 487, 532, 585 or 588 of VP1 of AAV2. In some embodiments, the one or more amino acid substitutions is at position 484, 487, 532, 585 or 588 of VP1 of AAV3, numbering based on VP1 of AAV2. In some embodiments, the one or more amino acid substitutions is at position 485, 488, 528, 533, 586 or 589, numbering based on VP1 numbering of AAVrh8R. In some embodiments, one or more amino acids at position(s) corresponding to amino acids 585 and/or 588 (numbering based on VP1 of AAV2) are replaced by arginine residues (e.g., S586 and/or T589 for AAV1 or AAV6; S586 and/or A589 for AAV9; A586 and/or T589 for AAVrh8R; Q588 and/or T591 for AAV8; and Q588 and/or A591 for AAVrh10). In other embodiments, one or more amino acids (e.g., arginine or lysine) at position(s) corresponding to amino acids 484, 487, 527 and/or 532 (numbering based on VP1 of AAV2) are replaced by non-positively charged amino acid(s) such as alanine (e.g., R485, R488, K528, and/or K533 for AAV1 or AAV6; R485, R488, K528, and/or R533 for AAV9 or AAVrh8R; and R487, R490, K530, and/or R535 for AAV8 or AAVrh10).

XL32 and XL32.1 Capsids and Capsid Proteins

In some embodiments, the AAV particle comprises an engineered AAV capsid. In some embodiments, the engineered AAV capsid is an AAV-XL32 capsid. In some embodiments, the AAV-XL32 capsid comprises an AAV-XL32 capsid protein. In some embodiments, the AAV-XL32 capsid comprises an AAV-XL32 capsid protein comprising an amino acid sequence at least 80%, 85%, 90%, 95%, or 99% identical to SEQ ID NO:3. In some embodiments, the AAV-XL32 capsid comprises a capsid protein encoded by the nucleic acid sequence of SEQ ID NO: 4. In some embodiments, the AAV-XL32 capsid comprises a capsid protein encoded by a nucleic acid that is at least 50%, 55%, 60%, 65%, 70%, 75%, 80%, 85%, 90%, 91%, 92%, 93%, 94%, 95%, 96%, 97%, 98%, or 99% identical to the nucleic acid sequence of SEQ ID NO: 4.

In some embodiments, the AAV particle comprises an AAV-XL32 capsid. In some embodiments, the AAV-XL32 capsid comprises a VP1, a VP2, and a VP3, wherein the VP1, VP2, and VP3 are encoded by the nucleic acid sequence of SEQ ID NO: 4. In some embodiments, the AAV-XL32 capsid comprises a VPX, wherein the VPX is encoded by the nucleic acid sequence of SEQ ID NO: 4. In some embodiments, the AAV-XL32 capsid comprises a capsid protein, wherein the capsid protein is encoded by an open reading frame within the nucleic acid sequence of SEQ ID NO: 4. In some embodiments, the AAV-XL32 capsid comprises one, two, three, or four capsid proteins, wherein the one, two, three, or four capsid proteins are encoded by open reading frames within the nucleic acid sequence of SEQ ID NO: 4.

In some embodiments, the AAV particle comprises an AAV-XL32 capsid protein. In some embodiments, the AAV-XL32 capsid protein comprises an amino acid sequence at least 80%, 85%, 90%, 95%, or 99% identical to SEQ ID NO:3. In some embodiments, the AAV particle comprises a capsid protein encoded by the nucleic acid sequence of SEQ ID NO: 4. In some embodiments, the AAV-XL32 capsid comprises a capsid protein encoded by a nucleic acid that is at least 50%, 55%, 60%, 65%, 70%, 75%, 80%, 85%, 90%, 91%, 92%, 93%, 94%, 95%, 96%, 97%, 98%, or 99% identical to the nucleic acid sequence of SEQ ID NO: 4. In some embodiments, the AAV-XL32 capsid protein is encoded by an open reading frame within the nucleic acid sequence of SEQ ID NO: 4. In some embodiments, the AAV particle comprises one, two, three, or four capsid proteins, wherein the one, two, three, or four capsid proteins are encoded by open reading frames within the nucleic acid sequence of SEQ ID NO: 4. In some embodiments, the AAV viral particle comprises an AAV capsid protein encoded by the nucleic acid sequence of SEQ ID NO: 4. In some embodiments, the AAV particle comprises a VP1, a VP2, and a VP3, wherein the VP1, VP2, and VP3 are encoded by the nucleic acid sequence of SEQ ID NO: 4. In some embodiments, the AAV particle comprises a VPX, wherein the VPX is encoded by the nucleic acid sequence of SEQ ID NO: 4. In some embodiments, the AAV viral particle comprises a VP1, a VP2, a VP3, and a VPX, wherein the VP1, VP2, VP3, and VPX are encoded by the nucleic acid sequence of SEQ ID NO: 4.

In some embodiments, the AAV particle comprises an engineered AAV capsid. In some embodiments, the engineered AAV capsid is an AAV-XL32.1 capsid. In some embodiments, the AAV-XL32.1 capsid comprises an AAV-XL32.1 capsid protein. In some embodiments, the AAV-XL32.1 capsid comprises an AAV-XL32.1 capsid protein comprising an amino acid sequence at least 80%, 85%, 90%, 95%, or 99% identical to SEQ ID NO:3. In some embodiments, the AAV-XL32.1 capsid comprises a capsid protein encoded by the nucleic acid sequence of SEQ ID NO: 6. In some embodiments, the AAV-XL32.1 capsid comprises a capsid protein encoded by a nucleic acid that is at least 50%, 55%, 60%, 65%, 70%, 75%, 80%, 85%, 90%, 91%, 92%, 93%, 94%, 95%, 96%, 97%, 98%, or 99% identical to the nucleic acid sequence of SEQ ID NO: 6.

In some embodiments, the AAV particle comprises an AAV-XL32.1 capsid. In some embodiments, the AAV-XL32.1 capsid comprises a VP1, a VP2, and a VP3, wherein the VP1, VP2, and VP3 are encoded by the nucleic acid sequence of SEQ ID NO: 6. In some embodiments, the AAV-XL32.1 capsid comprises a capsid protein, wherein the capsid protein is encoded by an open reading frame with in the nucleic acid sequence of SEQ ID NO: 6.

In some embodiments, the AAV particle comprises an AAV-XL32.1 capsid protein. In some embodiments, the AAV-XL32.1 capsid protein comprises an amino acid sequence at least 80%, 85%, 90%, 95%, or 99% identical to SEQ ID NO:3. In some embodiments, the AAV particle comprises a capsid protein encoded by the nucleic acid sequence of SEQ ID NO: 6. In some embodiments, the AAV-XL32.1 capsid comprises a capsid protein encoded by a nucleic acid that is at least 50%, 55%, 60%, 65%, 70%, 75%, 80%, 85%, 90%, 91%, 92%, 93%, 94%, 95%, 96%, 97%, 98%, or 99% identical to the nucleic acid sequence of SEQ ID NO: 6. In some embodiments, the AAV-XL32.1 capsid protein is encoded by an open reading frame within the nucleic acid sequence of SEQ ID NO: 6. In some embodiments, the AAV particle comprises one, two, or three capsid proteins, wherein the one, two, or three capsid proteins are encoded by open reading frames within the nucleic acid sequence of SEQ ID NO: 6. In some embodiments, the AAV viral particle comprises an AAV capsid protein encoded by the nucleic acid sequence of SEQ ID NO: 6. In some embodiments, the AAV particle comprises a VP1, a VP2, and a VP3, wherein the VP1, VP2, and VP3 are encoded by the nucleic acid sequence of SEQ ID NO: 6. In some embodiments, the AAV particle comprises one, two, or three capsid proteins, wherein the one, two, or three capsid proteins are encoded by open reading frames within the nucleic acid sequence of SEQ ID NO: 6.

In some embodiments, the AAV particle comprises an AAV capsid described in International Publication No. WO 2019241324 A1. In some embodiments, the AAV particle comprises an AAV capsid protein described in International Publication No. WO 2019241324A1.

Production of AAV Particles

Numerous methods are known in the art for production of rAAV vectors, including transfection, stable cell line production, and infectious hybrid virus production systems which include adenovirus-AAV hybrids, herpesvirus-AAV hybrids (Conway, J E et al., (1997) *J. Virology* 71(11):8780-8789) and baculovirus-AAV hybrids (Urabe, M. et al., (2002) *Human Gene Therapy* 13(16):1935-1943; Kotin, R. (2011) *Hum Mol Genet.* 20(R1): R2-R6). rAAV production cultures for the production of rAAV virus particles all require; 1) suitable host cells, 2) suitable helper virus function, 3) AAV rep and cap genes and gene products; 4) a nucleic acid (such as a therapeutic nucleic acid) flanked by at least one AAV ITR sequences (e.g., an AAV genome encoding a PAH polypeptide); and 5) suitable media and media components to support rAAV production. In some embodiments, the suitable host cell is a primate host cell. In some embodiments, the suitable host cell is a human-derived cell lines such as HeLa, A549, 293, or Perc.6 cells. In some embodiments, the suitable helper virus function is provided by wild-type or mutant adenovirus (such as temperature sensitive adenovirus), herpes virus (HSV), baculovirus, or a plasmid construct providing helper functions. In some embodiments, the AAV rep and cap gene products may be from any AAV serotype. In general, but not obligatory, the AAV rep gene product is of the same serotype as the ITRs of the rAAV vector genome as long as the rep gene products may function to replicated and package the rAAV genome. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors. In some embodiments, the AAV helper functions are provided by adenovirus or HSV. In some embodiments, the AAV helper functions are provided by baculovirus and the host cell is an insect cell (e.g., *Spodoptera frugiperda* (Sf9) cells).

One method for producing rAAV particles is the triple transfection method. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified. As such, in some embodiments, the rAAV particle was produced by triple transfection of a nucleic acid encoding the rAAV vector, a nucleic acid encoding AAV rep and cap, and a nucleic acid encoding AAV helper virus functions into a host cell, wherein the transfection of the nucleic acids to the host cells generates a host cell capable of producing rAAV particles.

In some embodiments, rAAV particles may be produced by a producer cell line method (see Martin et al., (2013) *Human Gene Therapy Methods* 24:253-269; U.S. PG Pub. No. US2004/0224411; and Liu, X. L. et al. (1999) *Gene Ther.* 6:293-299). Briefly, a cell line (e.g., a HeLa, 293, A549, or Perc.6 cell line) may be stably transfected with a plasmid containing a rep gene, a capsid gene, and a vector genome comprising a promoter-heterologous nucleic acid sequence (e.g., a PAH polypeptide). Cell lines may be screened to select a lead clone for rAAV production, which may then be expanded to a production bioreactor and infected with a helper virus (e.g., an adenovirus or HSV) to initiate rAAV production. Virus may subsequently be harvested, adenovirus may be inactivated (e.g., by heat) and/or removed, and the rAAV particles may be purified. As such, in some embodiments, the rAAV particle was produced by a producer cell line comprising one or more of nucleic acid encoding the rAAV vector, a nucleic acid encoding AAV rep and cap, and a nucleic acid encoding AAV helper virus functions. As described herein, the producer cell line method may be advantageous for the production of rAAV particles with an oversized genome, as compared to the triple transfection method.

In some embodiments, the nucleic acid encoding AAV rep and cap genes and/or the rAAV genome are stably maintained in the producer cell line. In some embodiments, nucleic acid encoding AAV rep and cap genes and/or the rAAV genome is introduced on one or more plasmids into a cell line to generate a producer cell line. In some embodiments, the AAV rep, AAV cap, and rAAV genome are introduced into a cell on the same plasmid. In other embodiments, the AAV rep, AAV cap, and rAAV genome are introduced into a cell on different plasmids. In some embodiments, a cell line stably transfected with a plasmid maintains the plasmid for multiple passages of the cell line (e.g., 5, 10, 20, 30, 40, 50 or more than 50 passages of the cell). For example, the plasmid(s) may replicate as the cell replicates, or the plasmid(s) may integrate into the cell genome. A variety of sequences that enable a plasmid to replicate autonomously in a cell (e.g., a human cell) have been identified (see, e.g., Krysan, P. J. et al. (1989) *Mol. Cell Biol.* 9:1026-1033). In some embodiments, the plasmid(s) may contain a selectable marker (e.g., an antibiotic resistance marker) that allows for selection of cells maintaining the plasmid. Selectable markers commonly used in mammalian cells include without limitation blasticidin, G418, hygromycin B, zeocin, puromycin, and derivatives thereof. Methods for introducing nucleic acids into a cell are known in the art and include without limitation viral transduction, cationic transfection (e.g., using a cationic polymer such as DEAE-dextran or a cationic lipid such as LIPOFECTAMINE®), calcium phosphate transfection, microinjection, particle bombardment, electroporation, and nanoparticle transfection (for more details, see e.g., Kim, T. K. and Eberwine, J. H. (2010) *Anal. Bioanal. Chem.* 397:3173-3178).

In some embodiments, the nucleic acid encoding AAV rep and cap genes and/or the rAAV genome are stably integrated into the genome of the producer cell line. In some embodiments, nucleic acid encoding AAV rep and cap genes and/or the rAAV genome is introduced on one or more plasmids into a cell line to generate a producer cell line. In some embodiments, the AAV rep, AAV cap, and rAAV genome are introduced into a cell all on the same plasmid. In other embodiments, the AAV rep, AAV cap, and rAAV genome are introduced into a cell on different plasmids. In some embodiments, the plasmid(s) may contain a selectable marker (e.g., an antibiotic resistance marker) that allows for selection of cells maintaining the plasmid. Methods for stable integration of nucleic acids into a variety of host cell lines are known in the art. For example, repeated selection (e.g., through use of a selectable marker) may be used to select for cells that have integrated a nucleic acid containing a selectable marker (and AAV cap and rep genes and/or a rAAV genome). In other embodiments, nucleic acids may be integrated in a site-specific manner into a cell line to generate a producer cell line. Several site-specific recombination systems are known in the art, such as FLP/FRT (see, e.g., O'Gorman, S. et al. (1991) *Science* 251:1351-1355), Cre/loxP (see, e.g., Sauer, B. and Henderson, N. (1988) *Proc. Natl. Acad. Sci.* 85:5166-5170), and phi C31-att (see, e.g., Groth, A. C. et al. (2000) *Proc. Natl. Acad. Sci.* 97:5995-6000).

In some embodiments, the producer cell line is derived from a primate cell line (e.g., a non-human primate cell line, such as a Vero or FRhL-2 cell line). In some embodiments, the cell line is derived from a human cell line. In some embodiments, the producer cell line is derived from HeLa, 293, A549, or PERC.6® (Crucell) cells. For example, prior to introduction and/or stable maintenance/integration of nucleic acid encoding AAV rep and cap genes and/or the oversized rAAV genome into a cell line to generate a producer cell line, the cell line is a HeLa, 293, A549, or PERC.6® (Crucell) cell line, or a derivative thereof.

In some embodiments, the producer cell line is adapted for growth in suspension. As is known in the art, anchorage-dependent cells are typically not able to grow in suspension without a substrate, such as microcarrier beads. Adapting a cell line to grow in suspension may include, for example, growing the cell line in a spinner culture with a stirring paddle, using a culture medium that lacks calcium and magnesium ions to prevent clumping (and optionally an antifoaming agent), using a culture vessel coated with a siliconizing compound, and selecting cells in the culture (rather than in large clumps or on the sides of the vessel) at each passage. For further description, see, e.g., ATCC frequently asked questions document (available at www.atcc.org/Global/FAQs/9/1/Adapting %20a %20monolayer %20cell %20line %20to %20suspension-40.aspx) and references cited therein.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) a rAAV pro-vector comprising a nucleic acid encoding a heterologous nucleic acid as described herein flanked by at least one AAV ITR, and (iii) an AAV helper function; and (b) recovering the rAAV particles produced by the host cell. In some embodiments, said at least one AAV ITR is selected from the group consisting of AAV1, AAV2, AAV3, AAV4, AAV5, AAV6, AAV7, AAV8, AAVrh8, AAVrh8R, AAV9, AAV10, AAVrh10, AAV11, AAV12, a goat AAV, bovine AAV, or mouse AAV serotype ITRs or the like. For example, in some embodiments, the AAV serotype is AAV1, AAV2, AAV5, AAV6, AAV7, AAV8, AAVrh8, AAVrh8R, AAV9, AAV10, or AAVrh10. In certain embodiments, the nucleic acid in the AAV comprises an AAV2 ITR. In some embodiments, said encapsidation protein is selected from the group consisting of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, goat AAV, AAV1/AAV2 chimeric, bovine AAV, mouse AAV capsid, rAAV2/HBoV1 serotype, AAV-XL32, or AAV-XL32.1 capsid proteins or mutants thereof. In some embodiments, the encapsidation protein is an AAV8 capsid protein. In some embodiments, the rAAV particles comprise an AAV8 capsid and a recombinant genome comprising AAV2 ITRs, and nucleic acid encoding a therapeutic transgene/nucleic acid (e.g., an expression cassette for expressing a PAH polypeptide). In some embodiments, the encapsidation protein is an AAV-XL32 capsid protein. In some embodiments, the encapsidation protein is an AAV-XL32.1 capsid protein.). In some embodiments, the encapsidation protein comprises the amino acid sequence of SEQ ID NO:3.

Suitable rAAV production culture media of the present invention may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles of the invention may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

In some embodiments, the rAAV production culture harvest is clarified to remove host cell debris. In some embodiments, the production culture harvest is clarified by filtration through a series of depth filters including, for example, a grade DOHC Millipore Millistak+HC Pod Filter, a grade A1HC Millipore Millistak+HC Pod Filter, and a 0.2 µm Filter Opticap XL10 Millipore Express SHC Hydrophilic Membrane filter. Clarification can also be achieved by a variety of other standard techniques known in the art, such as, centrifugation or filtration through any cellulose acetate filter of 0.2 µm or greater pore size known in the art.

In some embodiments, the rAAV production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C. for a period of 30 minutes to several hours.

rAAV particles may be isolated or purified using one or more of the following purification steps: equilibrium centrifugation; flow-through anionic exchange filtration; tangential flow filtration (TFF) for concentrating the rAAV particles; rAAV capture by apatite chromatography; heat inactivation of helper virus; rAAV capture by hydrophobic interaction chromatography; buffer exchange by size exclusion chromatography (SEC); nanofiltration; and rAAV capture by anionic exchange chromatography, cationic exchange chromatography, or affinity chromatography. These steps may be used alone, in various combinations, or in different orders. In some embodiments, the method comprises all the steps in the order as described below. Methods to purify rAAV particles are found, for example, in Xiao et al., (1998) Journal of Virology 72:2224-2232; U.S. Pat. Nos. 6,989,264 and 8,137,948; and WO 2010/148143.

Methods of Treatment

Certain aspects of the present disclosure relate to methods of treating phenylketonuria and/or reducing levels of phenylalanine in an individual in need thereof. In some embodiments, the invention provides methods of treating PKU by administering an effective amount of an expression cassette for expressing a PAH polypeptide of the present disclosure. In some embodiments, the PAH polypeptide is a wild type PAH polypeptide. The expression cassette for expressing a PAH polypeptide may be administered to a particular tissue of interest, or it may be administered systemically. In some embodiments, an effective amount of an expression cassette for expressing a PAH polypeptide may be administered parenterally. Parenteral routes of administration may include without limitation intravenous, intraperitoneal, intraosseous, intra-arterial, intracerebral, intramuscular, intrathecal, subcutaneous, intracerebroventricular, intrahepatic, and so forth. In some embodiments, expression of a PAH polypeptide from tissues beyond liver may require the presence of cofactor BH4 (e.g., delivered systemically or co-expressed from nucleic acid) Ding et al., *Mol Ther* 2008, 16:673-681. In some embodiments, an effective amount of an expression cassette for expressing a PAH polypeptide may be administered through one route of administration. In some embodiments, an effective amount of an expression cassette for expressing a PAH polypeptide may be administered through a combination of more than one route of administration. In some embodiments, an effective amount of an expression cassette for expressing a PAH polypeptide is administered to one location. In other embodiments, an effective amount of the expression cassette for expressing a PAH polypeptide may be administered to more than one location. In some embodiments, the expression cassette for expressing a PAH polypeptide is DNA. In some embodiments, the expression cassette for expressing a PAH polypeptide is RNA (e.g., mRNA).

In some embodiments, the invention provides method of decreasing the level of phenylalanine in an individual with PKU by administering an effective amount of an expression cassette for expressing a PAH polypeptide of the present disclosure. In some embodiments, the level of phenylalanine in an individual with PKU following administration of an expression cassette for expressing a PAH polypeptide are decreased to levels found in individuals without PKU. In some embodiments, the level of phenylalanine in individual with PKU following administration of an expression cassette for expressing a PAH polypeptide are decreased by any of about 10%, 20%, 30%, 40%, 50%, 60%, 70%, 80%, 90% or more.

In some embodiments, the invention provides method of decreasing the level of phenylalanine in the blood of an individual with PKU by administering an effective amount of an expression cassette for expressing a PAH polypeptide of the present disclosure. In some embodiments, the level of phenylalanine in the blood of an individual with PKU following administration of an expression cassette for expressing a PAH polypeptide are decreased to levels found in the blood of individuals without PKU. In some embodiments, the level of phenylalanine in the blood of individual with PKU following administration of an expression cassette for expressing a PAH polypeptide are decreased by any of about 10%, 20%, 30%, 40%, 50%, 60%, 70%, 80%, 90% or more.

In some embodiments, the invention provides method of decreasing the level of phenylalanine in the brain of an individual with PKU by administering an effective amount of an expression cassette for expressing a PAH polypeptide of the present disclosure. In some embodiments, the level of phenylalanine in the brain of an individual with PKU following administration of an expression cassette for expressing a PAH polypeptide are decreased to levels found in individuals without PKU. In some embodiments, the level of phenylalanine in the brain of an individual with PKU following administration of an expression cassette for expressing a PAH polypeptide are decreased by any of about 10%, 20%, 30%, 40%, 50%, 60%, 70%, 80%, 90% or more.

In some embodiments, the invention provides method of increasing the level of neurotransmitters in the brain of an individual with PKU by administering an effective amount of an expression cassette for expressing a PAH polypeptide of the present disclosure. In some embodiments, the neurotransmitter is one or more of dopamine, norepinephrine or serotonin. In some embodiments, the levels of neurotransmitters in the brain of an individual with PKU following administration of an expression cassette for expressing a PAH polypeptide are increased to levels found in individuals without PKU.

In some embodiments, the invention provides method of increasing the level of tyrosine and/or typtophan in an individual with PKU by administering an effective amount of an expression cassette for expressing a PAH polypeptide of the present disclosure. In some embodiments, the levels of tyrosine and/or typtophan in an individual with PKU following administration of an expression cassette for expressing a PAH polypeptide are increased to levels found in individuals without PKU.

In some embodiments, the invention provides method of increasing the level of tyrosine and/or typtophan in the blood of an individual with PKU by administering an effective amount of an expression cassette for expressing a PAH polypeptide of the present disclosure. In some embodiments, the levels of tyrosine and/or typtophan in the blood of an individual with PKU following administration of an expression cassette for expressing a PAH polypeptide are increased to levels found in individuals without PKU.

In some embodiments, the invention provides method of increasing the level of tyrosine and/or typtophan in the brain of an individual with PKU by administering an effective amount of an expression cassette for expressing a PAH polypeptide of the present disclosure. In some embodiments, the levels of tyrosine and/or typtophan in the brain of an individual with PKU following administration of an expression cassette for expressing a PAH polypeptide are increased to levels found in individuals without PKU.

In some aspects the invention, an expression cassette for expressing a PAH polypeptide (e.g., a wild type human PAH polypeptide) is delivered to the individual by way of a viral vector. Viral vectors for gene therapy are known in the art. In some aspects, the invention provides methods of treating PKU by administering an effective amount of a lentiviral particle encoding a PAH polypeptide of the present disclosure. In some aspects, the invention provides methods of treating PKU by administering an effective amount of a rAAV particle encoding a PAH polypeptide of the present disclosure. rAAV may be administered to a particular tissue of interest, or it may be administered systemically. In some embodiments, an effective amount of rAAV may be administered parenterally. Parenteral routes of administration may include without limitation intravenous, intraperitoneal, intraosseous, intra-arterial, intracerebral, intramuscular, intrathecal, subcutaneous, intracerebroventricular, intrahepatic, and so forth. In some embodiments, an effective amount of rAAV may be administered through one route of administration. In some embodiments, an effective amount of rAAV may be administered through a combination of more than one route of administration. In some embodiments, an effective amount of rAAV is administered to one location. In other embodiments, an effective amount of rAAV may be administered to more than one location.

An effective amount of rAAV (in some embodiments in the form of particles) is administered, depending on the objectives of treatment. For example, where a low percentage of transduction can achieve the desired therapeutic effect, then the objective of treatment is generally to meet or exceed this level of transduction. In some instances, this level of transduction can be achieved by transduction of only about 1 to 5% of the target cells of the desired tissue type, in some embodiments at least about 20% of the cells of the desired tissue type, in some embodiments at least about 50%, in some embodiments at least about 80%, in some embodiments at least about 95%, in some embodiments at least about 99% of the cells of the desired tissue type. The rAAV composition may be administered by one or more administrations, either during the same procedure or spaced apart by days, weeks, months, or years. One or more of any of the routes of administration described herein may be used. In some embodiments, multiple vectors may be used to treat the human.

Methods to identify cells transduced by AAV viral particles are known in the art; for example, immunohistochemistry or the use of a marker such as enhanced green fluorescent protein can be used to detect transduction of viral particles; for example viral particles comprising a rAAV capsid with one or more substitutions of amino acids.

In some embodiments, an effective amount of rAAV particles is administered to more than one location simultaneously or sequentially. In other embodiments, an effective amount of rAAV particles is administered to a single location more than once (e.g., repeated). In some embodiments, multiple injections of rAAV viral particles are no more than one hour, two hours, three hours, four hours, five hours, six hours, nine hours, twelve hours or 24 hours apart.

In some embodiments, the invention provides a method for treating a human with PKU by administering an effective amount of a pharmaceutical composition comprising a recombinant viral vector encoding a PAH polypeptide of the present disclosure. In some embodiments, the pharmaceutical composition comprises one or more pharmaceutically acceptable excipients.

In some embodiments, the methods comprise administering an effective amount of a pharmaceutical composition comprising a recombinant viral vector encoding a PAH polypeptide of the present disclosure to treat PKU in an individual in need thereof. In some embodiments, the viral titer of the viral particles (e.g., rAAV particles) is at least about any of $5\times10^{12}$, $6\times10^{12}$, $7\times10^{12}$, $8\times10^{12}$, $9\times10^{12}$, $10\times10^{12}$, $11\times10^{12}$, $15\times10^{12}$, $20\times10^{12}$, $25\times10^{12}$, $30\times10^{12}$ or $50\times10^{12}$ genome copies/mL. In some embodiments, the viral titer of the viral particles (e.g., rAAV particles) is about any of $5\times10^{12}$ to $6\times10^{12}$, $6\times10^{12}$ to $7\times10^{12}$, $7\times10^{12}$ to $8\times10^{12}$, $8\times10^{12}$ to $9\times10^{12}$, $9\times10^{12}$ to $10\times10^{12}$, $10\times10^{12}$ to $11\times10^{12}$, $11\times10^{12}$ to $15\times10^{12}$, $15\times10^{12}$ to $20\times10^{12}$, $20\times10^{12}$ to $25\times10^{12}$, $25\times10^{12}$ to $30\times10^{12}$, $30\times10^{12}$ to $50\times10^{12}$, or $50\times10^{12}$ to $100\times10^{12}$ genome copies/mL. In some embodiments, the viral titer of the viral particles (e.g., rAAV particles) is about any of $5\times10^{12}$ to $10\times10^{12}$, $10\times10^{12}$ to $25\times10^{12}$, or $25\times10^{12}$ to $50\times10^{12}$ genome copies/mL. In some embodiments, the viral titer of the viral particles (e.g., rAAV particles) is at least about any of $5\times10^{9}$, $6\times10^{9}$, $7\times10^{9}$, $8\times10^{9}$, $9\times10^{9}$, $10\times10^{9}$, $11\times10^{9}$, $15\times10^{9}$, $20\times10^{9}$, $25\times10^{9}$, $30\times10^{9}$, or $50\times10^{9}$ transducing units/mL. In some embodiments, the viral titer of the viral particles (e.g., rAAV particles) is about any of $5\times10^{9}$ to $6\times10^{9}$, $6\times10^{9}$ to $7\times10^{9}$, $7\times10^{9}$ to $8\times10^{9}$, $8\times10^{9}$ to $9\times10^{9}$, $9\times10^{9}$ to $10\times10^{9}$, $10\times10^{9}$ to $11\times10^{9}$, $11\times10^{9}$ to $15\times10^{9}$, $15\times10^{9}$ to $20\times10^{9}$, $20\times10^{9}$ to $25\times10^{9}$, $25\times10^{9}$ to $30\times10^{9}$, $30\times10^{9}$ to $50\times10^{9}$ or $50\times10^{9}$ to $100\times10^{9}$ transducing units/mL. In some embodiments, the viral titer of the viral particles (e.g., rAAV particles) is about any of $5\times10^{9}$ to $10\times10^{9}$, $10\times10^{9}$ to $15\times10^{9}$, $15\times10^{9}$ to $25\times10^{9}$, or $25\times10^{9}$ to $50\times10^{9}$ transducing units/mL. In some embodiments, the viral titer of the viral particles (e.g., rAAV particles) is at least any of about $5\times10^{10}$, $6\times10^{10}$, $7\times10^{10}$, $8\times10^{10}$, $9\times10^{10}$, $10\times10^{10}$, $11\times10^{10}$, $15\times10^{10}$, $20\times10^{10}$, $25\times10^{10}$, $30\times10^{10}$, $40\times10^{10}$, or $50\times10^{10}$ infectious units/mL. In some embodiments, the viral titer of the viral particles (e.g., rAAV particles) is at least any of about $5\times10^{10}$ to $6\times10^{10}$, $6\times10^{10}$ to $7\times10^{10}$, $7\times10^{10}$ to $8\times10^{10}$, $8\times10^{10}$ to $9\times10^{10}$, $9\times10^{10}$ to $10\times10^{10}$, $10\times10^{10}$ to $11\times10^{10}$, $11\times10^{10}$ to $15\times10^{10}$, $15\times10^{10}$ to $20\times10^{10}$, $20\times10^{10}$ to $25\times10^{10}$, $25\times10^{10}$ to $30\times10^{10}$, $30\times10^{10}$ to $40\times10^{10}$, $40\times10^{10}$ to $50\times10^{10}$, or $50\times10^{10}$ to $100\times10^{10}$ infectious units/mL. In some embodiments, the viral titer of the viral particles (e.g., rAAV particles) is at least any of about $5\times10^{10}$ to $10\times10^{10}$, $10\times10^{10}$ to $15\times10^{10}$, $15\times10^{10}$ to $25\times10^{10}$, or $25\times10^{10}$ to $50\times10^{10}$ infectious units/mL. In some embodiments, the viral particles are rAAV particles. In some embodiments, the rAAV particles comprise an XL32 capsid. In some embodiments, the rAAV particles comprise an XL32.1 capsid.

In some embodiments, the dose of viral particles administered to the individual is at least about any of $1\times10^{8}$ to about $6\times10^{13}$ genome copies/kg of body weight. In some embodiments, the dose of viral particles administered to the individual is about any of $1\times10^{8}$ to about $6\times10^{13}$ genome copies/kg of body weight. In some embodiments, the dose of viral particles administered to the individual is about any of $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $13\times10^{12}$, $4\times10^{12}$, $5\times10^{12}$, $6\times10^{12}$, $7\times10^{12}$, $8\times10^{12}$, $9\times10^{12}$, or $1\times10^{13}$ genome copies/kg of body weight.

In some embodiments, the total amount of viral particles administered to the individual is at least about any of $1\times10^{9}$ to about $1\times10^{14}$ genome copies. In some embodiments, the total amount of viral particles administered to the individual is about any of $1\times10^{9}$ to about $1\times10^{14}$ genome copies. In some embodiments, the total amount of viral particles administered to the individual is about any of $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $13\times10^{13}$, $4\times10^{13}$, $5\times10^{13}$, $6\times10^{13}$, $7\times10^{13}$, $8\times10^{13}$, $9\times10^{13}$, or $1\times10^{14}$ genome copies.

Compositions of the invention (e.g., recombinant viral particles comprising a vector encoding a PAH polypeptide of the present disclosure) can be used either alone or in combination with one or more additional therapeutic agents for treating PKU. The interval between sequential administration can be in terms of at least (or, alternatively, less than) minutes, hours, or days.

An effective amount of rAAV (in some embodiments in the form of particles) is administered, depending on the objectives of treatment. For example, where a low percentage of transduction can achieve the desired therapeutic effect, then the objective of treatment is generally to meet or exceed this level of transduction. In some instances, this level of transduction can be achieved by transduction of only about 1 to 5% of the target cells, in some embodiments at least about 20% of the cells of the desired tissue type, in some embodiments at least about 50%, in some embodiments at least about 80%, in some embodiments at least about 95%, in some embodiments at least about 99% of the cells of the desired tissue type. The rAAV composition may be administered by one or more administrations, either during the same procedure or spaced apart by days, weeks, months, or years. In some embodiments, multiple vectors may be used to treat the mammal (e.g., a human).

In some embodiments, a rAAV composition of the present disclosure may be used for administration to a human. In some embodiments, a rAAV composition of the present disclosure may be used for pediatric administration. Without wishing to be bound to theory, because many of the symptoms of PKU are developmental in nature (e.g., severe mental disorders), it may be particularly advantageous to treat PKU as early in life as possible. In some embodiments, an effective amount of rAAV (in some embodiments in the form of particles) is administered to a patient that is less than one month, less than two months, less than three months, less than four months, less than five months, less than six months, less than seven months, less than eight months, less than nine months, less than ten months, less than eleven months, less than one year, less than 13 months, less than 14 months, less than 15 months, less than 16 months, less than 17 months, less than 18 months, less than 19 months, less than 20 months, less than 21 months, less than 22 months, less than two years, or less than three years old.

In some embodiments, a rAAV composition of the present disclosure may be used for administration to a young adult. In some embodiments, an effective amount of rAAV (in some embodiments in the form of particles) is administered to a patient that is less than 12 years old, less than 13 years old, less than 14 years old, less than 15 years old, less than 16 years old, less than 17 years old, less than 18 years old, less than 19 years old, less than 20 years old, less than 21 years old, less than 22 years old, less than 23 years old, less than 24 years old, or less than 25 years old.

In some embodiments, the invention provides methods of treating PKU by administering an effective amount of cells comprising an expression cassette for expressing a PAH polypeptide (e.g., a wild type human PAH polypeptide) of the present disclosure. The cells comprising the expression cassette for expressing a PAH polypeptide may be administered to a particular tissue of interest, or it may be administered systemically. In some embodiments, an effective amount of cells comprising the expression cassette for expressing a PAH polypeptide may be administered parenterally. Parenteral routes of administration may include without limitation intravenous, intraperitoneal, intraosseous, intra-arterial, intracerebral, intramuscular, intrathecal, subcutaneous, intracerebroventricular, intrahepatic, and so forth. In some embodiments, the cells are encapsulated or in a device. In some embodiments, the PAH expressing cells outside liver may require exogenously added or co-expressed cofactor BH4. In some embodiments, the cells are encapsulated or in a device which further comprises BH4. In some embodiments, an effective amount of cells comprising expression cassette for expressing a PAH polypeptide may be administered through one route of administration. In some embodiments, an effective amount of expression cassette for expressing a PAH polypeptide may be administered through a combination of more than one route of administration. In some embodiments, an effective amount of the expression cassette for expressing a PAH polypeptide is administered to one location. In other embodiments, an effective amount of the expression cassette for expressing a PAH polypeptide may be administered to more than one location.

In some embodiments, the cell comprising an expression cassette for expressing a PAH polypeptide is a hepatocyte, a muscle cell, fibroblast, an endothelial cell, an epithelial cell, a blood cell, a bone marrow cell, a stem cell, or an induced pluripotent stem cell. In some embodiments, the cell further comprises exogenously added cofactor BH4 and/or coexpressed cofactor BH4.

In some embodiments, the cell is a cell line (e.g., a CHO cell line, a HeLa cell line, etc.). In some embodiments, the invention provides methods to produce a PAH polypeptide (e.g., a wild type human PAH polypeptide) comprising culturing a cell comprising an expression cassette encoding a PAH polypeptide under conditions to produce the PAH polypeptide. In some embodiments, the method to produce a PAH polypeptide further comprises one or more steps of purifying the PAH polypeptide.

Kits or Articles of Manufacture

The expression cassettes (e.g., an expression cassette for expressing a PAH polypeptide, such as a wild type human PAH polypeptide), rAAV vectors, particles, and/or pharmaceutical compositions as described herein may be contained within a kit or article of manufacture, e.g., designed for use in one of the methods of the invention as described herein.

Generally, the system comprises a cannula, one or more syringes (e.g., 1, 2, 3, 4 or more), and one or more fluids (e.g., 1, 2, 3, 4 or more) suitable for use in the methods of the invention.

The syringe may be any suitable syringe, provided it is capable of being connected to the cannula for delivery of a fluid. In some embodiments, the system has one syringe. In some embodiments, the system has two syringes. In some embodiments, the system has three syringes. In some embodiments, the system has four or more syringes. The fluids suitable for use in the methods of the invention include those described herein, for example, one or more fluids each comprising an effective amount of one or more vectors as described herein, and one or more fluids comprising one or more therapeutic agents.

In some embodiments, the kit comprises a single fluid (e.g., a pharmaceutically acceptable fluid comprising an effective amount of the vector). In some embodiments, the kit comprises 2 fluids. In some embodiments, the kit comprises 3 fluids. In some embodiments, the kit comprises 4 or more fluids. A fluid may include a diluent, buffer, excipient, or any other liquid described herein or known in the art suitable for delivering, diluting, stabilizing, buffering, or otherwise transporting an expression cassette for expressing a PAH polypeptide or rAAV vector composition of the present disclosure. In some embodiments, the kit comprises one or more buffers, e.g., an aqueous pH buffered solution. Examples of buffers may include without limitation phosphate, citrate, Tris, HEPES, and other organic acid buffers.

In some embodiments, the kit comprises a container. Suitable containers may include, e.g., vials, bags, syringes, and bottles. The container may be made of one or more of a material such as glass, metal, or plastic. In some embodiments, the container is used to hold a rAAV composition of the present disclosure. In some embodiments, the container may also hold a fluid and/or other therapeutic agent.

In some embodiments, the kit comprises an additional therapeutic agent with a rAAV composition of the present disclosure. In some embodiments, the rAAV composition and the additional therapeutic agent may be mixed. In some embodiments, the rAAV composition and the additional therapeutic agent may be kept separate. In some embodiments, the rAAV composition and the additional therapeutic agent may be in the same container. In some embodiments, the rAAV composition and the additional therapeutic agent may be in different containers. In some embodiments, the rAAV composition and the additional therapeutic agent may be administered simultaneously. In some embodiments, the rAAV composition and the additional therapeutic agent may be administered on the same day. In some embodiments, the rAAV composition may be administered within one day, two days, three days, four days, five days, six days, seven days, two weeks, three weeks, four weeks, two months, three months, four months, five months, or six months of administration of the additional therapeutic agent.

In some embodiments, the kit comprises a therapeutic agent to transiently suppress the immune system prior to AAV administration. In some embodiments, patients are transiently immune suppressed shortly before and after injection of the virus to inhibit the T cell response to the AAV particles (e.g., see Ferreira et al., *Hum. Gene Ther.* 25:180-188, 2014). In some embodiments, the kit further provides cyclosporine, mycophenolate mofetil, and/or methylprednisolone.

The rAAV particles and/or compositions of the invention may further be packaged into kits including instructions for use. In some embodiments, the kits further comprise a device for delivery (e.g., any type of parenteral administration described herein) of compositions of rAAV particles. In some embodiments, the instructions for use include instructions according to one of the methods described herein. In some embodiments, the instructions are printed on a label provided with (e.g., affixed to) a container. In some embodiments, the instructions for use include instructions for administering to an individual (e.g., a human) an effective amount of rAAV particles, e.g., for treating PKU in an individual.

EXEMPLARY EMBODIMENTS

Embodiment 1. A recombinant adeno-associated virus (rAAV) particle comprising an rAAV vector, wherein the rAAV vector comprises an expression cassette for expressing a transgene in a liver cell, wherein the expression cassette comprises a transgene operably linked to a promoter and enhancer, wherein the promoter comprises a mouse transthyretin (mTTR) promoter and the enhancer comprises one or two modified prothrombin enhancers (pPrT2), one or two modified alpha1-microbikunin enhancers (mA1MB2), a modified mouse albumin enhancer (mEalb), a hepatitis B virus enhancer II (HEII) or a CRM8 enhancer, wherein the transgene encodes a PAH polypeptide; wherein the AAV viral particle comprises an AAV-XL32 or an AAV-XL32.1 capsid.

Embodiment 2. The rAAV particle of embodiment 1, wherein the mTTR promoter is a mTTR482 promoter.

Embodiment 3. The rAAV particle of embodiment 1 or 2, wherein the enhancer is 5' to the mTTR promoter.

Embodiment 4. A recombinant adeno-associated virus (rAAV) particle comprising an rAAV vector, wherein the rAAV vector comprises an expression cassette for expressing a transgene in a liver cell, wherein the expression cassette comprises a transgene operably linked to a promoter and a 3' element, wherein the promoter comprises a mouse transthyretin (mTTR) promoter and the 3' element is an albumin 3' element (3'Alb) or an albumin 3' element linked to a human alpha 1 antitrypsin scaffold/matrix attachment region (SMAR) (3'AlbSMAR), wherein the transgene encodes a PAH polypeptide; wherein the AAV viral particle comprises an AAV-XL32 or an AAV-XL32.1 capsid.

Embodiment 5. The rAAV particle of embodiment 4, wherein the mTTR promoter is a mTTR482 promoter.

Embodiment 6. The rAAV particle of embodiment 4 or 5, wherein the 3' element is located 3' to the transgene.

Embodiment 7. A recombinant adeno-associated virus (rAAV) particle comprising an rAAV vector, expression cassette for expressing a transgene in a liver cell, wherein the expression cassette comprises a transgene operably linked to a promoter and enhancer and a 3' element, wherein the promoter comprises a mouse transthyretin (mTTR) promoter and the enhancer comprises one or two modified prothrombin enhancers (pPrT2), one or two modified alpha1-microbikunin enhancers (mA1MB2), a modified mouse albumin enhancer (mEalb), a hepatitis B virus enhancer II (HEII) or a CRM8 enhancer; and wherein the 3' element is an albumin 3' element (3'Alb) or an albumin 3' element linked to a human alpha 1 antitrypsin scaffold/matrix attachment region (SMAR) (3'AlbSMAR), wherein the transgene encodes a PAH polypeptide; wherein the AAV viral particle comprises an AAV-XL32 or an AAV-XL32.1 capsid.

Embodiment 8. The rAAV particle of embodiment 7, wherein the mTTR promoter is a mTTR482 promoter.

Embodiment 9. The rAAV particle of embodiment 7 or 8, wherein the enhancer is 5' to the mTTR promoter.

Embodiment 10. The rAAV particle of any one of embodiments 7-9, wherein the 3' element is located 3' to the transgene.

Embodiment 11. The rAAV particle of any one of embodiments 1-10, wherein the expression cassette further comprises an intron.

Embodiment 12. The rAAV particle of embodiment 11, wherein the intron is a chicken β-actin/rabbit β-globin hybrid intron.

Embodiment 13. The rAAV particle of any one of embodiments 1-12, wherein the expression cassette further comprises a polyadenylation signal.

Embodiment 14. The rAAV particle of embodiment 13, wherein the polyadenylation signal is a bovine growth hormone polyadenylation signal.

Embodiment 15. The rAAV particle of any one of embodiments 1-14, wherein the PAH polypeptide is a wild type PAH polypeptide.

Embodiment 16. The rAAV particle of any one of embodiments 1-15, wherein the PAH polypeptide is a human PAH polypeptide.

Embodiment 17. The rAAV particle of any one of embodiments 1-16, wherein the PAH polypeptide comprises the amino acid sequence of SEQ ID NO:1.

Embodiment 18. The rAAV particle of any one of embodiments 1-17, wherein the transgene is at least 80% identical to the nucleic acid sequence of SEQ ID NO:2.

Embodiment 19. The rAAV particle of any one of embodiments 1-18, wherein the rAAV vector comprises the expression cassette flanked by one or more AAV inverted terminal repeat (ITR) sequences.

Embodiment 20. The rAAV particle of embodiment 19, wherein the expression cassette of any one of embodiments 1-18 is flanked by two AAV ITRs.

Embodiment 21. The rAAV particle of embodiment 19 or 20, wherein the AAV ITRs are AAV ITRs are AAV1, AAV2, AAV3, AAV4, AAV5, AAV6, AAV7, AAV8, AAVrh8, AAVrh8R, AAV9, AAV10, AAVrh10, AAV 11, AAV12, AAV2R471A, AAV DJ, a goat AAV, bovine AAV, or mouse AAV serotype ITRs.

Embodiment 22. The rAAV particle of any one of embodiments 19-21, wherein the AAV ITRs are AAV2 ITRs.

Embodiment 23. The rAAV particle of any one of embodiments 19-22, wherein the vector is a self-complimenting vector.

Embodiment 24. The rAAV particle of embodiment 23, wherein the vector comprises first nucleic acid sequence encoding the PAH polypeptide and a second nucleic acid sequence encoding a complement of the PAH polypeptide, wherein the first nucleic acid sequence can form intrastrand base pairs with the second nucleic acid sequence along most or all of its length.

Embodiment 25. The rAAV particle of embodiment 24, wherein the first nucleic acid sequence and the second nucleic acid sequence are linked by a mutated AAV ITR, wherein the mutated AAV ITR comprises a deletion of the D region and comprises a mutation of the terminal resolution sequence.

Embodiment 26. An rAAV particle comprising an rAAV vector, wherein the rAAV vector comprises 5' to 3' an AAV2 ITR, a modified alpha1-microbikunin enhancer (mA1MB2), a mouse transthyretin (mTTR) promoter, a chicken β-actin/rabbit β-globin hybrid intron, a codon-optimized human PAH gene, a bovine growth hormone polyadenylation signal, a stuffer fragment derived from an alpha-1-antitrypsin gene and an AAV2 ITR.

Embodiment 27. The rAAV particle of any one of embodiments 1-26, wherein the AAV capsid is an AAV-XL32 capsid.

Embodiment 28. The rAAV particle of embodiment 27, wherein the AAV-XL32 capsid comprises an AAV-XL32 capsid protein comprising an amino acid sequence at least 90%, 95%, 99% or 100% identical to SEQ ID NO:3.

Embodiment 29. The rAAV particle of embodiment 28, wherein the AAV-XL32 capsid comprises a VP1, a VP2, and a VP3, wherein the VP1, VP2, and VP3 are encoded by the nucleic acid sequence of SEQ ID NO: 4.

Embodiment 30. The rAAV particle of any one of embodiments 1-26, wherein the AAV capsid is an AAV-XL32.1 capsid.

Embodiment 31. The rAAV particle of embodiment 30, wherein the AAV-XL32.1 capsid comprises an amino acid sequence at least 90%, 95%, 99%, or 100% identical to SEQ ID NO:3.

Embodiment 32. The rAAV particle of embodiment 30, wherein the AAV-XL32.1 capsid comprises a VP1, a VP2, and a VP3, wherein the VP1, VP2, and VP3 are encoded by the nucleic acid sequence of SEQ ID NO: 6.

Embodiment 33. A composition comprising the rAAV particle of any one of embodiments 1-32.

Embodiment 34. The composition of embodiment 33, wherein the composition further comprises a pharmaceutically acceptable carrier.

Embodiment 35. A cell comprising the rAAV particle of any one of embodiments 1-32.

Embodiment 36. A method of producing a PAH polypeptide, the method comprising culturing the cell of embodiment 35 under conditions to produce the PAH polypeptide.

Embodiment 37. The method of embodiment 36, further comprising the step of purifying the PAH polypeptide.

Embodiment 38. A method for treating phenylketonuria in an individual in need thereof, comprising administering to the individual the rAAV particle of any one of embodiments 1-37.

Embodiment 39. A method for treating phenylketonuria in an individual in need thereof, comprising administering to the individual the composition of embodiment 33 or 34.

Embodiment 40. A method for treating phenylketonuria in an individual in need thereof, comprising administering to the individual the cell of embodiment 35.

Embodiment 41. The method of any one of embodiments 38-40, wherein the individual lacks PAH activity.

Embodiment 42. A method for reducing the level of phenylalanine in the blood of in an individual in need thereof, comprising administering to the individual the rAAV particle of any one of embodiments 1-32.

Embodiment 43. A method for reducing the level of phenylalanine in the blood of in an individual in need thereof, comprising administering to the individual the composition of embodiment 33 or 34.

Embodiment 44. A method for reducing the level of phenylalanine in the blood of in an individual in need thereof, comprising administering to the individual the cell of embodiment 35.

Embodiment 45. The method of any one of embodiments 42-44, wherein the level of phenylalanine in the blood of the individual prior to treatment is elevated compared to the level of phenylalanine in the blood of peer-matched control individuals.

Embodiment 46. The method of any one of embodiments 38-45, wherein the rAAV particle, composition or cell is administered intravenously, intraarterially, intrahepatically, intraportally, intraperitoneally, or subcutaneously.

Embodiment 47. The method of any one of embodiments 38-46, wherein the administration is in combination with another therapy.

Embodiment 48. The method of embodiment 47, wherein the another therapy is treatment with tetrahydribiopterin, treatment with phenylalanine ammonia lyase (PAL) or pegylated PAL, or a phenylalanine-restricted diet.

Embodiment 49. A kit comprising the rAAV particle of any one of embodiments 1-32, the composition of embodiment 33 or 34, or the cell of embodiment 35.

Embodiment 50. The kit of embodiment 49, wherein the kit further comprises instructions for use; buffers and/or pharmaceutically acceptable excipients; and/or bottles, vials and/or syringes.

EXAMPLES

The invention will be more fully understood by reference to the following examples. They should not, however be construed as limiting the scope of the invention. It is understood that the examples and embodiments described herein are for illustrative purposes only and that various modification or changes in light thereof will be suggested to persons skilled in the art and are to be included within the spirit and purview of this application and scope of the appended embodiments.

Example 1. In Vitro Evaluation of PAH Coding Sequences

The following example describes the generation of vectors encoding human PAH. Specifically, wild type and variant PAH alleles with or without an E183G amino acid substitution were cloned into a vector, and PAH expression and activity in liver cells was measured.

Materials and Methods

PAH Coding Sequences

Human PAH cDNAs encoding wild type or variant 1 PAH with or without an E183G amino acid substitution were tested, as summarized in Table 1, below. The "variant 1" allele of PAH has M180T, K199P, S250P and G256A amino acid substitutions, as described in International Publication No. WO2020077250A1, incorporated herein by reference.

GeneArt (GA) codon optimization was used to optimize the codon usage of the PAH cDNAs.

TABLE 1

Summary of PAH coding sequences tested

| PAH coding sequence | Description |
|---|---|
| hPAH/E (also known as, "WT PAH") | Wild type human PAH<br>Amino acid sequence: SEQ ID NO: 1<br>Nucleic acid coding sequence: SEQ ID NO: 2 |
| hPAH/183G | Human PAH with E183G amino acid substitution |
| hPAH-V1/G | Human PAH variant 1 with E183G amino acid substitution (M180T, E183G, K199P, S250P and G256A) |
| hPAH-V1/E | Human PAH variant 1 (M180T, K199P, S250P and G256A) |

Plasmid Vectors and Recombinant AAVgeneration

PAH coding sequences were expressed described in International Publication No. WO2020077250A1, incorporated herein by reference.

Specifically, to increase liver promoter strength, modifications were introduced into the plasmid mTTR482-HI-hFVIII-BGHpA, containing a mouse transthyretin (mTTR) promoter, an endogenous mTTR enhancer and a bovine growth hormone (BGH) polyadenylation (pA) site (Kyostio-Moore 2016, Nambiar 2017). In this plasmid, the FVIII cDNA was replaced with cDNA encoding secreted embryonic alkaline phosphatase (SEAP) and existing intron was replaced with a 1069 bp chicken b-actin (CBA)/rabbit beta-globin hybrid intron. Two copies of a modified alpha1-microbikunin enhancer (mA1MB2) (McEachern 2006, Jacobs 2008), were cloned upstream of the mTTR482 enhancer to generate a mA1MB2-mTTR482 promoter.

A hybrid intron made of a chicken beta-actin/rabbit beta-globin intron, modified to eliminate five existing ATG sequences to diminish false translation starts was used (also known as HI2).

All vectors contained bovine growth hormone polyadenylation site (BGHpA).

Lastly, a filler sequence ("stuffer") consisting of alpha-antitrypsin gene intron sequence (SerpinA1=A1AT) chromosome 14 NG_008290.1; nt13638-17363) was included between the BGHpA and ITR site to bring the total vector genome size to 4.6 kb. Seven ATG sites in the stuffer sequence were modified to TTG to remove potential translation start sites.

Several AAV2 ITR containing plasmids with liver promoter, hybrid intron, PAH cDNA and BGHpA were used for rAAV vector production. rAAV vectors with AAVXL32 serotype capsid were generated using triple transfection method followed by CsCl purification (SabTech) or by column purification (Sanofi Vector Core). Vector lots were quantitated by qPCR to BGHpA (Nambiar 2017).

In Vitro Cultures

All tissue culture reagents were obtained from Irvine Scientific (Santa Ana, CA) or Invitrogen. For transient transfection, human 293 or human liver carcinoma cells (Huh7 or HepG2) ($8 \times 10^5$ cells/well) were plated on 6-well dishes in Dulbecco's modified Eagle's medium (DMEM) with high glucose, 10% fetal bovine serum (FBS) and 10 ml/L Pen Strep (10 units/ml penicillin and 10 µg/ml streptomycin). Plasmids (2 µg) were transfected with LIPOFECTAMINE® 2000 (Invitrogen). Cell lysates or culture media were harvested for PAH analysis or SEAP activity, respectively, 48 or 72 hours later.

Activity Assays and Protein Detection

To measure PAH activity, whole cell lysates were generated 48 hours later by lysing cells in lysis buffer or in RIPA buffer. Additionally, sonication or shearing was used to enhance cell lysis in some experiments. Upon thawing, lysates were spun at 14,000 g for 30 minutes before assays. The enzyme activity of PAH proteins was measured as previously described in Yew et al. 2013 with some minor modifications. The activity was also measured using 13C-labeled Phe as previously described (Heintz 2012).

Western blotting for PAH detection was performed using anti-hPAH antibody (LS-C344145; LSBio) using standard protocols. In vivo samples were normalized by total protein content measured by BCA protein assay kit (Pierce). Quantitation of FLAG-PAH protein levels were measured by FLAG ELISA (SE002-flag; ABSbio) according to manufacturer's instructions and using either kit standard or in-house purified 3×FLAG-mPAH-FL as protein standard.

Results

Four vectors encoding PAH under control of the mA1MB2-mTTR482 were generated. Specifically, hPAH/183G, hPAH-V1/G, hPAH-V1/E and wild type PAH ("hPAH/E") were expressed and tested for PAH activity (FIG. 1A) and protein levels (FIG. 1B, 1C) in Huh7 cells.

Figure 1B:
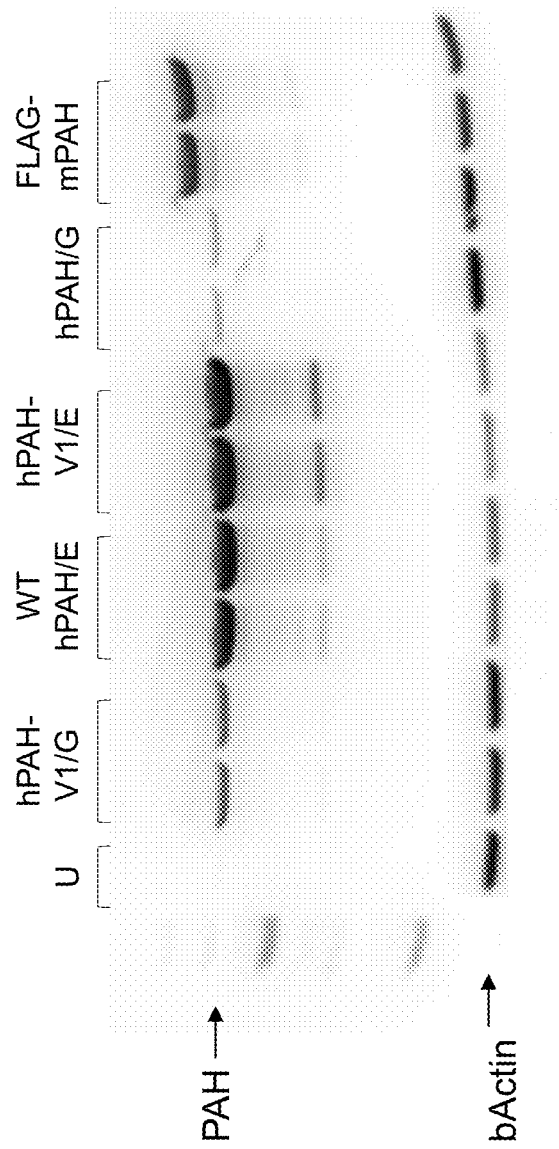
Figure 1C:
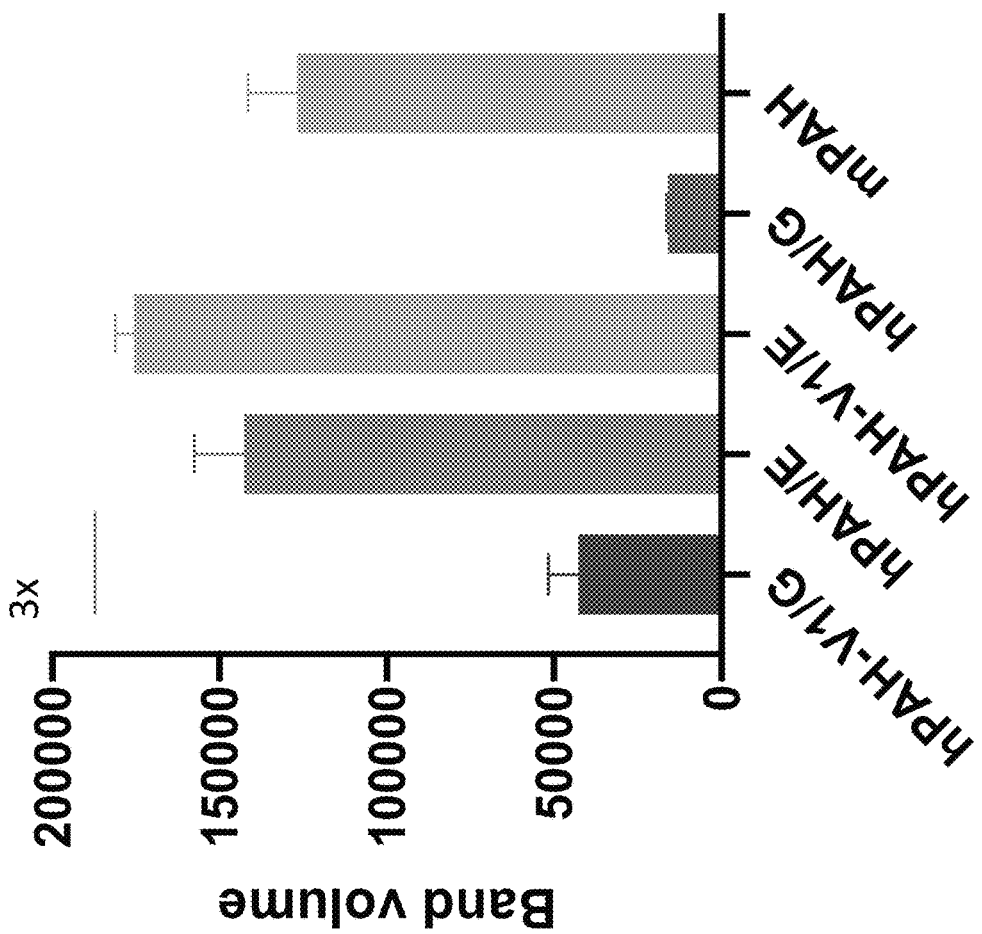

Wild type PAH demonstrated the highest level of PAH activity, as shown in FIG. 1A. For the hPAH/G mutant coding sequence, the addition of the variant 1 four amino acid substitutions improved activity and protein production by 10-fold. Incorporating the variant 1 four amino acid substitutions into the wild type PAH coding sequence did not increase PAH activity but did result in 2-fold increase in PAH protein levels (FIG. 1B, 1C).

Based on these results, wild type PAH was selected as the transgene for in vivo efficacy studies in Pah-KO mice.

Example 2. Evaluation of Capsids, Lead Liver Promoter and Dose-Responsiveness in Non-Human Primate Livers The following example describes experiments assessing the ability of various AAV capsid proteins to transduce liver cells. Further, the ability of the mA1M2-mTTR482 promoter to promote transgene expression in non-human primates (NHPs) was tested, and a dose-response experiment was performed to assess administration of the XL32.1/mA1MB2-mTTR482-EGFP vector to NHPs.

Materials and Methods

AAV Capsid Proteins

Various AAV capsid proteins were tested for their ability to transduce Huh7 cells and non-human primate (NHP) livers. Specifically, XL32, LK03 (Lisowski L et al., Nature, 2014, 506:382-6), DJ (Grimm D, et al. J Virol 2008, 82:5887-5911), AAV8, and XL14 capsid proteins were tested in initial experiments in Huh7 cells and NHPs (FIGS. 2A-2D). In a subsequent dose-response experiment in NHPs, XL32.1 capsid protein was used (FIGS. 3A-3B, 4A-4C).

As described in International Publication No. WO 2019241324 A1, XL32 and XL32.1 are hybrid capsids that were generated from an AAV capsid gene shuffle library made up of the capsid genes of AAV serotypes 1, 2, 3B, 4, 6, 7, 8, and 9. XL32 was selected from the library due to its enrichment in the mouse liver. In addition to the typical VP1, VP2, and VP3 protein products, XL32 also produced a fourth protein product (termed "VPX") that was thought to be produced due to a weak, non-ATG start codon within the XL32 coding sequence. Specifically, XL32 had a C to G mutation at nucleotide 219 counting from the VP1 start codon. XL32.1 was derived from XL32 by site-directed mutagenesis to reverse the C to G mutation back to the original C, to match wild type AAV7 and AAV8 sequences. According to International Publication No. WO 2019241324 A1, XL32.1 did not show an apparent differences in vector yield and infectivity. The amino acid sequences of XL32 and XL32.1 are provided in Table 2, below.

TABLE 2

XL32 and XL32.1 amino acid sequences

| AAV capsid protein | Reference | Amino Acid Sequence | SEQ ID NO: |
|---|---|---|---|
| XL32 And XL32.1 | International Publication No. WO 2019241324A1 | MAADGYLPDWLEDNLSEGIREWWALKpGAPKPKANQQKQDDGRGL VLPGYKYLGPFNGLDKGEPVNAADAAALEHDKAYDQQLQAGDNPY LRYNHADAEFQERLQEDTSFGGNLGRAVFQAKKRVLEPLGLVEEG AKTAPGKKRPVEPSPQRSPDSSTGIGKKGQQPARKRLNFGQTGDS ESVPDPQPLGEPPAAPSGVGPNTMASGGGAPMADNNEGADGVGNA SGNWHCDSTWLGDRVITTSTRTWALPTYNNHLYKQISSASTGASN DNHYFGYSTPWGYFDFNRFHCHFSPRDWQRLINNNWGFRPKRLNF KLFNIQVKEVTTNDGVTTIANNLTSTVQVFSDSEYQLPYVLGSAH QGCLPPFPADVFMIPQYGYLTLNNGSQAVGRSSFYCLEYFPSQML RTGNNFTFSYTFEEVPFHSSYAHSQSLDRLMNPLIDQYLYYLNRT QNQSGSAQNKDLLFSRGSPAGMSVQPKNWLPGPCYRQQRVSKTKT DNNNSNFTWTGASKYNLNGRESIINPGTAMASHKDDKDKFFPMSG VMIFGKESAGASNTALDNVMITDEEEIKATNPVATERFGTVAVNL QSSSTDPATGDVHVMGALPGMVWQDRDVYLQGPIWAKIPHTDGHF HPSPLMGGFGLKHPPPQILIKNTPVPANPPAEFSATKFASFITQY STGQVSVEIEWELQKENSKRWNPEVQYTSNYAKSANVDFTVDNNG LYTEPRPIGTRYLTRPL | 3 |

Non-Human Primate (NHP) Studies

All studies used male cynomolgus monkeys (*Macaca fascicularis*, Asian origin) at 2 to 3 years of age (3-4 kg). Animals were screened for neutralizing antibodies for vector capsid prior to vector administration. Selected animals received vector by slow intravenous infusion (1 ml/min) into saphenous vein using an infusion pump. Blood samples were collected at various times. At necropsy, samples from liver and multiple other organs were collected for vector biodistribution analysis.

For vector detection, total tissue DNA was isolated from each tissue using 1.4 mm ceramic beads and OMNI BEAD RUPTOR 24™ followed by proteinase K digestion and phenol/chloroform extraction. DNA was precipitated by isopropyl alcohol, spun and re-suspended into Tris-EDTA. DNA was quantitated and the levels of vector derived DNA was measured by qPCR using specific primers to the BGHpA sequences present in each VG (Kyostio-Moore et al. 2016). The levels of VGs were expressed as copies per cell (using 5 pg dsDNA per diploid cellular genome).

Homogenates for total EGFP protein measurement were generated using OMNI BEAD RUPTOR 24™ beater in ELISA kit extraction buffer PRT (Abcam GFP ELISA kit; ab171581) with added Protease inhibitors (Roche). After centrifugation, supernatant was recovered and diluted with kit extraction buffer PRT and EGFP protein levels was quantitated by ELISA according to manufacturer's instructions. All values were expressed as ng EGFP/mg total protein. Total protein was measured by BCA assay.

For vector derived transcipt quantitation, liver and spleen homogenates were generated using OMNI BEAD RUPTER 24™ beater in 2 ml tubes containing 1.4 mm ceramic beads and 1 mL TRIZOL® (Thermofisher, A33250). Chloroform was added, mixed and then aqueous phase was transferred to a column in SV total RNA kit, Promega Z3100. DNase treatment was performed on the column and after washing the column, RNA was eluted in water. Total RNA was quantified using Nanodrop 8000. cDNA was generated by random primers using High Capacity cDNA RT kit (Thermofisher, 4368814). The levels of vector derived mRNA were measured by qPCR using specific primers to the BGHpA sequence. The levels of transcripts were expressed as copies per cell (using 5 pg dsDNA per diploid cellular genome) or per µg RNA.

Immohistochemistry and in situ hybridization analyses for liver were performed with 4 µM sections cut from neutral buffered formalin-fixed paraffin embedded blocks. For the automated fluorescence in situ hybridization (RNAS-COPE™) and IHC, all steps were performed on a Leica Bond RX instrument (Leica Bios, systems Inc., Buffalo Grove, IL). A sequential double stain mode was utilized, beginning with the RNASCOPE™ 2.5 LS Multiplex Fluorescent assay (Advanced Cell Diagnostics, Newark, CA) and followed by IHC. Briefly, unbaked paraffin sections were baked at 60° C. for 30 min and deparaffinized at 60° C. and then pretreated with Bond ER Solution 2 for target retrieval, protease, and hydrogen peroxide prior to hybridization of the negative probe, DapB (cat #320878, Advanced Cell Diagnostics, Newark, CA), positive probe, *M. fascicularis* PPIB (cat #320908), or target probe, eGFP (cat #400288, Advanced Cell Diagnostics, Newark, CA) at 42° C. for 2 hours. Preamplifiers and amplifiers were hybridized consecutively, and slides were then incubated with OPAL690 diluted 1:1500 (cat #FP1497001KT, Akoya Biosciences, Marlborough, MA). HRP blocker was applied and sections were subjected to target retrieval with Bond ER Solution 1 prior to the IHC portion of the automated protocol. Slides were blocked with Antibody Diluent/Block (Akoya Biosciences, Marlborough, MA) followed by incubation with rabbit IgG isotype control (cat #AB105-C, R&D Systems, Minneapolis, MN) or rabbit anti-GFP, used at 11 µg/mL (cat #A11122, Invitrogen/ThermoFisher, Waltham, MA) at RT for 30 min. A secondary antibody, anti-rabbit Polymer HRP (cat #PV6119, Leica Biosystems Inc., Buffalo Grove, IL) was applied and detection was achieved by OPAL570 diluted 1:150 (cat #FP1488001KT, Akoya Biosciences, Marlborough, MA). Cells were counterstained with Spectral DAPI (Akoya Biosciences, Marlborough, MA). 20× Images were acquired by a Zeiss AXIOSCAN™ ZI. 20× Images were imported into HALO (Indica labs) image analysis software and analyzed using the FISH-IF v1.1.3 imaging module.

Comparison of XL32 and XL32.1 Capsid Proteins

Figure 5A:
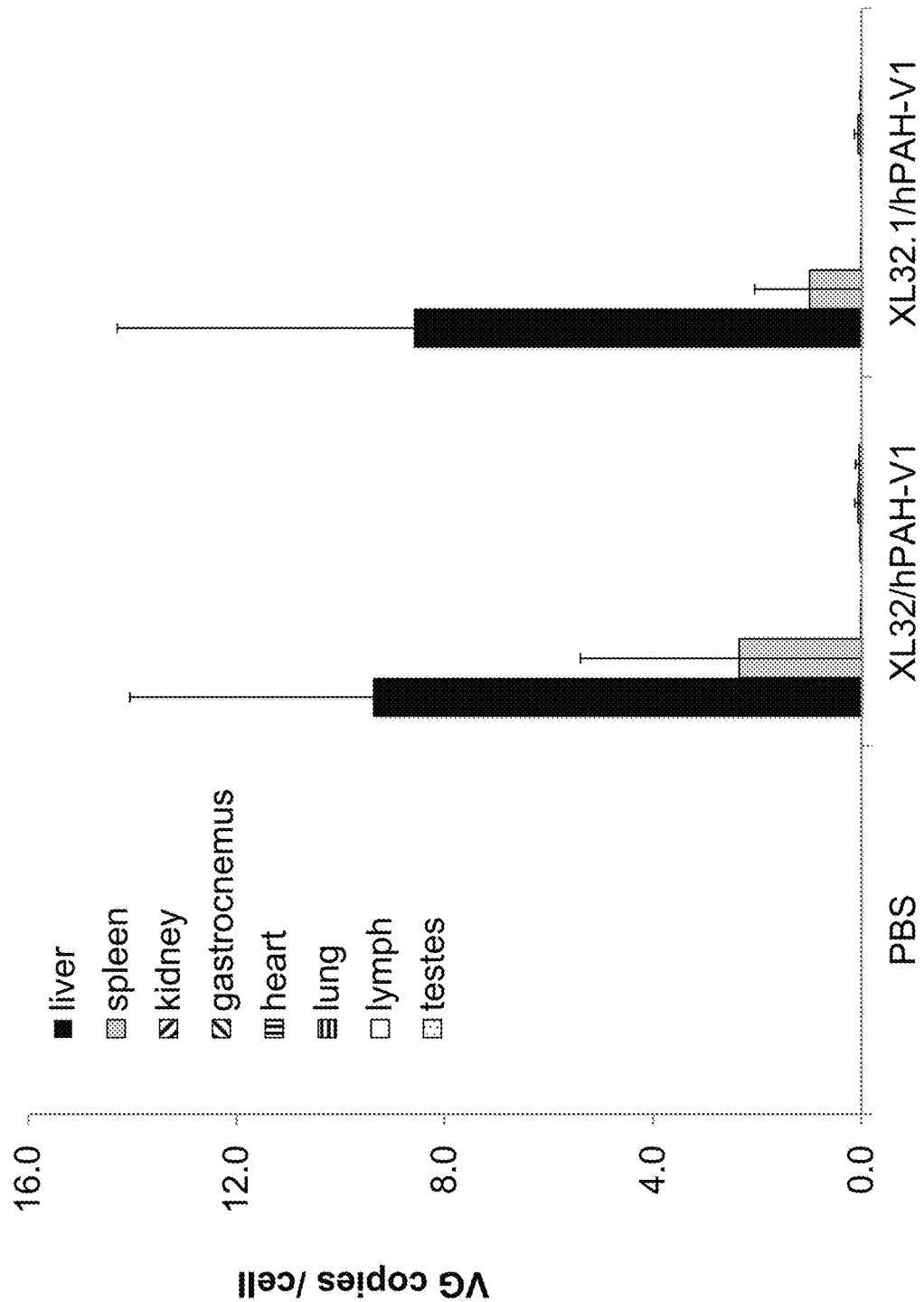
FIGS. 5A-5B show a comparison of the biodistribution of XL32 and XL32.1 capsid vectors in NHPs.
Figure 5B:
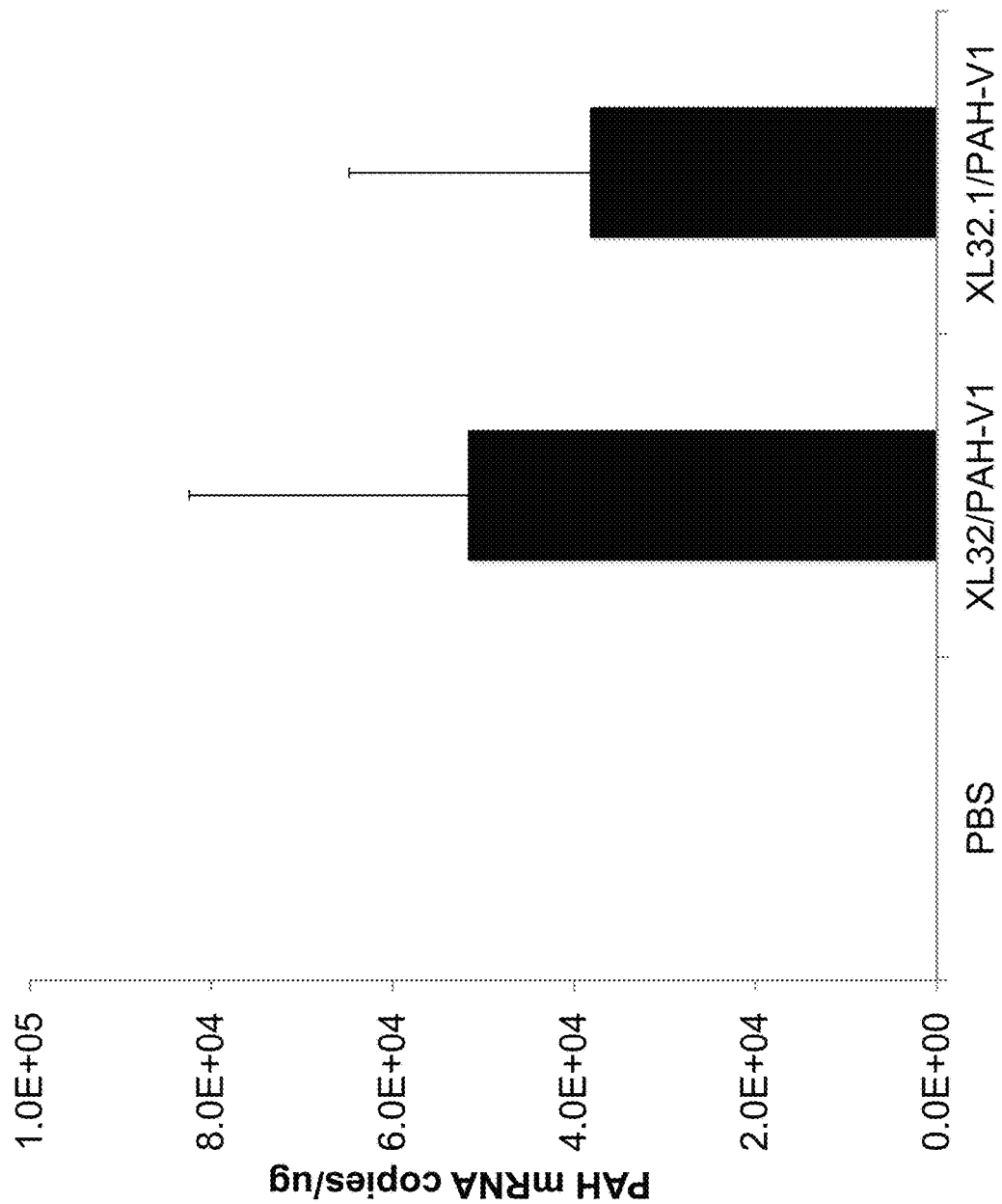

Vectors expressing hPAH-V1/G using the mA1M2-mTTR482 promoter were packaged into either the XL32 or XL32.1 capsid, and administered to NHPs. 5e12 vg/kg of vector was administered by IV delivery, and the number of vector genome copies per cell in the liver and various other organs was measured 2 weeks following administration by qPCR (FIG. 5A). Further, the level of vector-derived mRNA in the liver was measured (FIG. 5B).

Results

Initial AAV Capsid Study

Figure 2A:
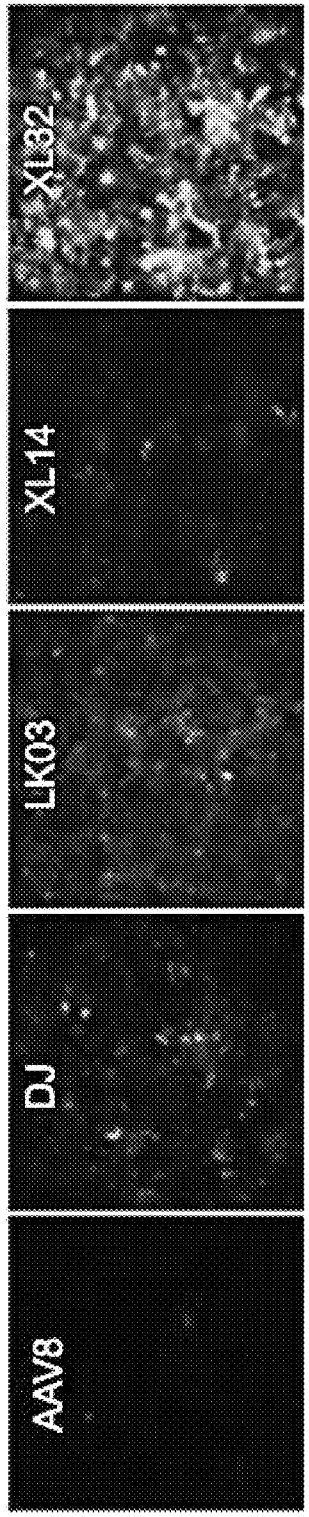
FIGS. 2A-2E show the results of experiments comparing AAV capsids for gene transfer to liver cells and organs in non-human primates (NHPs), and validating the A1M2-mTTR promoter in NHPs.
Figure 2B:
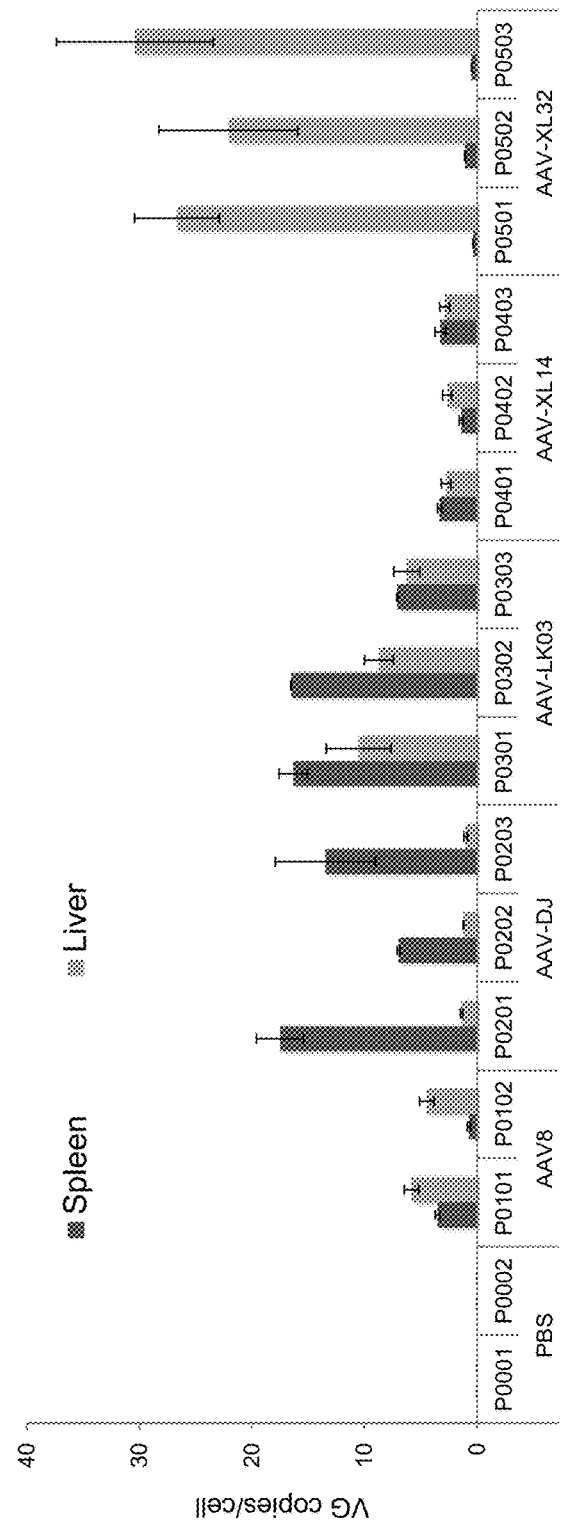
Figure 2C:
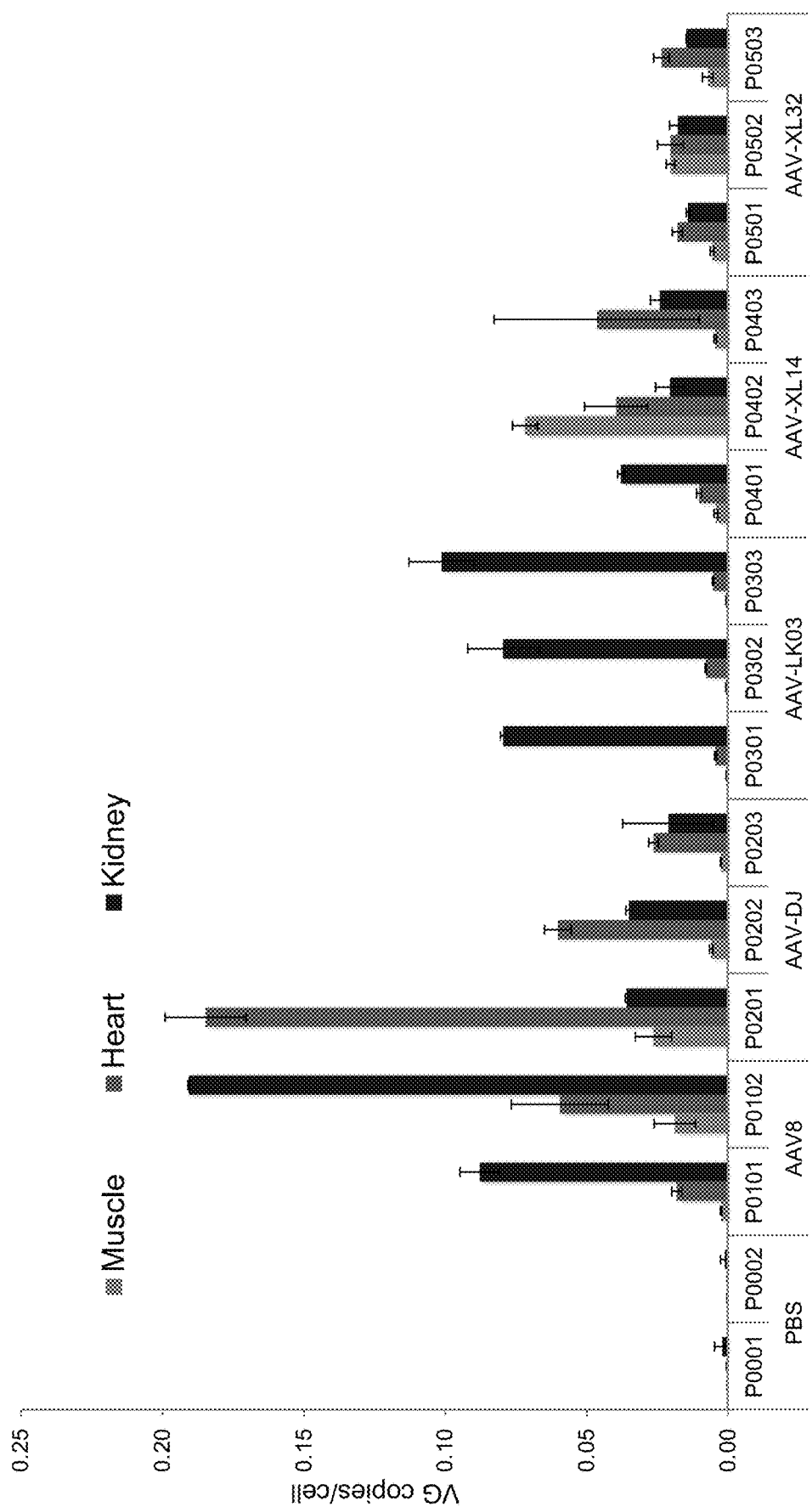
Figure 2D:
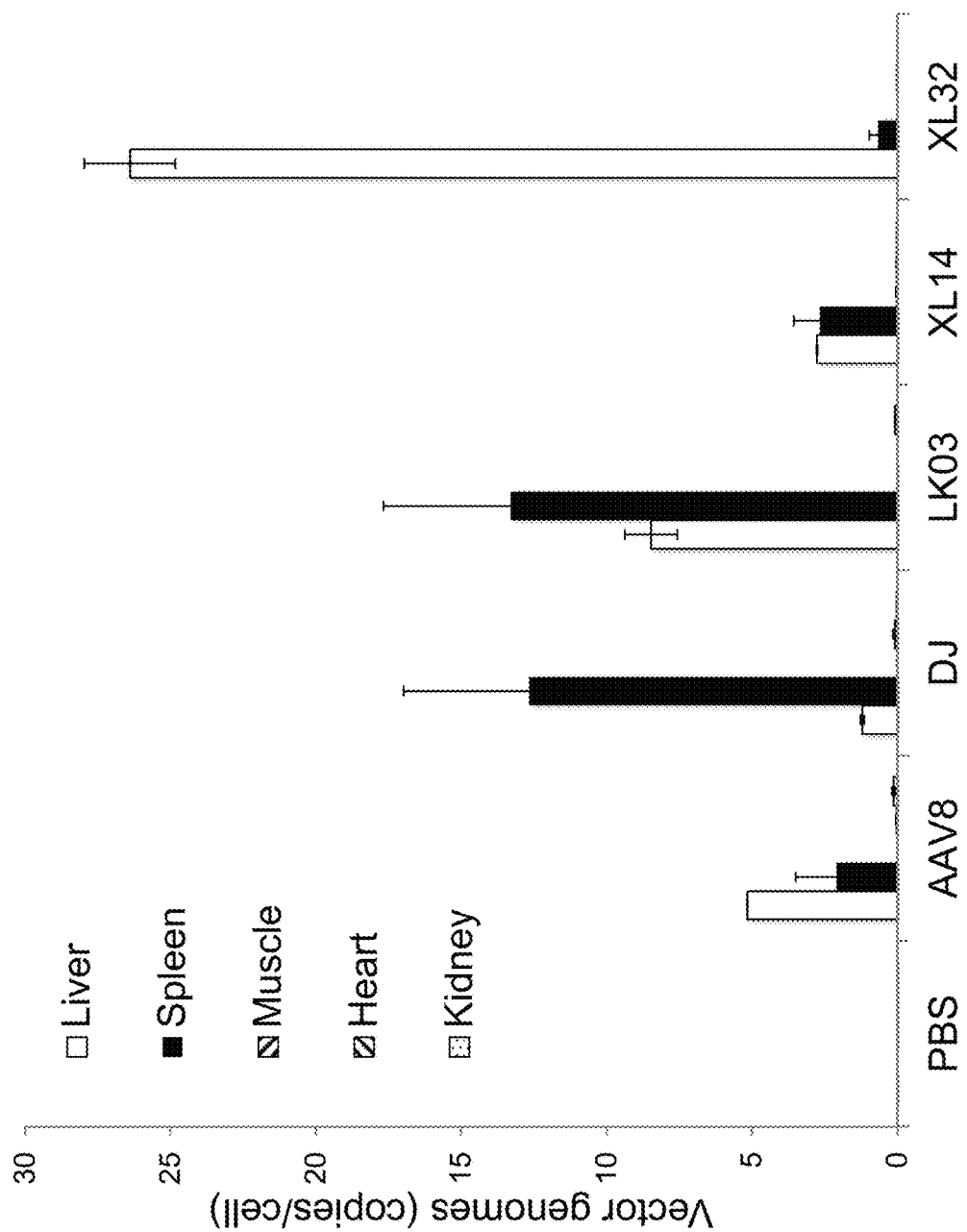
Figure 2E:
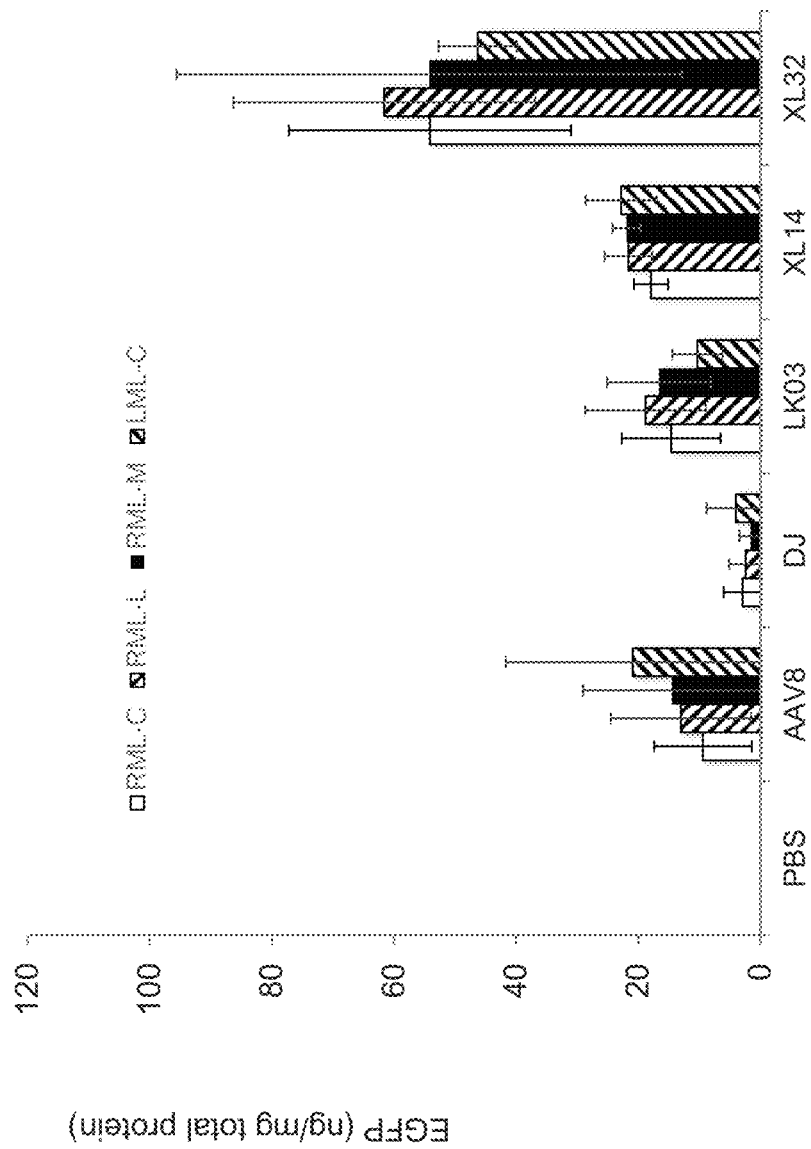

To select an AAV capsid for PAH gene transfer that would provide good translatability to human gene transfer, five AAV capsids, each containing CBA-EGFP vector genome were generated. The vectors showed varying levels of EGFP detection in Huh7 cells in vitro (FIG. 2A). The AAV vectors were then delivered by intravenous route into NHPs followed liver and various organs were collected two weeks later. For liver samples, VGs were measured in right medial lobe in three different areas and showed comparable levels within each sample therefore indicating even distribution within a lobe (data not shown). Distribution between lobes was also evaluated by quantitating VGs in right and left medial lobes and demonstrated comparable VG copies in both lobes (data not shown). The average of these four samples in liver for each animal is shown in FIG. 2B. The highest vector gene transfer was observed with rAAV-XL32, followed by AAV-LK03, AAV8, rAAV-XL14 and the lowest with rAAV-DJ with approximately 22-fold difference between the highest and lowest ranking capsid vector. In each capsid treatment group, the VGs levels in individual animals were comparable. VG copies were also measured in spleen (FIG. 2B) and muscle, kidney and heart (FIG. 2C). Very little vector genomes were observed for XL32 in other tissues. In summary, the XL32 capsid vector delivered by systemic administration provided robust uptake to liver while very little vector with this capsid was detected in other organs examined (FIG. 2D). Expression of EGFP within a lobe and between lobes is shown in FIG. 2E.

NHP Dose Response Study

Figure 3A:
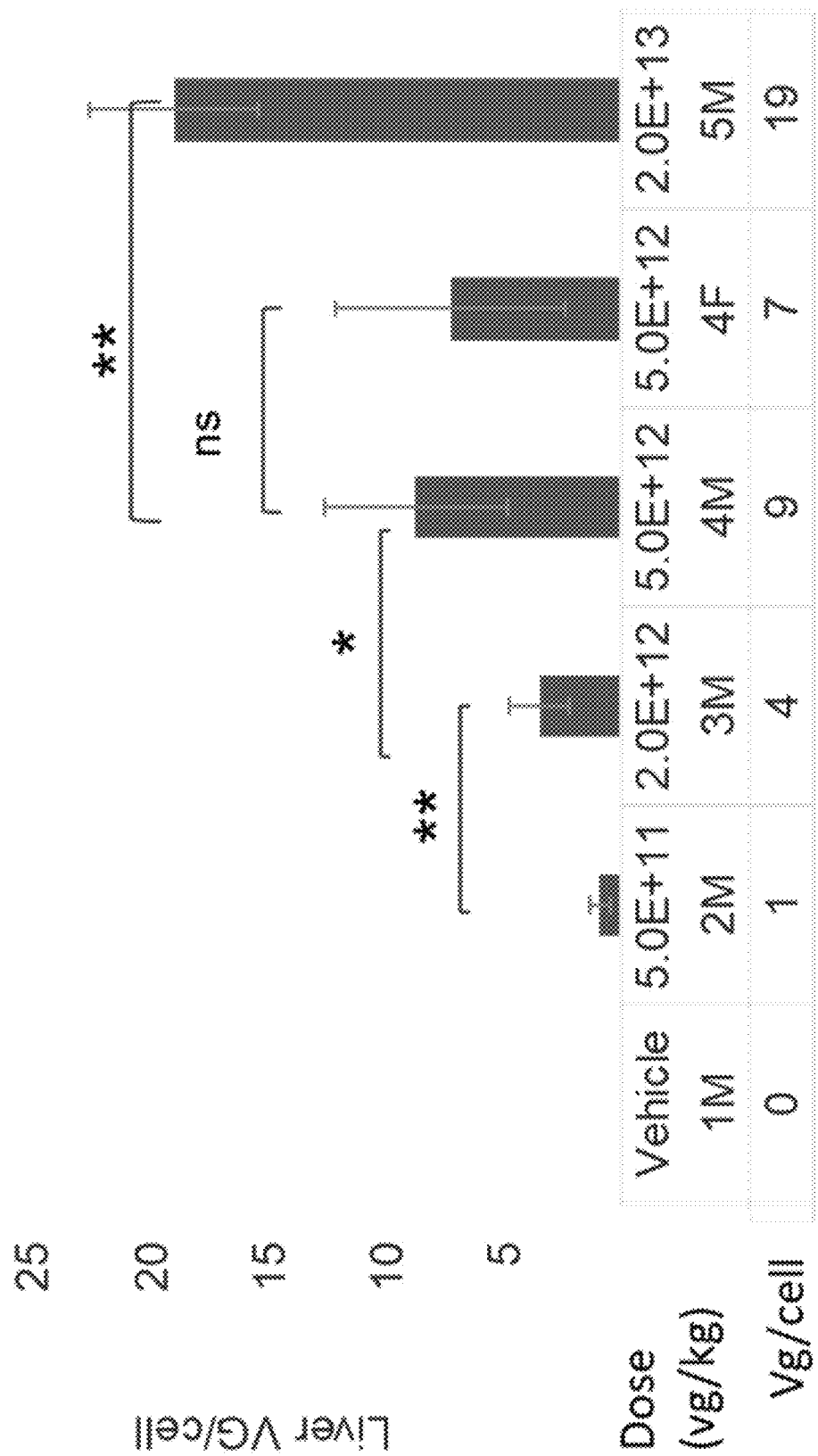
FIGS. 3A-3E show the results of an experiment measuring the dose-response of XL32.1/mA1MB2-mTTR482-EGFP for NHP liver gene transfer.

In a second NHP study, the dose-responsiveness of liver gene transfer by XL32.1/mA1MB2-mTTR482-EGFP was evaluated. The vector was delivered by IV route and tissues were collected 16 days later. For liver analysis, two liver samples (collected from right and left medial lobe) showed comparable VG levels (data not shown). The dose cohorts @ 5e11, 2e12, 5e12 and 2e13 vg/kg had on average 0.9, 3.5, 8.8 and 7.3 (M and F) and 19.0 VG/cell, respectively (FIG. 3A). Hence, dose-response was demonstrated for all but the highest dose. Within the two highest doses, there was variability among the individual animals that may have been due to immune response to transgene. Comparable vector genomes were detected for male and female animals at the 5e12 vg/kg cohort (FIG. 3A).

Figures 3B, 3C:
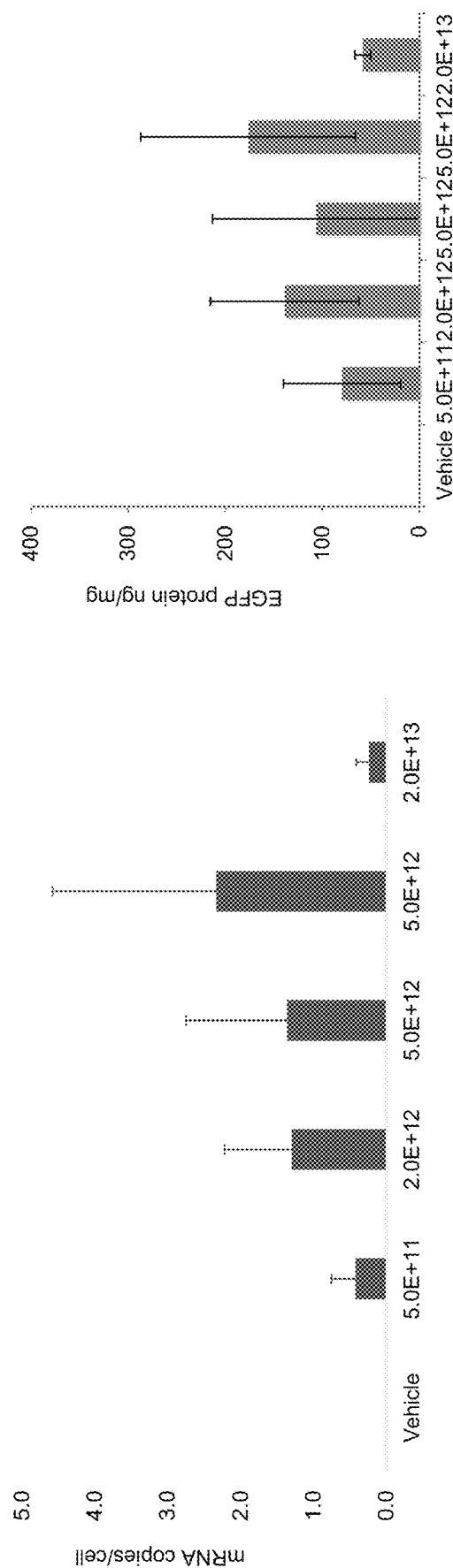

The vector promoter function was evaluated by measuring vector derived eGFP mRNA levels in liver samples. Overall, there was a trend of increased transcript levels per cell with increased dose (FIG. 3B). The highest dose tested (2e13 vg/kg) resulted in low mRNA likely due to immune reaction to eGFP protein (and corresponding to lower VG detection).

Figure 3E:
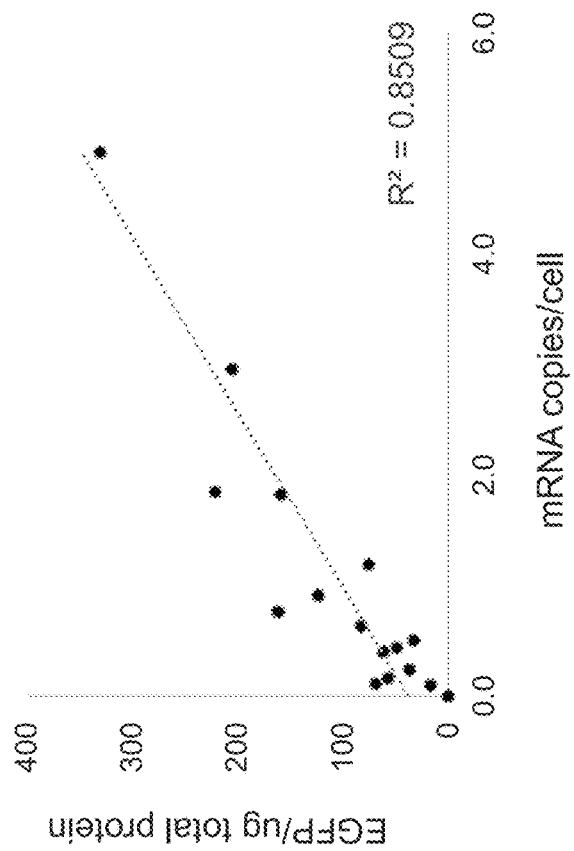
Figure 3D:
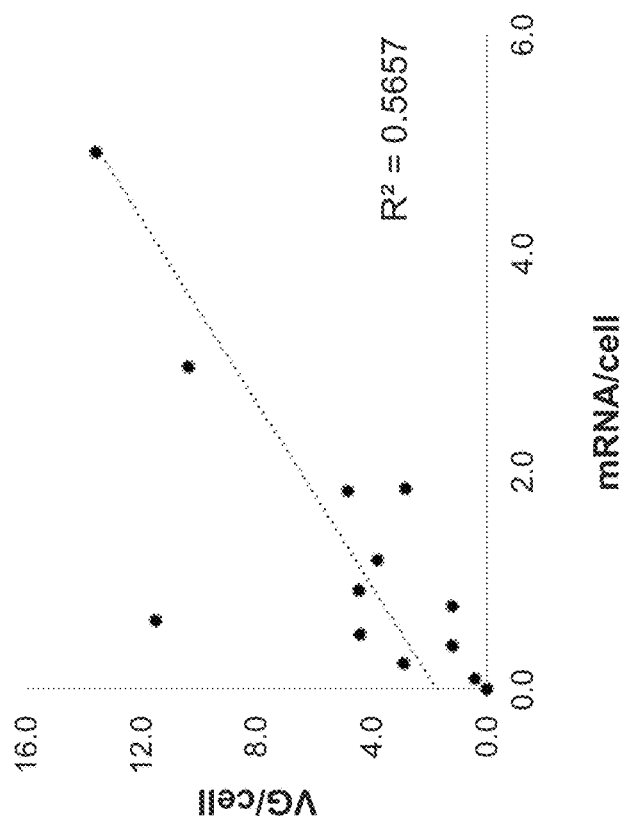

Vector transduction was evaluated by measuring eGFP protein levels in liver. The data did not show a dose-response for eGFP protein levels; high eGFP levels were detected even in the two lower doses while the highest dose resulted in the lowest eGFP levels (FIG. 3C). Despite this, there was a good correlation between liver VG and vector derived mRNA copies ($r2=0.57$) (FIG. 3D). Good correlation ($r^2=0.85$) was also observed between mRNA copies and eGFP protein levels (FIG. 3E). This may suggest that not all vector genomes were transcriptionally active but once transcription occurred, eGFP protein production was directly proportional to transcript levels.

Figure 4A:
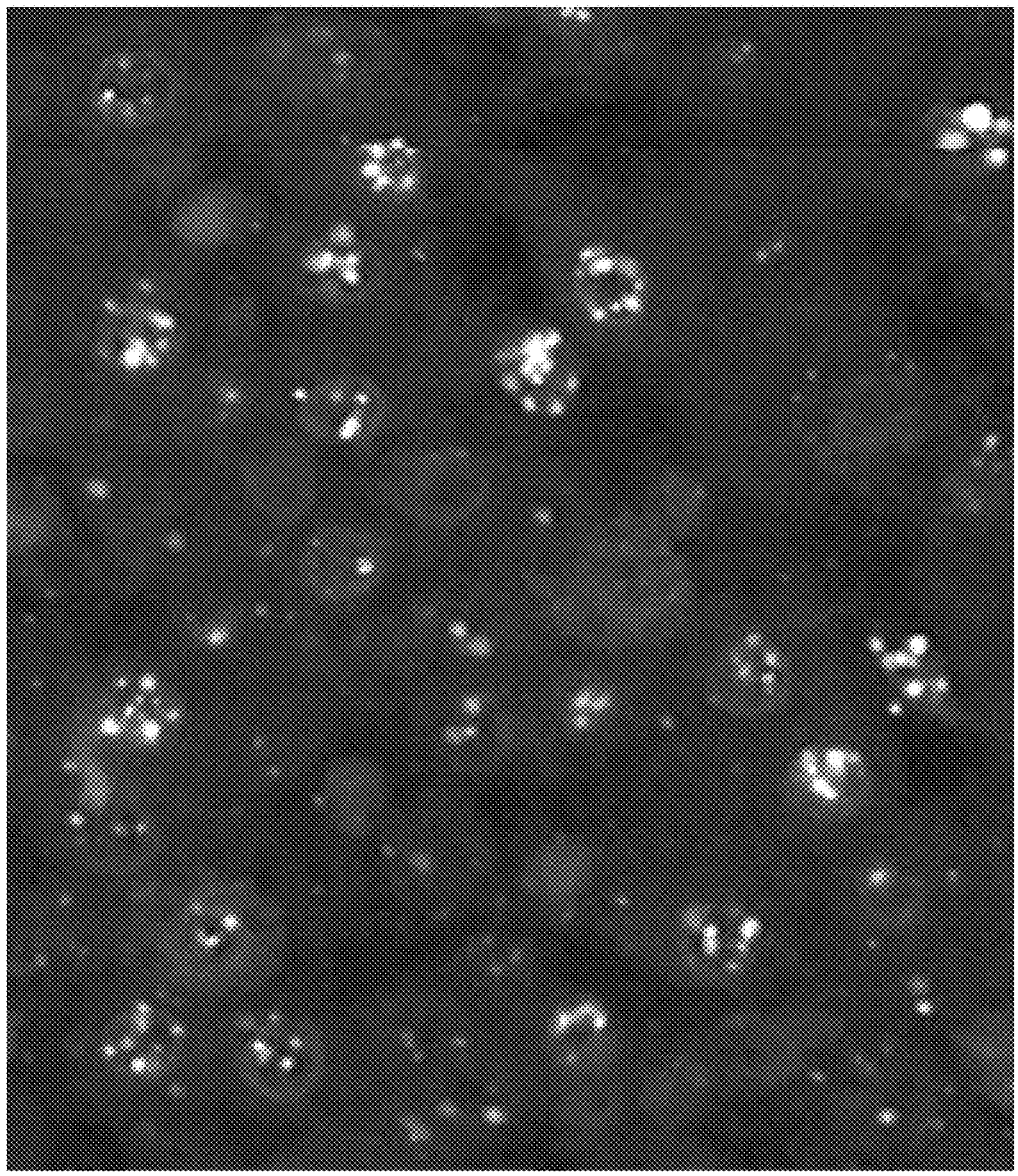
FIGS. 4A-4C shows the results of a liver in situ hybridization analysis in the dose-response study of XL32.1/mA1MB2-mTTR482-EGFP administered to NHPs.
Figure 4B:
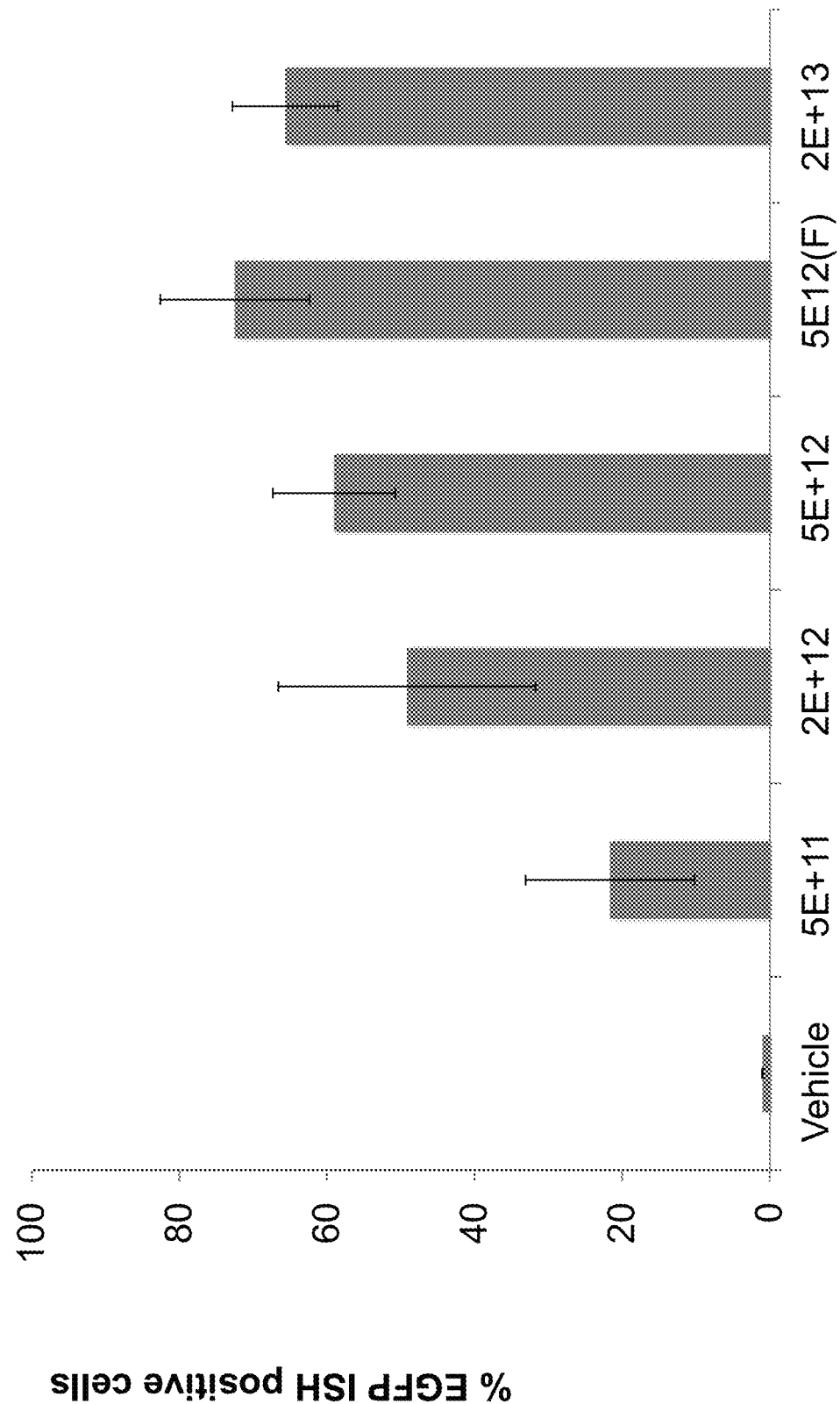
Figure 4C:
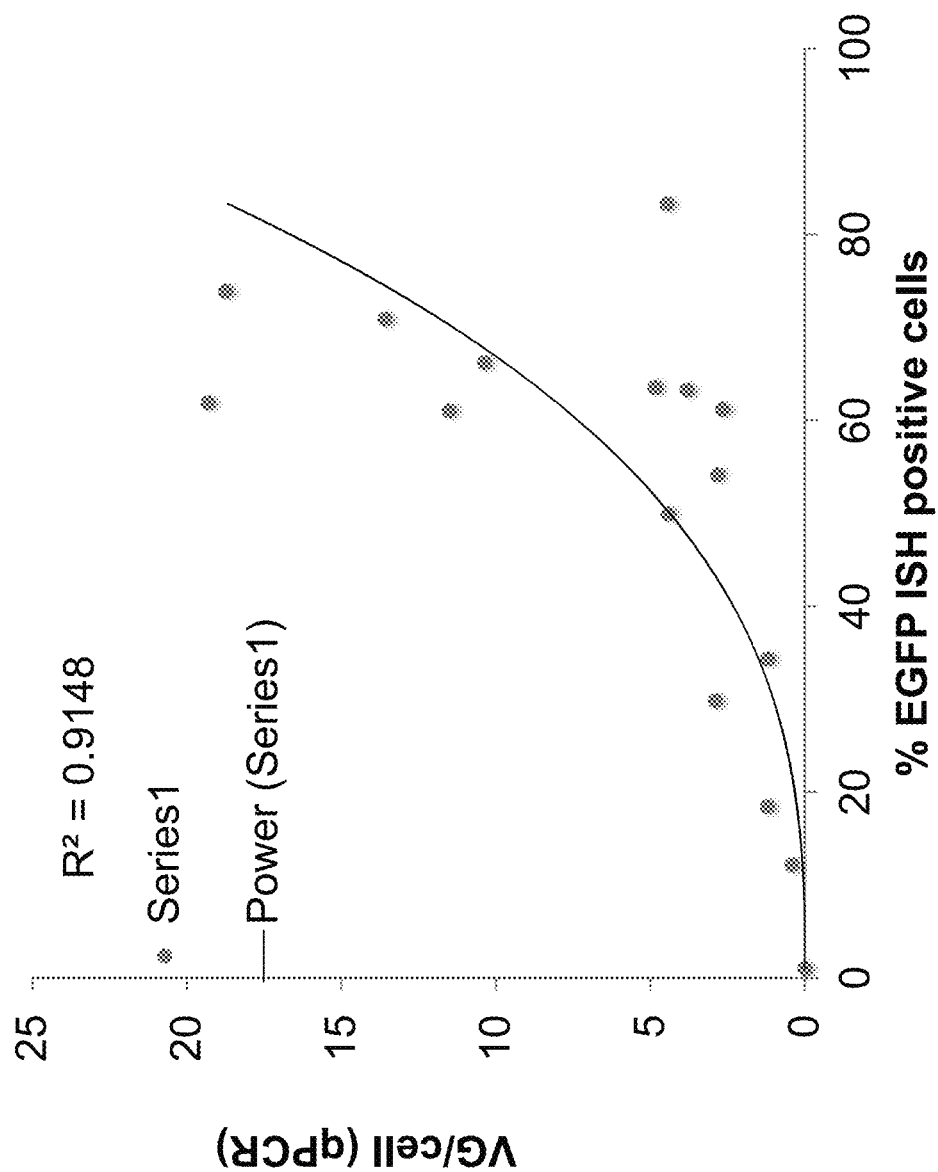

Vector uptake and localization in liver was evaluated by hybridization with an eGFP probe to understand % hepatocytes that had taken-up the vector. This probe is expected to detect both vector DNA and mRNA. An example of in situ hybridization image is shown in FIG. 4A. The vector positive hepatocytes was quantitated to estimate the percentage of vector positive cells in liver (FIG. 4B). The data demonstrated that the vector positive cells increased with vector dose. At dose of 5e12 vg/kg, approximately 50-80% of cells in liver were positive in livers of both male and female animals. There was a good correlation between the percentage of positive cells and the average number of VG copies in the liver (FIG. 4C).

Comparison of XL32 and XL32.1 Capsid Proteins

An experiment was performed to compare the biodistribution of XL32 and XL32.1 capsid vectors in NHPs. As shown in FIGS. 5A-5B, XL32 and XL32.1 resulted in comparable levels of viral genomes and vector derived mRNA in the liver.

Example 3. In Vivo Efficacy of XL32.1/mA1MB2-mTTR482-WT PAH in Pah-KO Mice

The following example describes a study of the in vivo efficacy of XL32.1/mA1MB2-mTTR482-WT PAH in Pah-KO mice.

Materials and Methods

Efficacy Testing in PAH-KO Mouse

Homozygous (HOM) and heterozygous (HETs) Pah-KO male mice are obtained at 8-12 weeks of age and housed and maintained in accordance with humane guidelines for animal care and use. All animal procedures are approved by the Sanofi's Institutional Animal Care and Use Committee (IACUC).

Recombinant AAVXL32.1 vectors are administered by intravenous route via tail vein (6-10 animals/treatment). Animals are sacrificed by isoflurane anesthesia. Whole blood is collected by retro-orbital sinus into EDTA collection tubes, spun and stored frozen until analysis. Some animals are perfused with PBS via the left cardiac ventricle before tissue collection. Liver samples are collected and frozen until analysis. For brain analyses, whole brain is harvested from the cranium, weight, cut sagittally and is frozen at −80° C. until analysis.

Blood and Tissue Analyses

Plasma Phe and Tyr levels are analyzed by UHPLC-MS/MS. For brain neurotransmitter quantitation, brains are processed as described with minor modifications (Kankaanpaa 2001). For liver samples, vector genomes, PAH activity and protein levels are quantitated. Copies of vector genomes are quantitated by qPCR (Martin 2013). PAH protein activity in liver homogenates is performed as described above and normalized by total protein (BCA protein assay kit; Pierce).

Results

XL32.1/mA1MB2-mTTR482-WT PAH is tested for efficacy in a PKU mouse model. A Pah-KO model lacking any PAH protein production is used. The vector is administered into adult mice by IV and efficacy is evaluated for 35 days or 4 months post-treatment.

Levels of Phe and Tyr in the blood and brain are measured. Dopamine and serotonin levels are measured in the brain. Lastly, behavior is assessed, for example, by a nest building assay.

4 months following administration, an in-depth analysis of brain pathology and white matter changes is performed. These are evaluated by in vivo MRI and by terminal white matter staining.

Example 4. Short-Term In Vivo Efficacy of XL32.1/mA1MB2-mTTR482-WT hPAH in PAH-KO Mice The XL32.1/mA1MB2-mTTR482-WT hPAH vector (also known as XL32.1/WT hPAH) was evaluated in vivo in PKU mouse model for 5 weeks. A dose-dependent reduction of blood Phe levels and increase in blood Tyr was observed after Pah gene transfer to liver. This correlated with dose-dependent detection of vector genomes, vector derived mRNA and PAH activity in livers of treated mice. The Phe lowering increased amino acid transport to brain and various neurotransmitter levels. Evaluation of level of PAH positive cells in liver demonstrated pericentral detection of PAH positive hepatocytes with increasing intensity that correlated to vector dose. In summary, our work demonstrates that the optimized rAAVXL32.1 vector encoding WT hPAH corrected PKU related pathologies in the PAH-KO mouse model and hence supports its use for the treatment of human PKU.

Materials and Methods

Vector generation. The XL32.1 capsid vector encoding WT hPAH expressed from optimized liver promoter and intron (mA1MB2-mTTR482-HI2) was produced by triple transfection as described above. The vector was purified by affinity column followed by CsCl gradient. The vector was titered by qPCR and PAH production and function was tested in vitro prior to animal studies.

Efficacy testing in PAH-KO mouse. A colony of Pah-KO mice generated in C57BL/6 background was maintained at Jackson Laboratory (Singh et al, 2020; submitted). Some studies also used WT C57BL/6 mice as normal controls. Homozygous (HOM) and heterozygous (HETs) male mice were obtained at 8-12 weeks of age and were housed and maintained in accordance with humane guidelines for animal care and use. The vector was administered by intravenous route via tail vein (6-10 animals/treatment). Animals were sacrificed by isoflurane anesthesia. Whole blood was collected by retro-orbital sinus into EDTA collection tubes, spun and stored frozen until analysis. Some animals were perfused with PBS via the left cardiac ventricle before tissue collection. Liver samples were collected and frozen until analysis. For brain analyses, whole brain harvested from the cranium, weight, cut sagittally and was frozen at −80° C. until analysis.

Blood and tissue analyses. The plasma Phe and Tyr levels were analyzed by UHPLC-MS/MS as described in Singh et al, 2021. For brain neurotransmitter quantitation, brains were processed as described with minor modifications (Kankaanpaa 2001; Singh 2020). Copies of vector genomes were quantitated by qPCR in various tissues (Martin 2013). PAH protein activity and PAH protein detection in liver homogenates was performed as previously described (Heintz 2012, Nambiar 2017) and normalized by total protein (BCA protein assay kit; Pierce).

Animal behavior assay. Nest building assay was performed as previously published with minor modifications (Deacon 2006). Animals were moved to a clean, individual cage and provided with 3.0 gm+/−0.02 square of cotton (Nestlet; cabfm00088, Ancare). Any unused bedding material was weighed the next day and the quality of nest was scored by two individuals based on the following rating scale: 1—Nestlet not touched (more than 90% intact), 2—Nestlet partially torn (50-90% intact), 3—Nestlet mostly shredded but often without identifiable nest site (less than 50% intact), 4—An identifiable but flat nest (more than 90% of the Nestlet is torn), 5-perfect nest with a crater and high walls (more than 90% of the Nestlet is torn).

Graphing and statistical analysis. All the data was graphed using GRAPHPAD PRISM™ (version 8.0.2) or Excel (Microsoft). Statistical analysis was performed using Student t-test in Excel or 1-way ANOVA in GRAPHPAD PRISM™.

Results

Figure 6A:
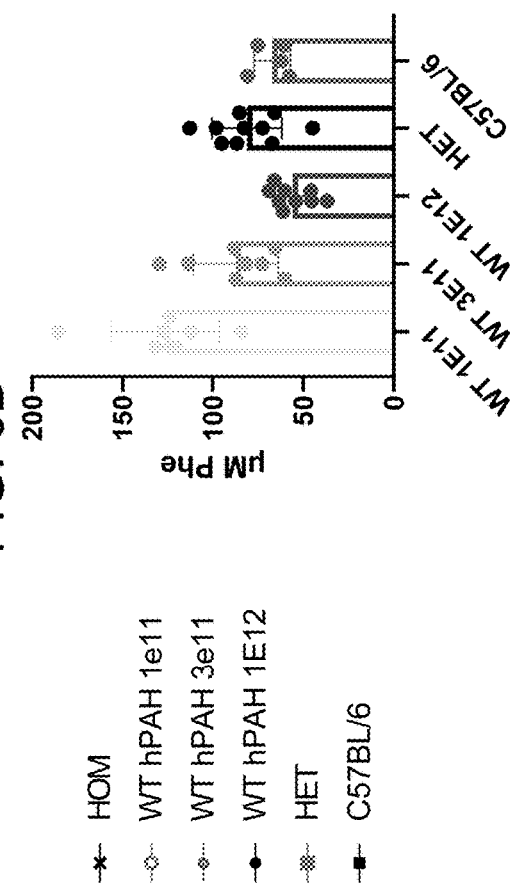
FIGS. 6A-6D show the efficacy of XL32.1/WT hPAH in Pah-KO mice.
Figure 6B:
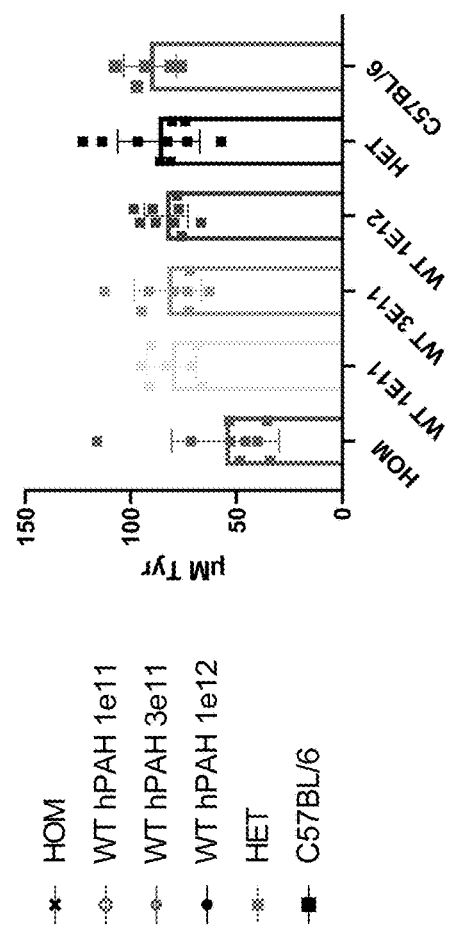
Figure 6C:
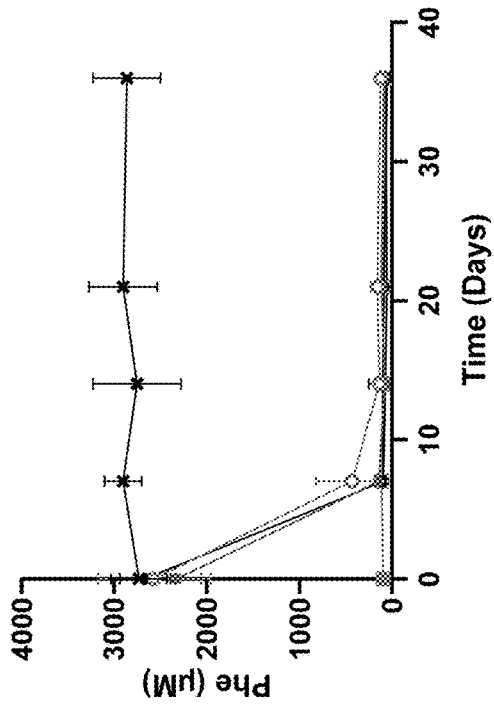
Figure 6D:
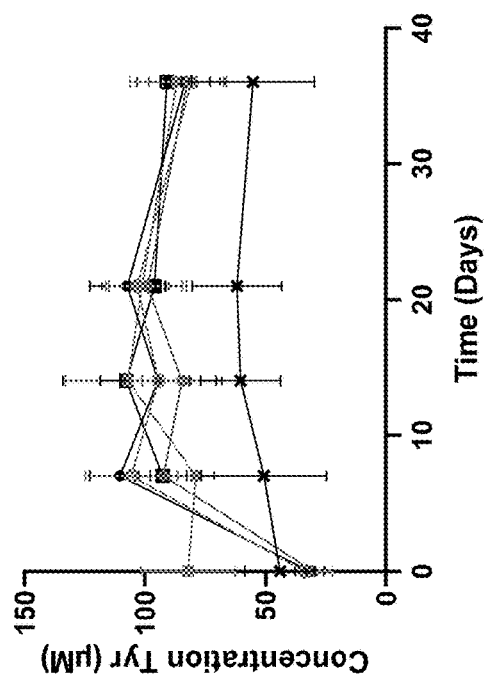

Blood Phe and Tyr correction after XL32 WT hPAH gene transfer to Pah-KO mice. A Pah-KO model lacking any PAH protein production was used to test efficacy of XL32/WT PAH vector after IV delivery and efficacy was evaluated for 36 days. The treatment reduced blood Phe levels in a dose-dependent manner to levels comparable to HET and WT mice (FIGS. 6A and 6B). Treatment also increased blood Tyr levels with normal blood Tyr levels obtained with all vector doses tested (FIGS. 6C and 6D).

Figure 7A:
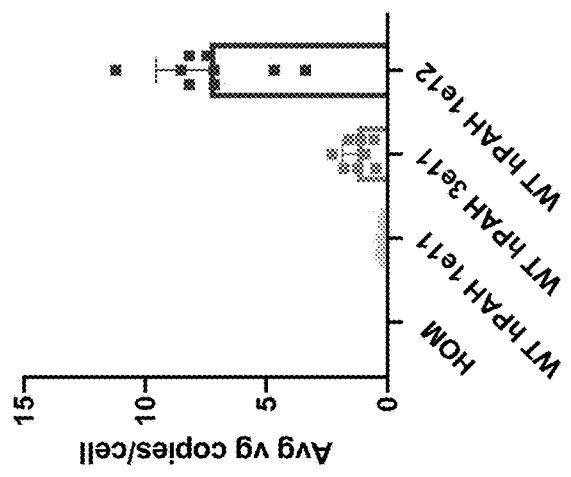
FIGS. 7A-7E show the analysis of gene transfer and transduction by XL32.1/WT hPAH in livers of Pah-KO mice.
Figure 7B:
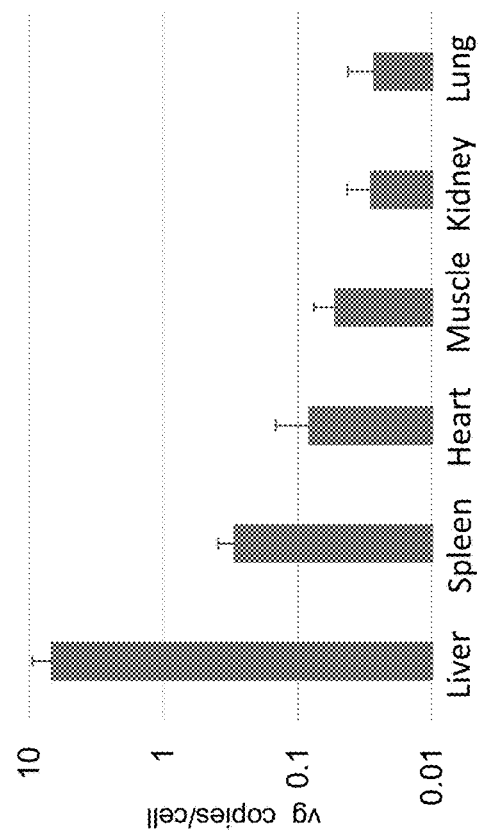
Figure 7D:
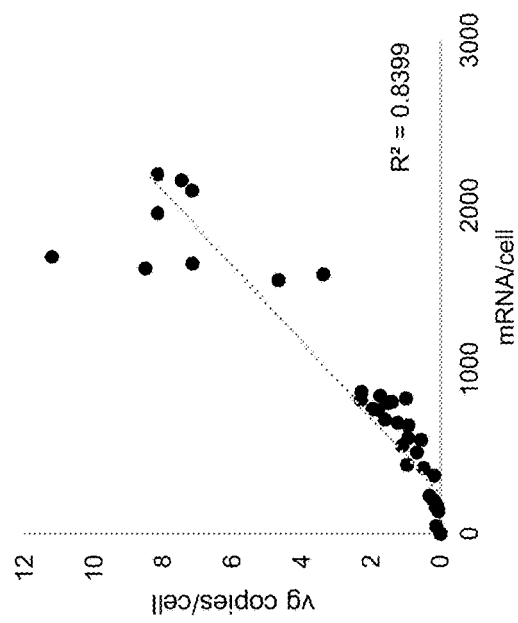
Figure 7C:
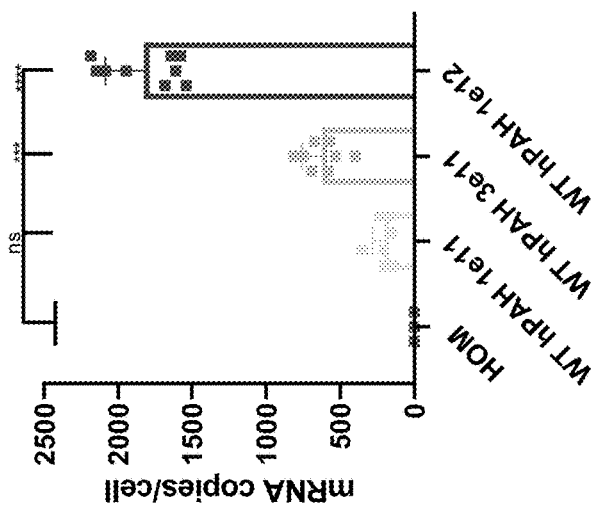
Figure 7E:
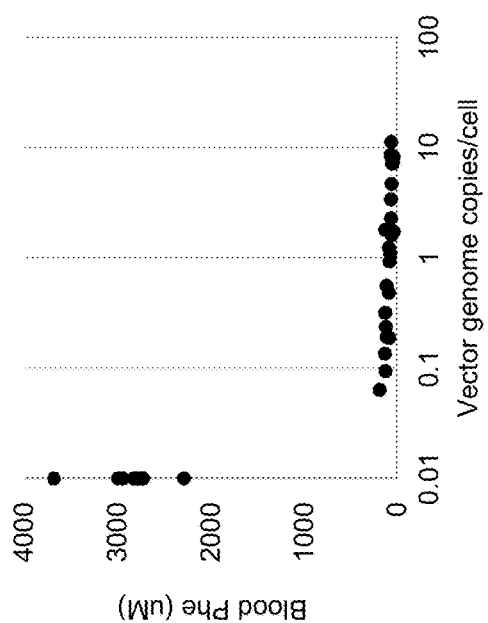

Livers of treated mice were evaluated for gene transfer efficiency and liver transduction. The vector DNA was detected in a dose-dependent manner in livers with 1e11, 3e11 and 1e12 vg/mouse resulting on average 0.2, 1.3 and 6.8 vg/cell (FIG. 7A). The vector was predominantly detected in liver, with over 10-fold lower levels measured in other tissues tested (spleen, heart, muscle, kidney and lung) (FIG. 7B). The dose dependent vector DNA detection translated to a dose-dependent increase of vector derived PAH mRNA in the livers (FIGS. 7C and 7D). Correlation of vg copies/cell to blood Phe levels demonstrated that a minimum 0.1 vg/cell was required for blood Phe normalization (FIG. 7E). The functionality of PAH protein was tested by measuring PAH activity in the livers. The low dose (1e11 vg/mouse) resulted in comparable PAH activity to that of activity in the Het mice while the two higher doses exceeded the activity measured in Het livers (FIG. 8A). Similar dose-responsive pattern of PAH protein levels was also observed by Western blotting of liver homogenates (FIG. 8B). To understand the location of transduced hepatocytes the treated livers were also evaluated by immunohistochemistry (IHC). Increasing PAH staining was detected with increasing dose with the transduction pattern being mainly pericentral (FIG. 8C).

Figure 9A:
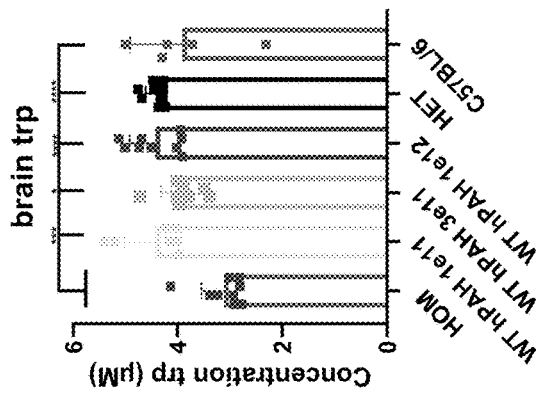
FIGS. 9A and 9B show the effect of XL32.1/WT hPAH delivery to liver on brain amino acid and neurotransmitter levels.
Figure 9A:
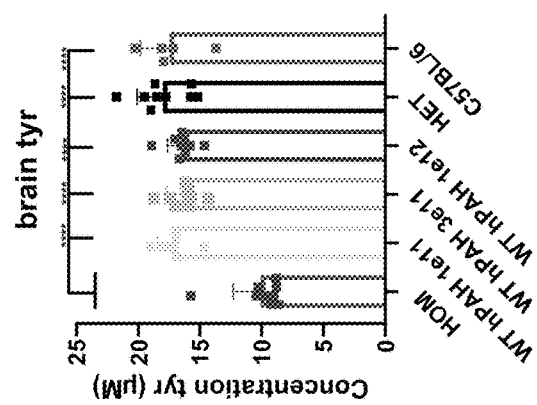
Figure 9A:
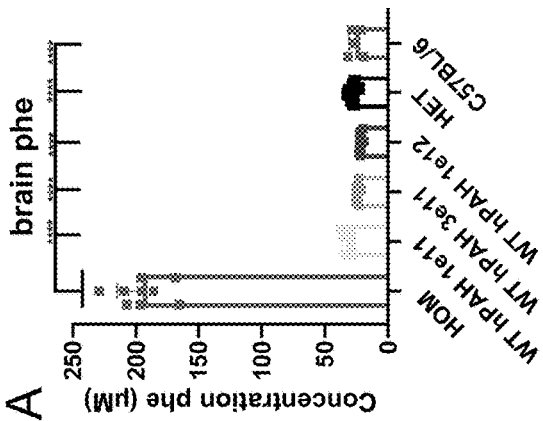

Effect of XL32.1 WT hPAH on brain amino acid and neurotransmitter levels. Amino acid Phe, Tyr and Trp levels were measured in brain. The data demonstrated normalization brain Phe levels after treatment as the levels were comparable to those measured in Hets and WT mice. Blood Phe reduction also increased amino acid Tyr and Trp transport into brain as these amino acids share the same amino acid transporter (FIG. 9A).

Figure 9B:
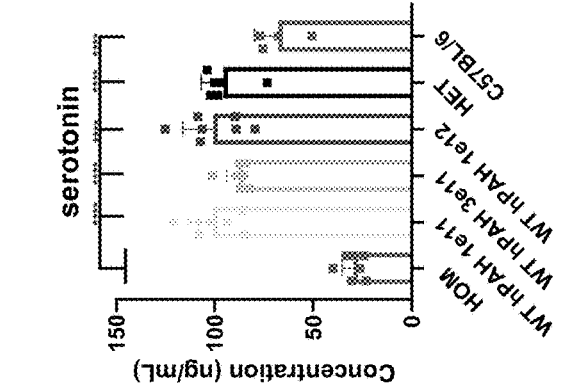
Figure 9B:
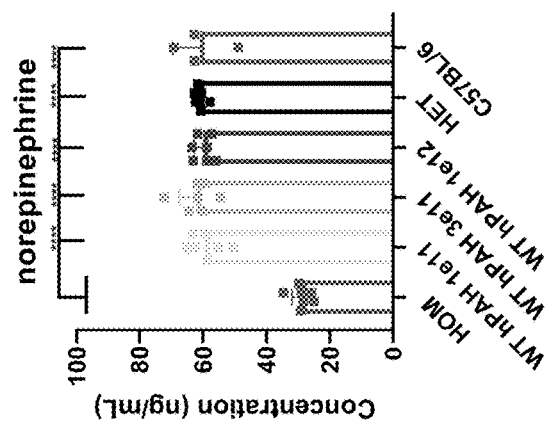
Figure 9B:
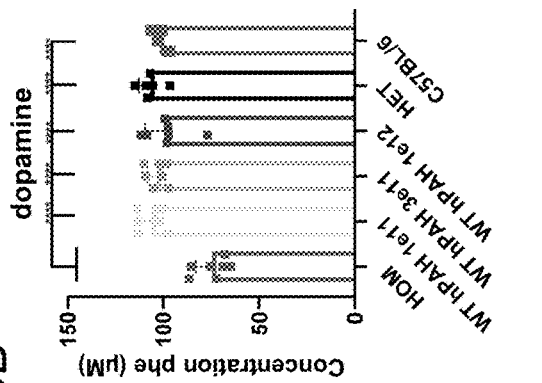

Neurotransmitters dopamine and serotonin are known to be reduced in brains of PKU patients. Hence, these neurotransmitter levels were quantitated in the brains of vector treated mice. Treatment with rAAVXL32.1/WT hPAH vector resulted in normalization of dopamine, norepinephrine and serotonin to levels observed in Het and WT mice (FIG. 9B).

Figure 10A:
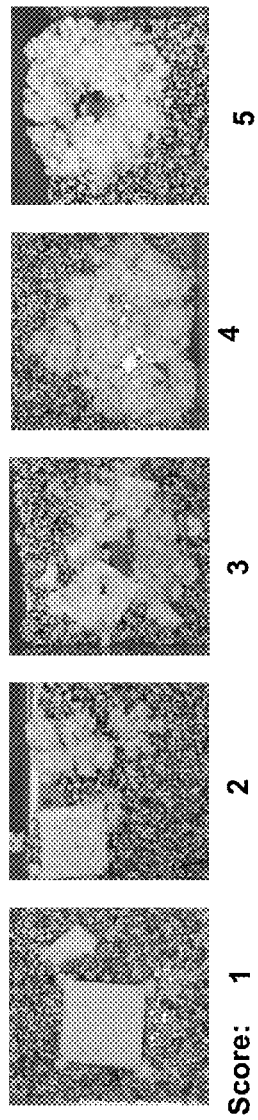
FIGS. 10A and 10B show behavioral analysis of Pah-KO mice after XL32.1/WT hPAH delivery.
Figure 10B:
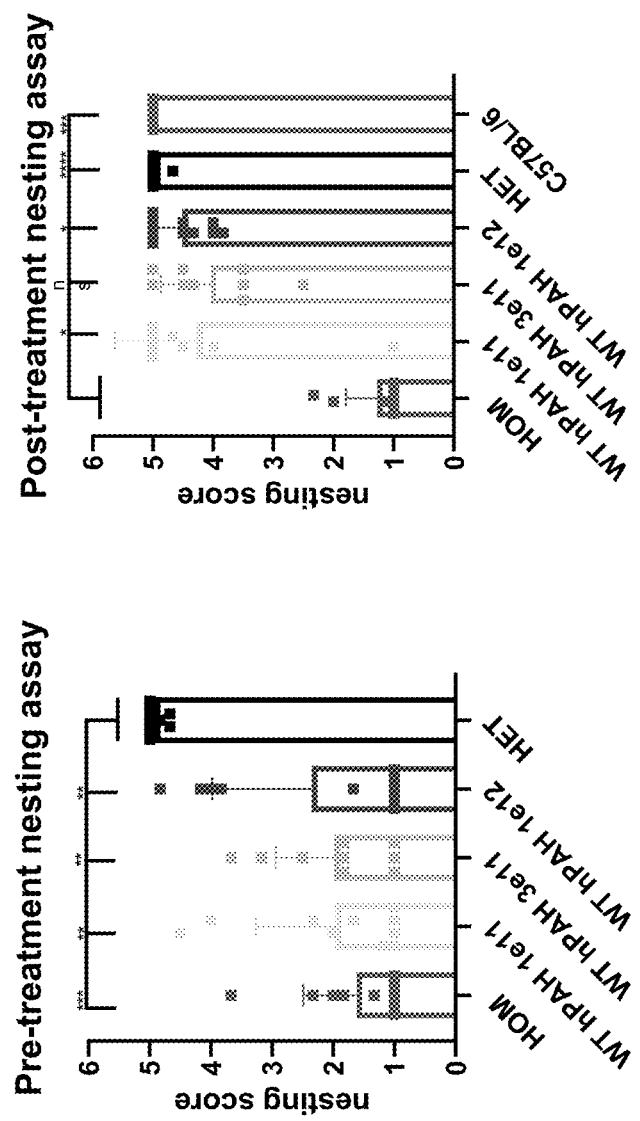

Behavior analysis of Pah-KO mice. A nesting behavior assay was performed to evaluate effect of biochemical changes in brain on animal behavior (FIGS. 10A and 10B). This assay measures the ability of the mice to generate a nest. These are then scored based on the amount of nesting material used and the overall quality of the nest (FIG. 10A).

Prior to treatment, all untreated PKU mice had significantly lower nest scores compared to those generated by Het mice (FIG. 10B). After 36 days of treatment, however, the scores were significantly improved in the treated mice (FIG. 10B). No differences were observed in the nesting scores between the Het and WT mice.

SUMMARY

Our data demonstrated that an rAAV vector consisting XL32.1 capsid and expressing WT hPAH from an optimized liver promoter was able to correct multiple PKU related pathologies in the mouse model of human PKU after 5-weeks of treatment. Systemic delivery of this vector resulted in a dose-dependent increase of vector, vector derived mRNA and PAH activity in the livers of Pah-KO mice. This was associated with lowering of Phe levels as well as increase in Tyr levels in the blood and subsequently in the brain with all the doses tested. Reduction of Phe both in blood and brain also normalized neurotransmitter dopamine and serotonin levels in brain. These biochemical changes correlated to improvement of behavior of the mice. The lowest dose of 5e12 vg/kg (1e11 vg/mouse) used in this study provided vector an average 0.2 vg/cell which resulted in comparable liver PAH activity measured in Het mice.

Example 5. Long-Term In Vivo Efficacy of XL32.1/mA1MB2-mTTR482-WT hPAH in PAH-KO Mice Materials and Methods Vector generation. The XL32.1 capsid vector encoding WT hPAH contained a liver-specific expression cassette with modified A1MB2 enhancer (2 copies alpha1-microglobulin), modified mouse transthyretin core promoter and distal enhancer (mTTR482), a hybrid intron 2 (HI2, intron consisting of chicken beta actin/rabbit beta globin hybrid intron) and a bovine growth hormone (BGH) polyadenylation site (BGH) (Nambiar 2017) (complete genome name ITR-/mA1M2-mTTR482-HI2-WT hPAH-BGHpA-stuffer-ITR; also known as XL32.1/WT hPAH). Two additional vectors with LP1 liver promoter were also constructed; one vector contained hybrid intron 2 (HI2) (identical as used in A1MB2-mTTR482 construct) or a short intron (SI, Nathwani 2012). The size for all constructs was adjusted to size of wild-type AAV genome by adding stuffer sequence (AlAT intronic sequence). All ITR containing plasmids were tested for PAH protein production and activity in vitro with transient transfection into human liver line, Huh7 cells, PAH Western and activity performed as previously described (Singh 2021). All XL32.1 capsid vectors were produced by triple transfection as described above. The vector for the 4-month efficacy study was purified by affinity column followed by CsCl gradient. The vector for the 1 and 4-month efficacy study was purified by affinity column followed by CsCl gradient. All vector lots were quantitated by qPCR to BGHpA (Nambiar 2017).

Efficacy testing in PAH-KO mouse for 4-months. Efficacy testing was performed as described in Example 4. All animals were perfused with PBS via the left cardiac ventricle before tissue collection.

Blood and tissue analyses. Blood and tissue analyses was performed as described in Example 4. Copies of vector DNA in livers were quantitated by qPCR in liver (Nambiar 2017). PAH protein activity and PAH protein detection in liver homogenates was performed as previously described (Heintz 2012, Nambiar 2017) and normalized by total protein (BCA protein assay kit; Pierce). The formalin fixed paraffin embedded livers were used for PAH IHC as described in Singh 2021. For digital quantification of percent IHC positive cells, VISIOPHARM™ image analysis software (version 2020.08) was used to analyze the IHC slides and measurement of regions of interest (ROIs) in the whole liver slide images. A perimeter of 3 m from the nuclei was drawn to measure the PAH staining intensity and classify each cell as either PAH positive or negative. The formalin fixed paraffin embedded liver sections were also used for detection of vector DNA and transcripts in select animals by in situ hybridization using BASESCOPE™ Duplex Reagent Kit at Advanced Cell Diagnostics, Inc (ACD) in a manual mode according to their protocol. The ISH staining on the whole section was analyzed using HALO ISH image analysis module (v4.1). The endpoints quantitated were % of vector DNA and mRNA positive cells.

Brain imaging. Brain white matter content was analyzed in live animals at various timepoints by as described in Singh 2021. The region of interest around the brain and visible corpus callosum structure was drawn across the coronal slices to calculate the corpus callosum volume.

Animal behavior assay. Animal behavior has assessed as described in Example 4.

Graphing and statistical analysis. All the data was graphed using GRAPHPAD PRISM™ (version 8.0.2) or Excel (Microsoft). Statistical analysis was performed using one-way ANOVA in GRAPHPAD PRISM™ using Tukey's multiple comparison.

Results

Figure 11A:
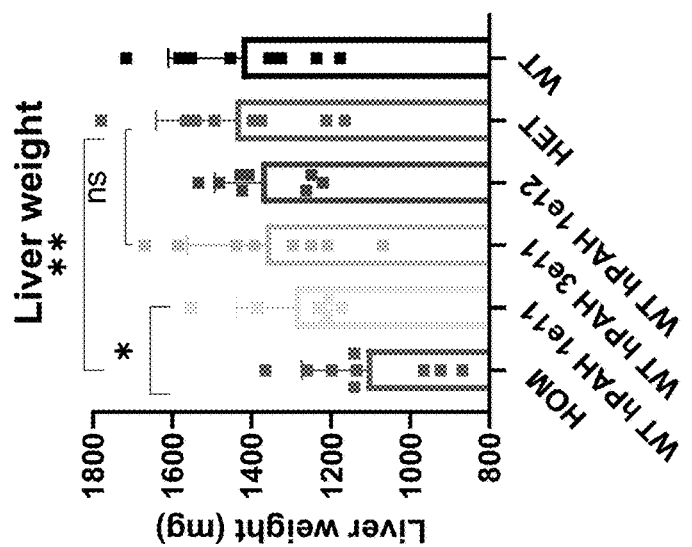
FIGS. 11A-11C show animal growth during the 4-month study post AAVXL32.1/WT hPAH administration to Pah-KO mice.
Figure 11B:
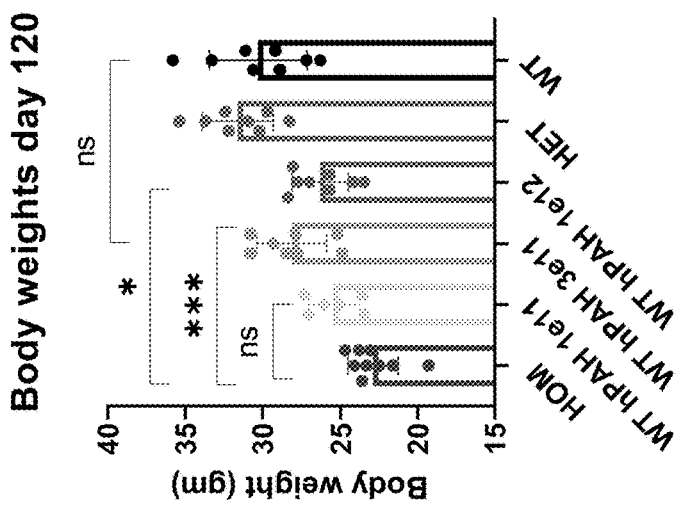
Figure 11C:
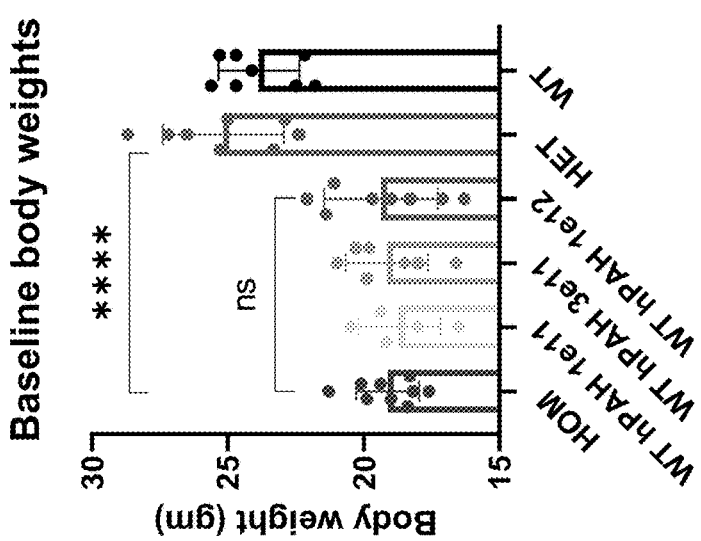

Effect of XT32.1 WT PAH Gene Transfer on Health, Blood Phe Levels and Liver PAH Correction after 4-Months of Treatment A Pah-KO model lacking any PAH protein production was used to test efficacy of XL32.1/WT PAH vector after IV delivery and efficacy was evaluated for 4-months. The vector doses tested were 1e11, 3e11 and 1e12 vg/mouse which translated to approximately 5e12, 2e12 and 5e13 vg/kg. The animal body weights were assessed throughout the study to monitor growth during the 4-month study. The animals were weighed 8 days prior to dosing to establish baseline body weights and then at the end of the study on day 120 post vector delivery (FIGS. 11A, 11B). All Pah-KO mice treated with XL32.1/WT PAH increased their bodyweight with an average increase of 130 to 145%. Treatment also increased liver weights of PAH-KO mice with weights reaching those in HET and WT mice in all treatment groups (FIG. 11C). Hence, expression of PAH in liver provided a significant growth and health improvement for the treated mice.

Figure 12A:
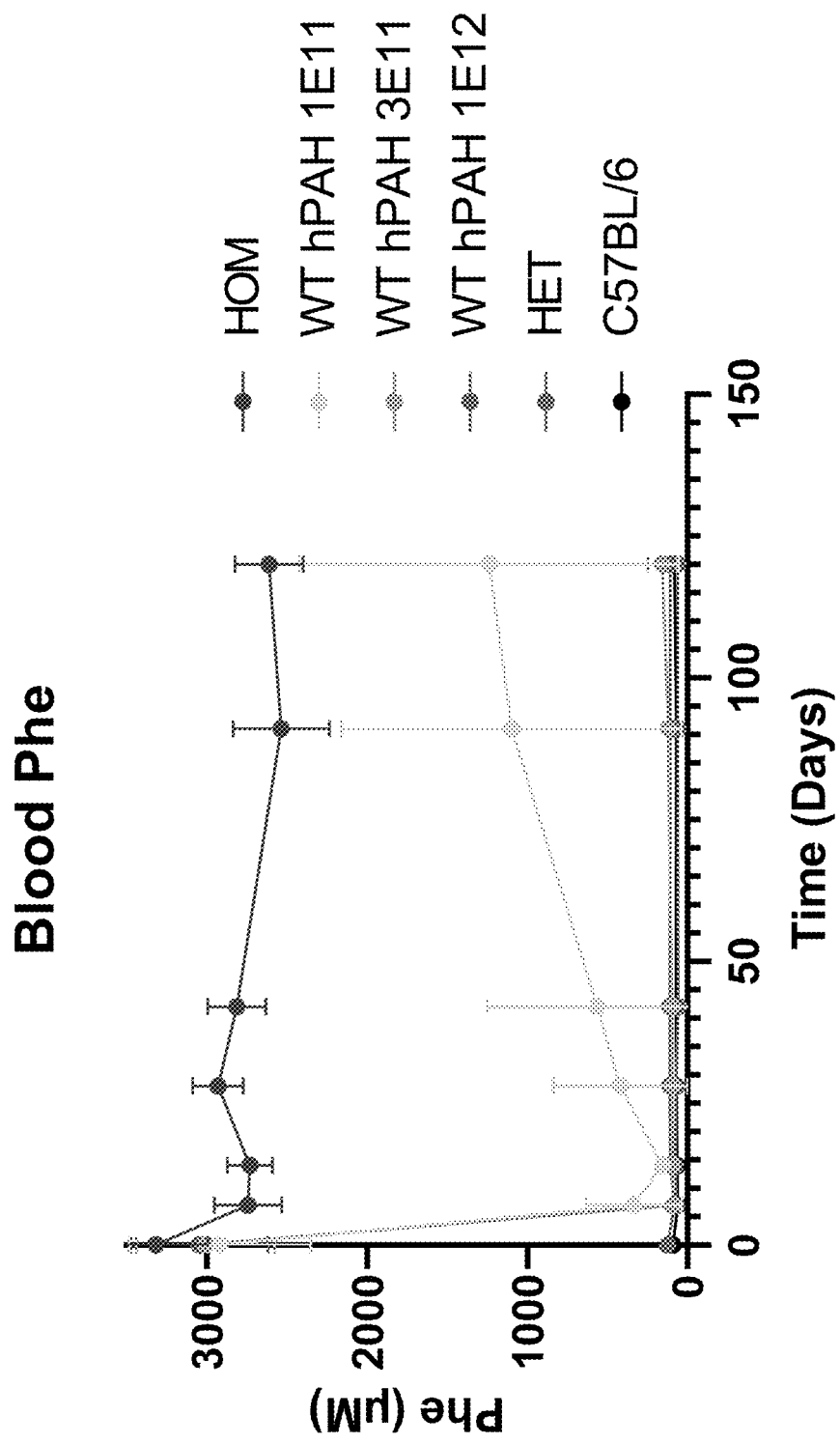
FIGS. 12A-12C shows plasma Phe levels during the 4-months study post AAVXL32.1/WT hPAH administration to Pah-KO mice.
Figure 12B:
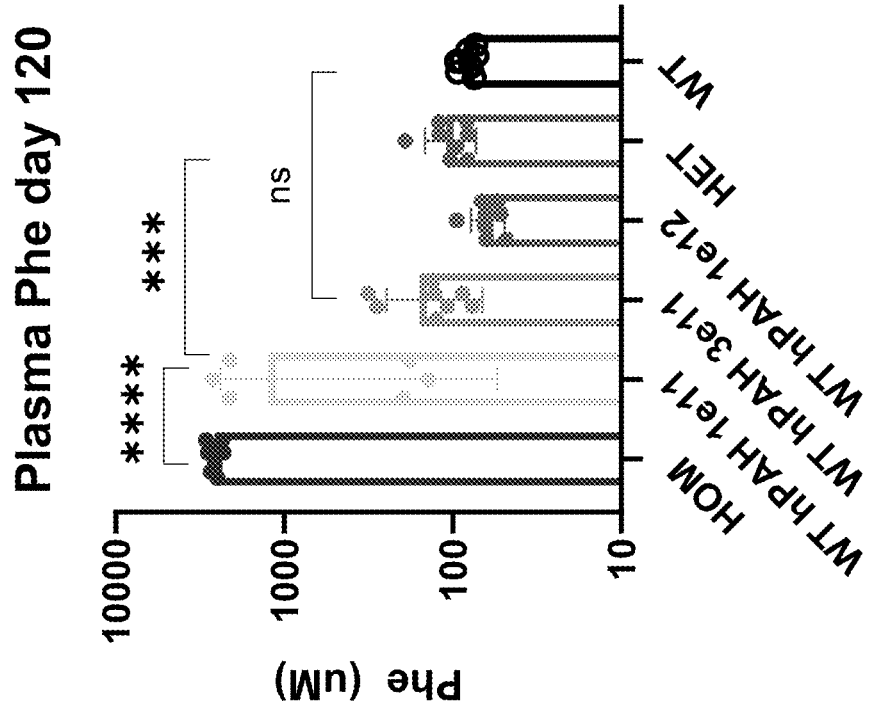
Figure 12C:
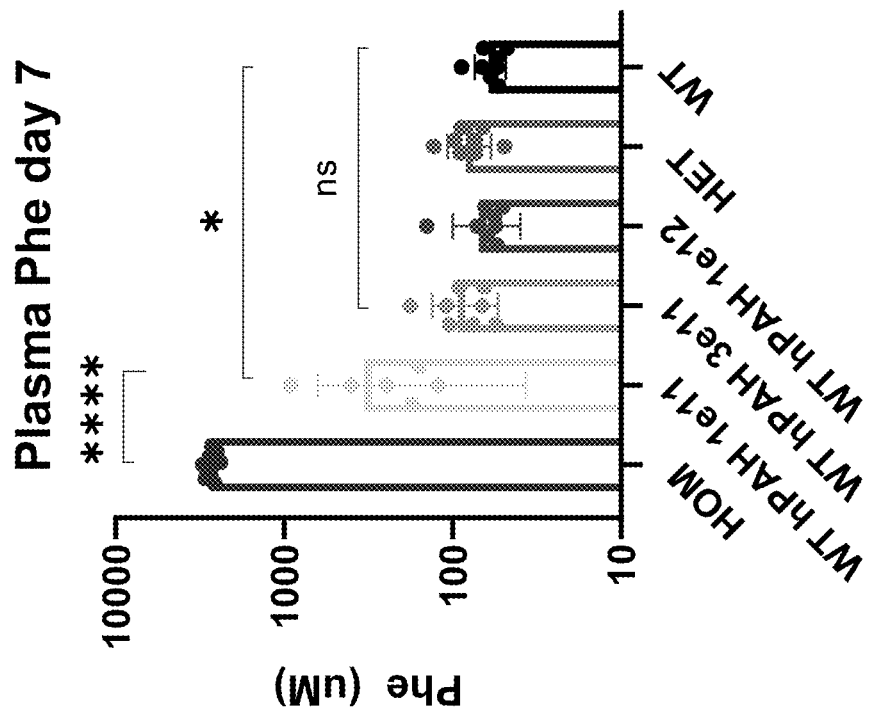

The XL32.1/WT hPAH vector delivery to liver resulted in reduced blood Phe levels (FIGS. 12A-12C). The data demonstrated rapid reduction in blood Phe levels in treatment cohorts as day 7 Phe levels were 337±123 µM (1e11 vg/mouse), 94±14 µM (3e11 vg/mouse) and 70±11 µM (1e12 vg/mouse) compared to naïve Pah-KO mice (2742±70 µM). These were comparable to Phe levels in HET and WT mice (84±9 and 62±5 µM, respectively) (FIG. 12B). On day 120, the blood Phe levels in untreated Pah-KO were 2612±71 µM and the average of Phe levels in treatment cohorts were 1237±483 µM (1e11 vg/mouse), 158±32 µM (3e11 vg/mouse) and 64±5 µM (1e12 vg/mouse). The Phe levels in the two higher dose cohorts were not significantly different to Phe levels in HET (110±13 µM) and WT (82±3 µM) mice (FIG. 12C). Hence, the middle and high dose vector cohorts (3e11 and 1e12 vg/mouse) provided sustained normalization of the blood Phe levels. The lowest dose (1e11 vg/mouse) showed variability with three of the six mice exhibiting normal blood Phe levels. The remaining 3 animals had initially reduced blood Phe levels but the effect was not sustained.

Figure 13B:
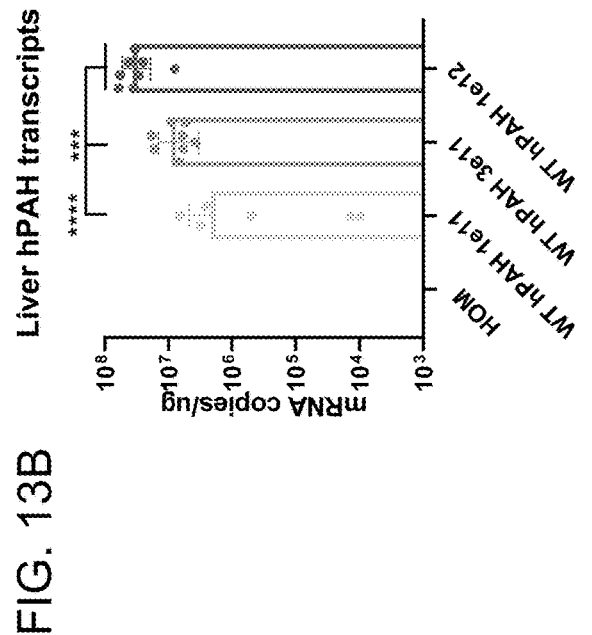
FIGS. 13A-13E show vector DNA and mRNA in livers 4-months post AAVXL32.1/WT hPAH administration to Pah-KO mice.
Figure 13A:
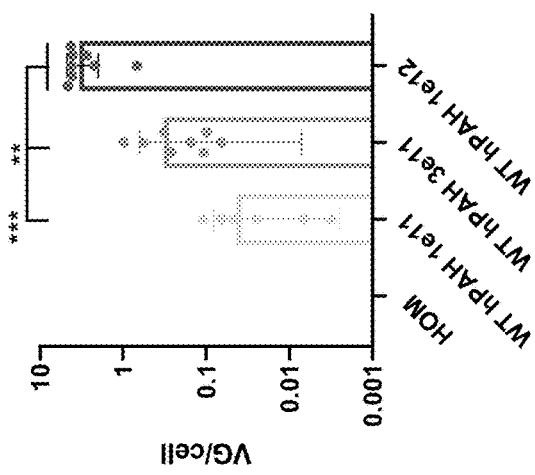
Figure 13C:
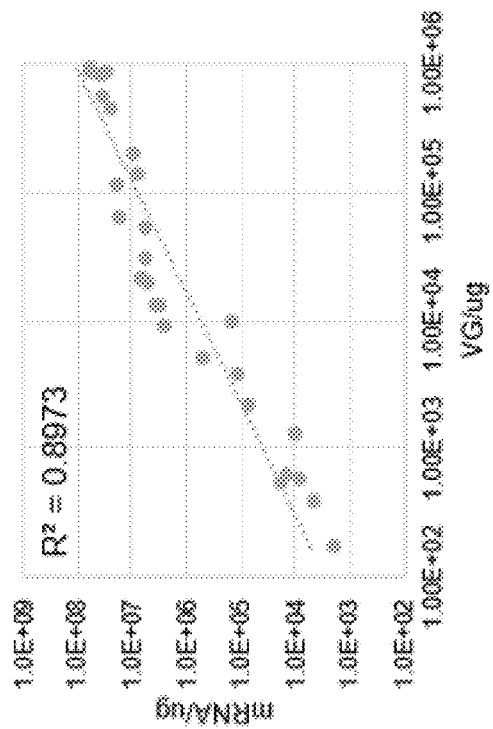
Figure 13E:
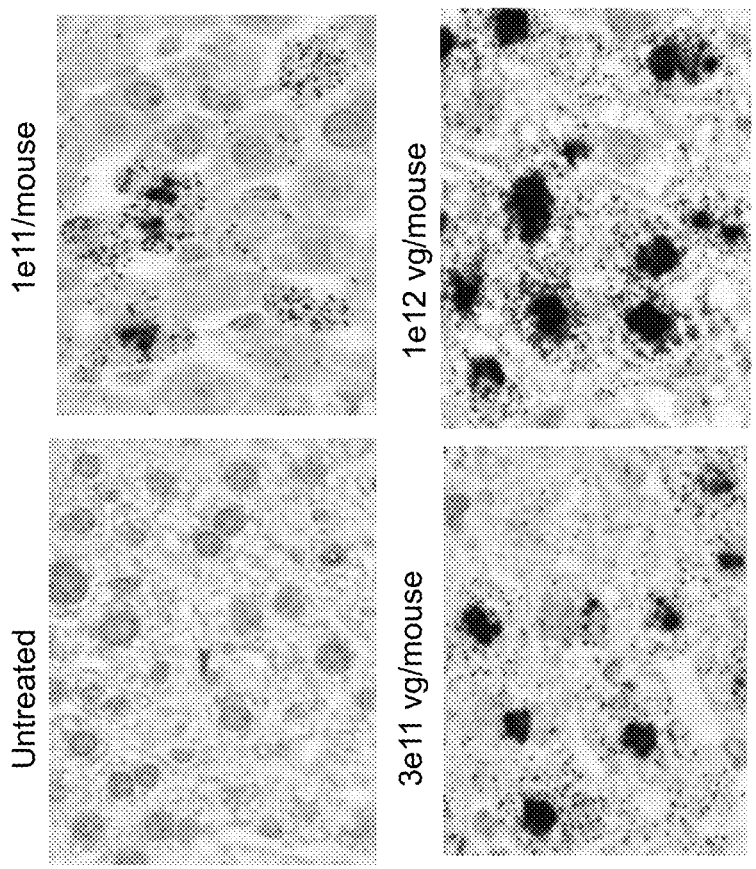
Figure 13D:
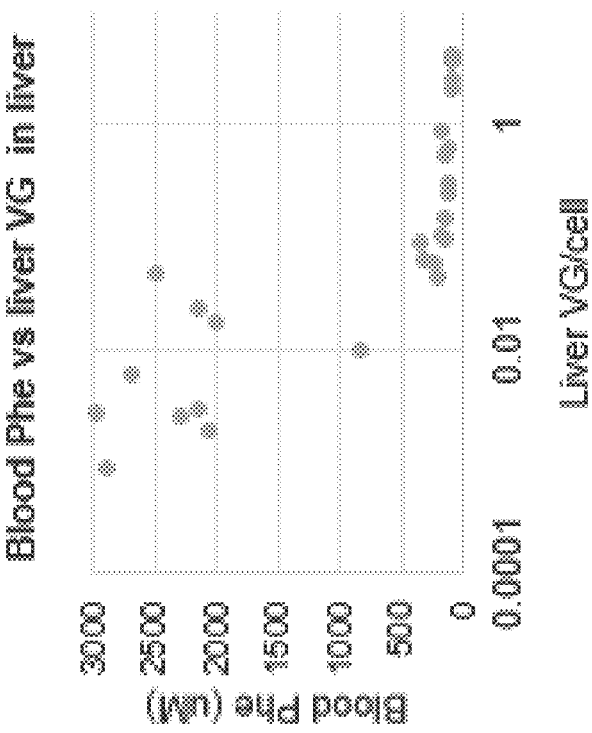

Livers of treated mice were evaluated for gene transfer efficiency and liver transduction. The vector DNA was detected in a dose-dependent manner in livers with 1e11, 3e11 and 1e12 vg/mouse cohorts resulting on average vg/cells levels as follows: 0.042 vg/cell±0.02, 0.321 vg/cell±0.111 and 3.40 vg/cell±0.49, respectively (FIG. 13A). Quantitation of vector derived mRNA in liver demonstrated on average 2.1e6±1.0e6, 9.0e6±2.0e6 and 3.7e7±0.6e7 mRNA copies/μg RNA, respectively, in each dose cohorts (FIG. 13B). This is approximately 4-fold increases in expression with each dose. There was a good correlation with vector DNA and mRNA level ($R^2=0.90$) (FIG. 13C). Correlation of vg copies/cell to blood Phe levels demonstrated that a minimum 0.1 vg/cell was required for blood Phe normalization (FIG. 13D). The vector DNA analysis in the low dose cohort revealed that the three animals with blood Phe normalization contained 0.1 vg/cell while the remaining three animals with increased Phe levels over time had less than 0.1 vg/cell. The vector uptake and gene expression were also confirmed by in situ hybridization for vector DNA and vector derived transcripts and representative images are shown in FIG. 13E.

Figure 14A:
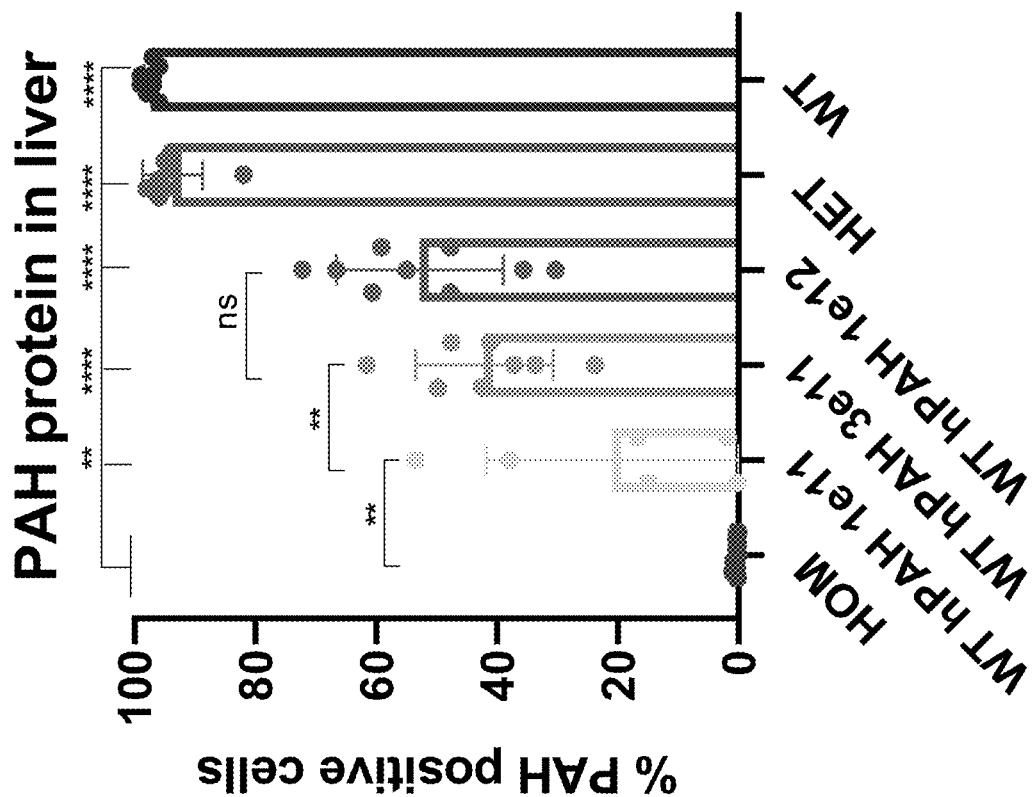
FIGS. 14A-14D shows PAH activity and PAH protein detection in livers 4-months post AAVXL32.1/WT hPAH administration to Pah-KO mice.

The functionality of vector expressed PAH was tested by measuring PAH activity in livers. The PAH activity was measured by quantitating Phe conversion into Tyr by MS-based assay. The PAH activity in the three treatment cohorts (low to high dose) were 11.5±7.9 μM (n=6), 42.8±12.4 μM (n=8) and 168.2±21.4 μM (n=8) $^{13}$C-Tyr/mg protein (FIG. 14A). For comparison, the PAH activity in HET and WT animals was 63.7±5.9 μM (n=6) and 111.8±9.9 μM (n=6) while no PAH activity was detected in the untreated Pah-KO mice (HOM, n=7). The assay demonstrated that three animals with no detectable PAH activity in the low dose cohort where the same animals that had very low vector DNA and mRNA copies. The PAH activity correlated well with vector transcript levels ($R^2=0.88$; not shown).

Figure 14B:
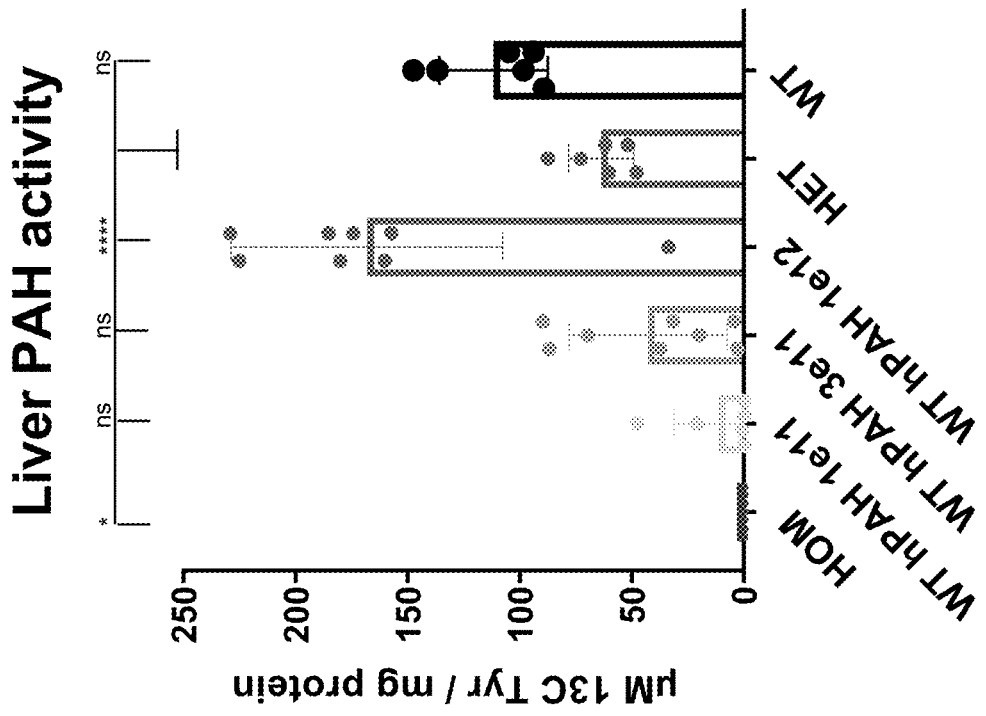
Figure 14C:
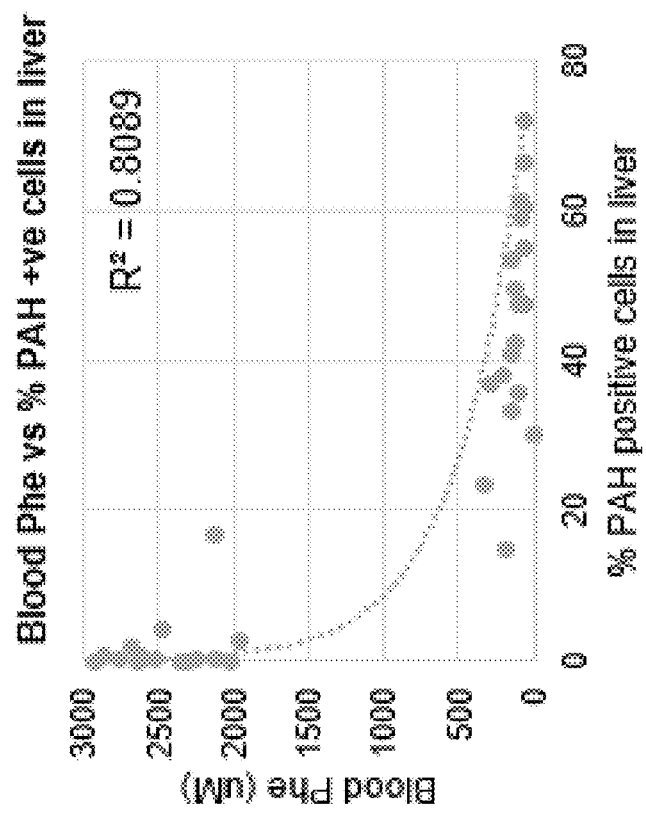
Figure 14D:
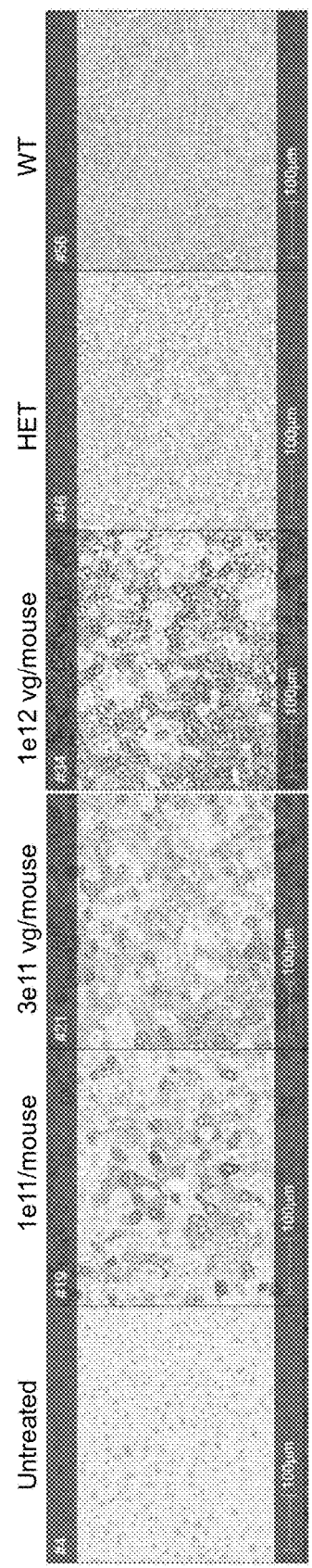

To understand the level of PAH positive cells in the liver, liver sections were evaluated by IHC using anti-PAH antibody. The average PAH positive cells in liver in each treatment cohorts were grp. 1 (HOM), 0.4±0.1%, grp 2 (low) 21.0±8.6%, grp 3 (med) 42.2±4.0%, grp 4 (high) 52.8±4.6%, grp 5 (HET) 93.6±1.7% and grp 6 (WT) 97.4±0.4% (WT) (FIG. 14B). The data showed that approximately 20% of PAH positive liver were required for blood Phe normalization (FIG. 14C). The 20% PAH positive liver requirement is consistent with the published liver repopulation results by Hamman et al. (2011) who demonstrated that a minimum of 10% of wild-type or heterozygous hepatocytes in a hepatocyte transplantation experiment was needed to normalize blood Phe levels in Pahenu2 mice. Representative images of PAH IHC showed that staining intensity increased with increasing dose of vector encoding WT PAH (FIG. 14D). The PAH staining showed uneven staining pattern with clusters of highly positive cells dispersed among negative cells in the treated livers. This was in contrast to staining observed in HET and WT livers where the staining intensity was uniform throughout the liver section (FIG. 14D).

Figure 15A:
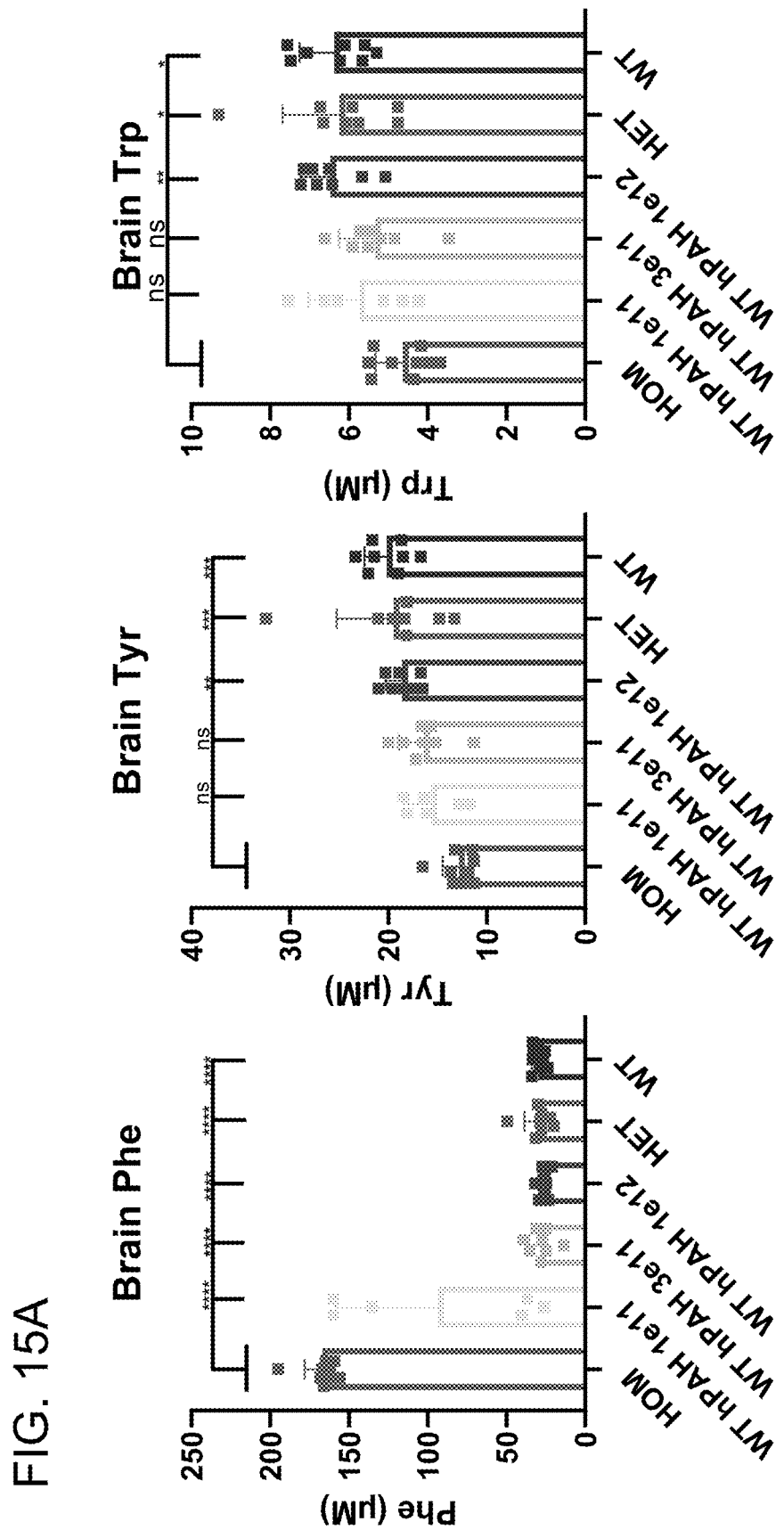
FIGS. 15A and 15B show brain amino acid and neurotransmitter levels 4 months post AAVXL32.1/WT hPAH administration to Pah-KO mice.

Effect of XL32.1 WT PAH on Brain Amino Acid, Neurotransmitter Levels and White Matter Content High blood Phe causes neurotoxicity due to increased Phe uptake into brain. High blood Phe levels can also reduce uptake of other large neutral amino acids (Tyr, Trp) into brain due use of same amino acid transporter (LAT1). Our data demonstrated that each treatment cohorts reduced brain Phe levels with low dose showing variable efficacy (FIG. 15A). The average brain Phe levels were grp. 1 (HOM), 167±4 μM, grp 2 (low) 94±27 μM, grp 3 (med) 28±3 μM, grp 4 (high) 26±1 μM, grp 5 (HET) 30±3 μM and grp 6 (WT) 30±1 μM. All except the low dose WT PAH vector cohorts normalized brain Phe levels comparable to that of HET and WT mice. Blood Phe lowering also improved Tyr levels in the brain: grp. 1 (HOM), 13±1 μM, grp 2 (low) 16±1 μM, grp 3 (med) 16±1 μM, grp 4 (high) 19±1 μM, grp 5 (HET) 20±2 μM and grp 6 (WT) 20±1 μM. The Trp transport to brain was also improved; the average Trp levels in each treatment grps were grp. 1 (HOM) 4.6±0.2 μM, grp 2 (low) 5.7±0.5 μM, grp 3 (med) 5.4±0.3 μM, grp 4 (high) 6.5±0.3 μM, grp 5 (HET) 6.3±0.5 μM and grp 6 (WT) 6.4±0.3 μM. However, a significant treatment effect in brain Tyr and Trp levels were only seen with the highest dose.

Figure 15B:
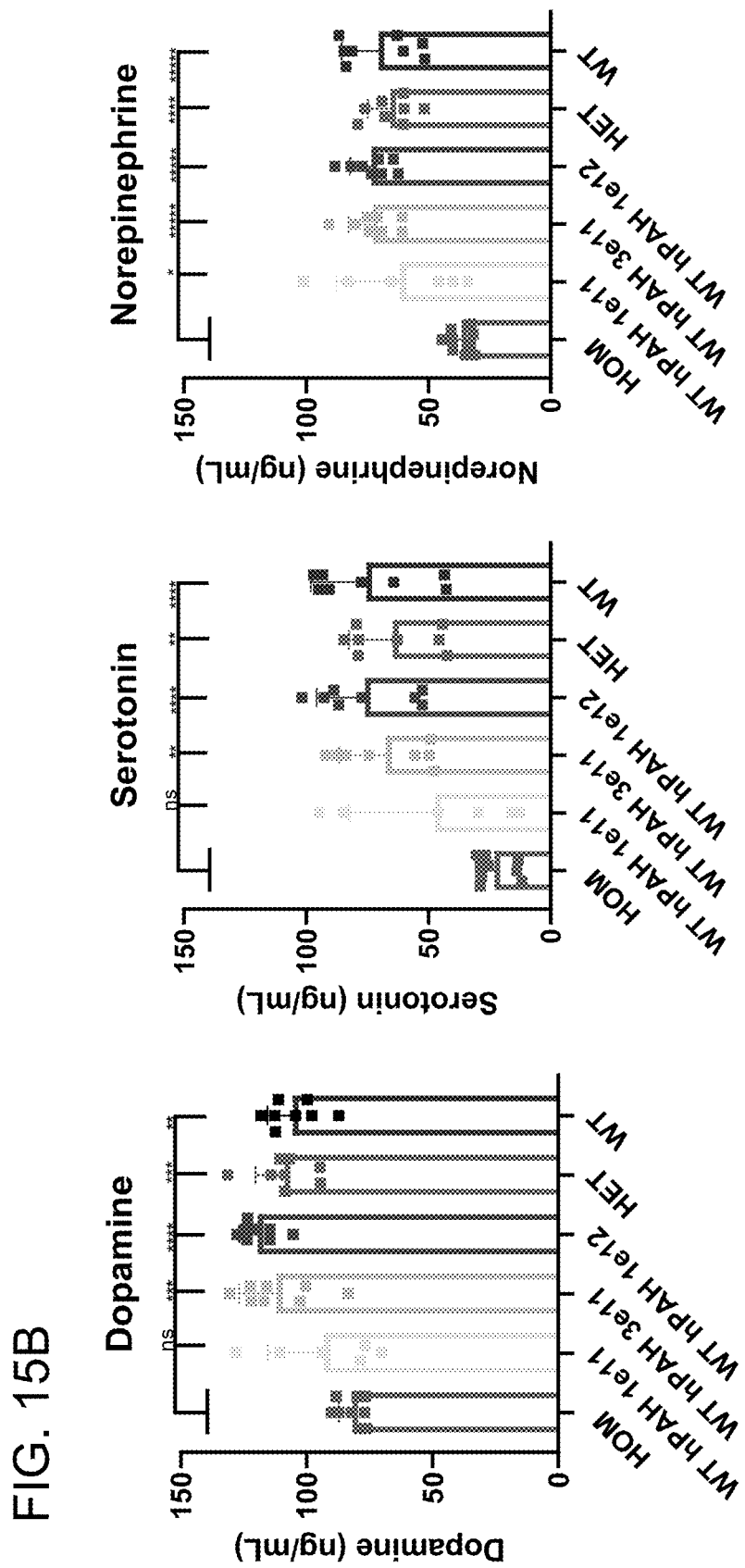

Neurotransmitter levels dopamine and serotonin are reduced in the brains of PKU patients. Both substrate deficiency (Tyr, Trp) as well as Phe toxicity on synthesis on these neurotransmitters have been proposed as explanations. Data here demonstrated that PAH gene delivery to liver improved both neurotransmitter dopamine and serotonin levels in the brain (FIG. 15B). Treatment with 3e11 and 1e12/mouse doses normalized the neurotransmitter levels comparable to that in HETs and WT mice while variability was observed in the low dose cohort. The variability in low dose cohort (1e11 vg/mouse) correlated to their gene transfer efficiency and subsequent Phe control (3 efficacious and 3 non-efficacious animals). Correlation analysis of dopamine and serotonin levels to brain Phe or their substrate levels (Tyr for dopamine and Trp for serotonin) showed that Phe lowering provided more improvement than their amino acid substrate levels. Thus, dopamine production was modestly correlated with brain Tyr levels ($R^2=0.3887$) but showed better correlation to reduced Phe levels in the brain ($R^2=0.5057$). Similarly, serotonin production was less corrected to increased Trp levels in the brain ($R^2=0.1938$) but showed a tight correlation with decreasing brain Phe levels ($R^2=0.6418$.).

In vivo MRI study was performed to assess brain white matter alternations to evaluate efficacy of the treatment on brain health. The 3D volumetric MRI segmentation and measurements were applied to quantify MRI characteristic appearances in the corpus callosum. MRI analysis showed that MRI corpus callosum volume was significantly lower in Pah-KO mice compared to HET and WT mice and all Pah-KO cohorts were comparable at baseline assessment (FIG. 16A). At 106 days post treatment of Pah-KO mice, the corpus callosum volumes were increased in all dose cohorts especially when compared as percentage to the baseline of each individual animal (FIGS. 16B, 16C). However, none of the treatment cohorts corrected the corpus callosum volumes to normal levels at the day 106 timepoint; nor were the brain weights normalized with any of the treatment cohorts (FIG. 16D).

Behavior Analysis of Pah-KO Mice.

Figure 17A:
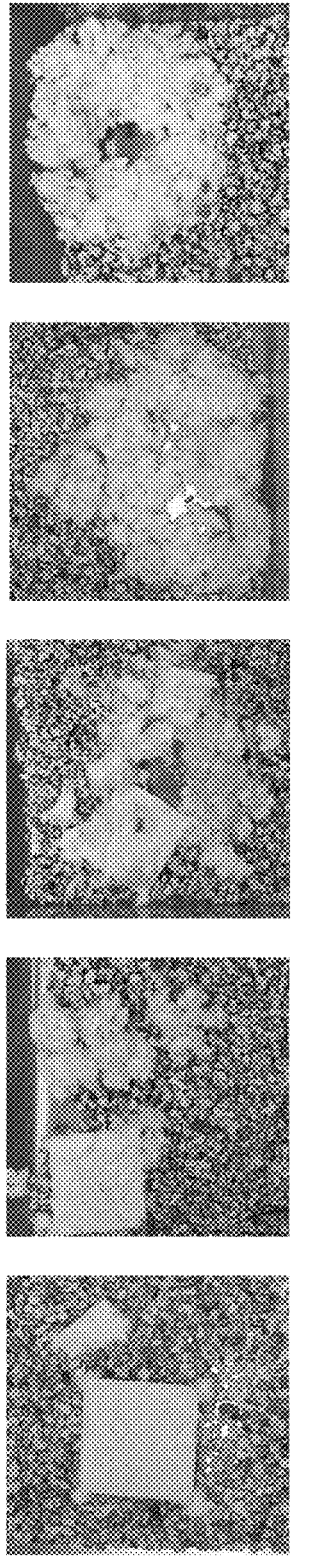
FIGS. 17A and 17B show behavioral analysis during the 4-month study post AAVXL32.1/WT hPAH administration to Pah-KO mice.
Figure 17B:
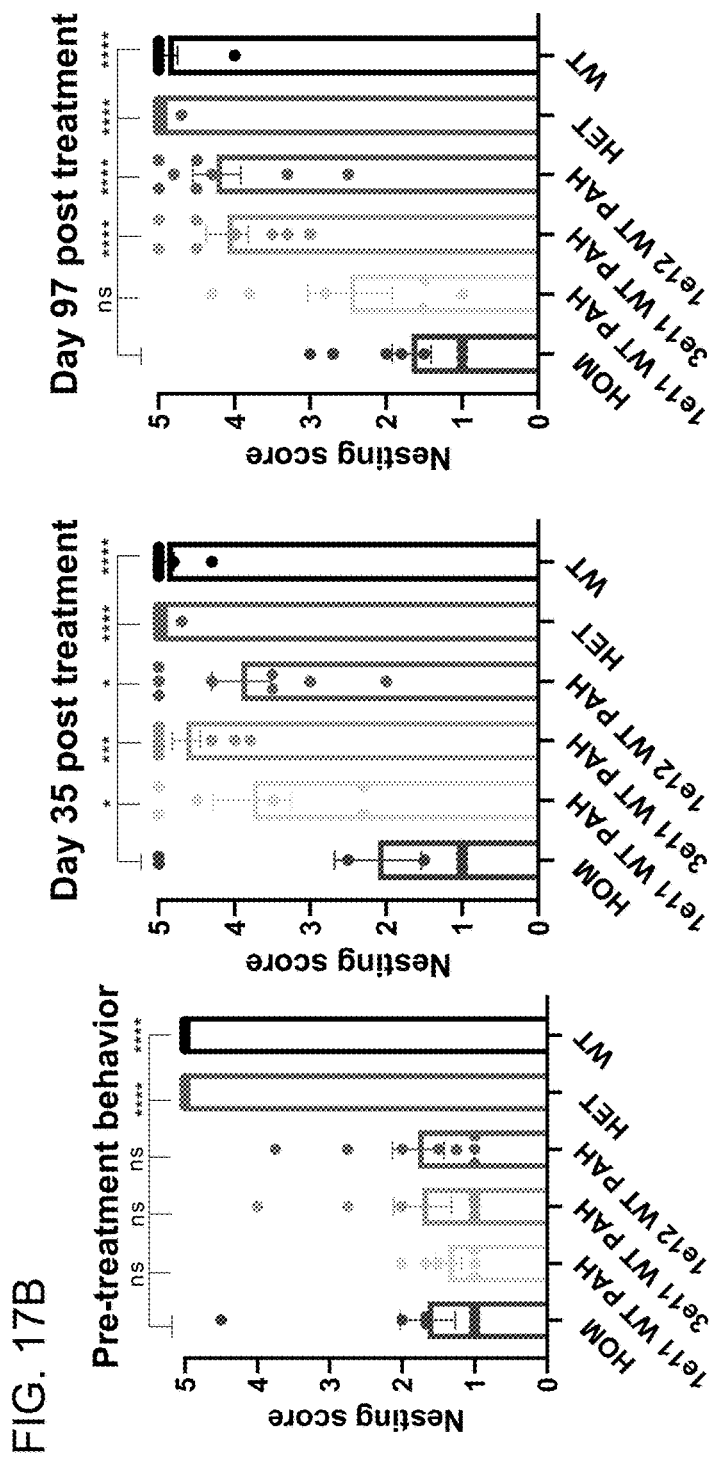

PKU patients suffer from higher rate of anxiety, depression and motor tremors. A behavior assay measuring the ability of mice to generate nests has been used to measure these issues (Deacon et al., 2006). Normal animals will tear apart a padding material and organize it into a circular and raised shape nests while animals suffering from depression will use none or very little of this material. The nesting scoring used is shown in FIG. 17A. Prior to treatment, the scores were: grp. 1 (HOM), 1.7±0.4, grp 2 (low) 1.4±0.2, grp 3 (med) 1.7±0.4, grp 4 (high) 1.8±0.4, grp 5 (HET) 5.0±0.0 and grp 6 (WT) 5.0±0.0 and there were no significant differences among the untreated Pah-KO mice cohorts (FIG. 17B). Thirty-five days post-treatment the nesting scores improved significantly among the treated Pah-KO mice with the grp averages as grp. 1 (HOM), 2.1±0.6, grp 2 (low) 3.8±0.5, grp 3 (med) 4.6±0.2, grp 4 (high) 3.9±0.4, grp 5 (HET) 5.0±0.0 and grp 6 (WT) 4.9±0.1. The treated Pah-KO mice were not significantly different from the scores in HET and WT mice. On day 97, the grp averages were similar to day 35 and as follows: grp. 1 (HOM), 1.7±0.3, grp 2 (low) 2.5±0.6, grp 3 (med) 4.1±0.3, grp 4 (high) 4.±0.3, grp 5 (HET) 5.0±0.0 and grp 6 (WT) 4.9±0.1. All but the low treatment group were significantly improved compared to untreated Pah-KO mice. Similarly, all but the low dose cohort were not significantly different from the HET or WT mice.

SUMMARY

Gene therapy by transfer of functional Pah gene to liver to correct defective PAH activity in livers of PKU patients is an attractive strategy to provide long-term Phe control for PKU patients. Our data demonstrated that an rAAV vector consisting of XL32.1 capsid and expressing WT hPAH from an optimized liver expression cassette (mA1MB2-mTTR482-HI2) was able to correct multiple PKU related pathologies in Pah-KO mice, a model of human PKU, during the 4-month duration of the study. Systemic delivery of this vector resulted in a dose-dependent increase of vector DNA, vector derived mRNA, PAH protein and PAH activity in the livers of Pah-KO mice. All three vector doses tested (approximately 5e11, 2e13 and 5e13 vg/kg) reduced blood Phe levels though variability was observed in the lowest dose cohort. Correction of blood Phe levels to various study endpoints indicated that the therapeutic benefit for the 4-month study duration required maintenance of a minimum of 0.1 vector DNA/cell, $3\times10^6$ mRNA/µg RNA and 20% of PAH positive liver to allow blood Phe normalization. The 20% PAH positive liver requirement is similar with the published liver repopulation results by Hamman et al. (16) who demonstrated that transplantation of a minimum of 10% of wild-type or heterozygous hepatocytes was needed to normalize blood Phe levels in Pahenu2 mice. The present examples also demonstrated sustained improvement in brain health with normalized amino acid transport, neurotransmitter dopamine and serotonin levels and increased brain corpus callosum volume for 4-months. These biochemical changes correlated to improvement of behavior of the mice; the benefit was already observed 35 days post treatment and was maintained until the later time point (day 97). Interestingly, three animals in the low dose group with lack of sustained Phe control demonstrated poorer values in all endpoints measured suggesting a correlation with blood Phe and disease pathology. Furthermore, normalization of blood Phe increased the body weights of the treated animals highlighting a major impact of hyperphenylalanemia on overall growth and metabolism of the PKU animals. This growth was reflected in increase of liver weights to levels of WT and HET mice implicating proliferation of hepatocytes. Despite this, the medium and high vector cohorts maintained enough vector DNA to provide efficacy until the end of the study. Furthermore, the variability observed with the low dose 1e11 vg/mouse ($5\times10^{12}$ vg/kg) dose cohort allowed defining the threshold level of gene transfer needed in situations that might result in loss of vector genomes such as liver damage or proliferation.

In summary, the present examples demonstrated that rAAVXL32.1/WT hPAH gene transfer can reduce blood Phe levels resulting in an improved growth, increased brain white matter, brain amino acid content and neurotransmitter levels, and overall improved behavior in a sustained manner. Comparison of the lead genome (mA1MB2-mTTR482-HI2) in vivo to a liver expression cassette already used in the clinic (LP1-SI, Nathwani 2011) showed higher level of transcript and enzyme activity by the lead candidate in mouse liver. Thus, the combination of the higher expression level of the lead candidate and superior gene transfer efficiency by XL32.1 capsid allows treatment of PKU patients in the clinic with potentially lower vector doses providing improved safety aspects of the therapy. Taken together, the present examples support the use of this vector for the treatment of PKU by allowing treatment with clinically efficacious, feasible and safe AAV vector doses.

Example 6. Comparison of Liver Expression Elements In Vivo

Figure 18A:
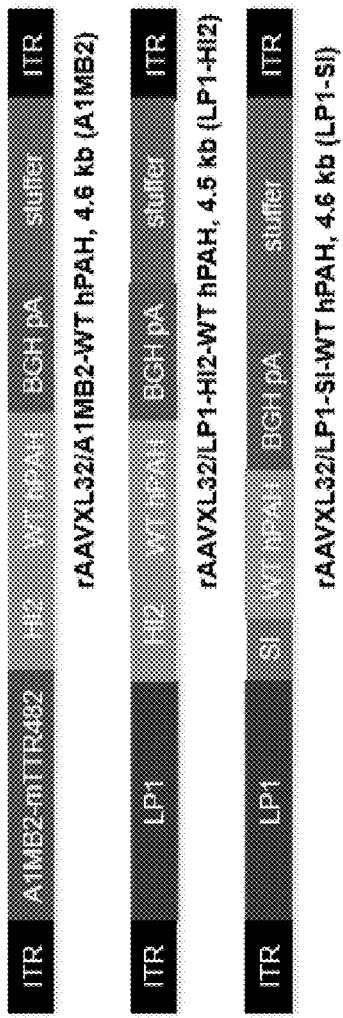
FIGS. 18A-18G show a comparison of XL32.1/WT hPAH vectors with various liver expression cassettes in vitro and in vivo.
Figure 18C:
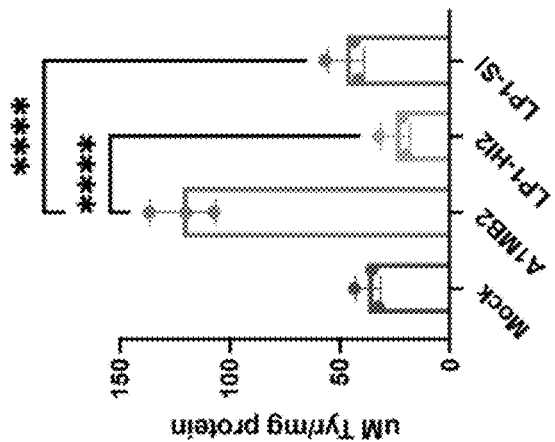
Figure 18B:
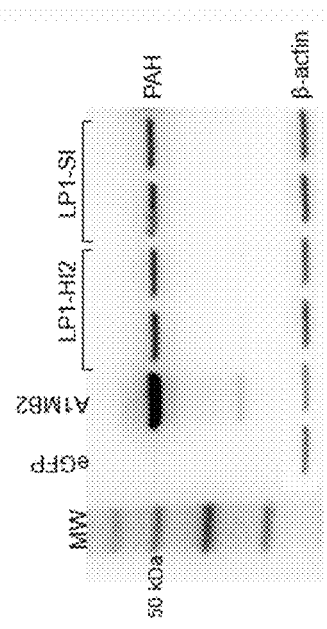
Figure 18D:
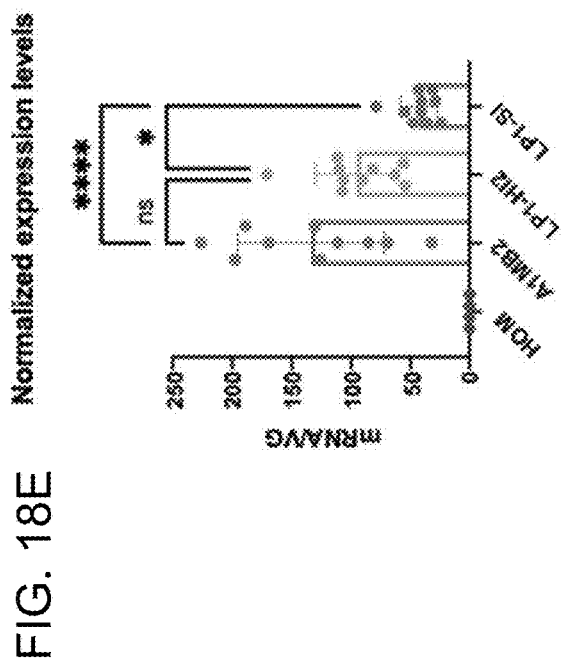
Figure 18F:
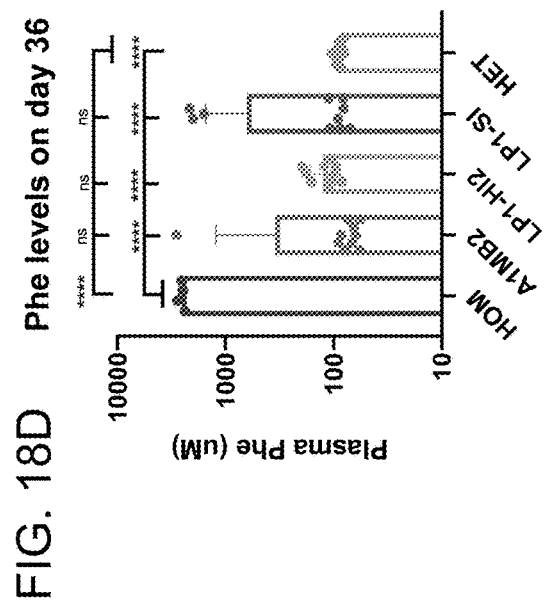
Figure 18E:
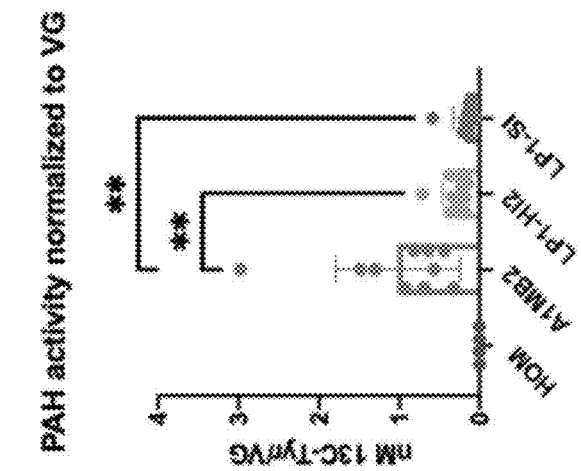
Figure 18G:
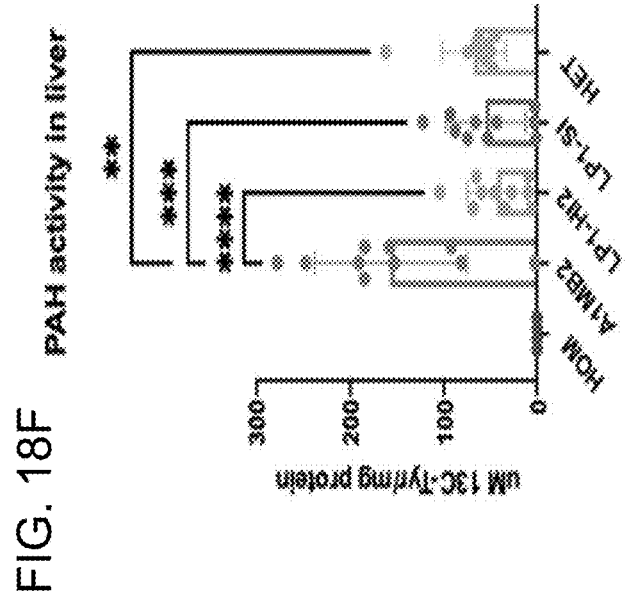

The XL32.1 vector with mA1MB2-mTTR482-HI2 used in the above 4-month study was evaluated against liver expression cassette (LP1-SI) used in a hemophilia B trial (Nathwani 2011). An intermediate construct with LP1 promoter with HI2 intron was also evaluated. (FIG. 18A). Testing of ITR containing plasmid constructs in human liver line, Huh7 cells, by transient transfection showed higher PAH protein and activity from the A1MB2 construct compared to the constructs with LP1 promoter (FIGS. 18B, 18C). The three expression cassettes packaged into XL32.1 capsids and were administered with comparable dose (3e11 vg/mouse) and evaluated for 5 weeks in Pah-KO mice. All rAAV vectors used for the expression cassette comparison were purified by CsCl gradient. All vectors significantly reduced blood Phe levels compared to that of untreated Pah-KO mice (HOM) and the Phe levels were similar to that observed in HET mice (FIG. 18D). A close-up analysis showed differences in vector expression levels. Quantitation of mRNA levels in liver showed a trend for higher expression from vector with mA1MB2-mTTR482 promoter compared to that of LP1-SI and when the transcript levels were normalized, approximately 3-fold higher levels of mRNA per VG was observed with mA1MB2-mTTR482 promoter. The average normalized RNA levels (mRNA/VG) were: A1MB2, 133.9±19.5, LP1-HI2, 95.5±11.0, and LP1-SI, 43.0±4.9 (FIG. 18E). Similarly, the liver PAH enzymatic activity was 3-fold higher in mA1MB2-mTTR482-HI2 treated animals compared to LP1-SI construct. The average liver PAH activity (µM Tyr/mg protein) for study cohort were: A1MB2, 157.4±25.7, LP1-H12, 42.9±10.2, LP1-SI, 54.9±13.4, and HET 67.8±10.9 (FIG. 18F). When the PAH activity was normalized to VG copies, this difference was 6-fold (FIG. 18G). Less difference (2-fold) was observed when activity was normalized to mRNA copies indicating the increased expression from the vector DNA was main reason for difference rather than PAH production per mRNA (not shown). Hence, the data demonstrated stronger expression in mouse liver from mA1MB2-mTTR482-H12 than from LP1-SI expression cassette.

REFERENCES

Erlandsen H, Patch M, Gamez A, Straub M, Stevens R. Structural studies on phenylalanine hydroxylase and implications towards understanding and treating phenylketonuria. Pediatrics 2003, 112:1557-1565.

Kochhar J S, Chan S Y, Ong P S, Kang L. Clinical therapeutics for phenuylketonuria. Drug Deliv Transl Res 2012, 2:223-237.

Ho G, Christodoulou J. Phenylketonuria: translating research into novel therapies. Transl Pediatr 2014, 4:49-62.

Blau N, Longo N. Alternative therapies to address the unmet medical needs of patients with phenylketonuria. Expert Opin Pharmacother 2015, 16:791-800.

Walter J H, White F J, Hall S K, MacDonald A, Rylance G, Boneh A, Francis D E, Shortland G J, Schmidt M, Vall A. how practical are recommendations for dietary control in phenylketonuria? The Lancet 2002, 360:55-56.

Waisbren S E, Noel K, Fahrbach K, Cella C, Frame D, Dorenbaum A, Levy H. Phenylalanine blood levels and clinical outcomes in phenylketonurea: a systemic literature review and meta-analysis. Mol Genet Metab 2007, 92:63-70.

Thomas J, Nguyen-Driver M, Bausell H, Breck J, Zambrano J, Birardi V. Strategies for successful ling-term engagement of adults with phenylalanine hydroxylase deficiency returning to clinic. J Inborn Errors Metabolism & Screening 5:1-9.

Anderson P J, Leuzzi V. White matter pathology in phenylketonuria. Mol Gen Metab 2010, 99:S3-S9.

Gonzales M J, Gassio R, Artuch R, Campisto J. Impaired neurotransmission in early-treated phenylketonuria patients. SeminPediatr Neurol 2016, 23:332-340.

Enns, GM, Koch R, Brumm V, Blakely E, Suter R, Jurecki E. Suboptimal outcomes in patients with PKU treated early with diet alone: revisiting the evidence. Mol. Genet. Metab. 2010, 101:99-109.

Garcia M I, Araya G, Coo S, Waisbren S E, de la Parra A. Mol Gen Metab 2017, 11:54-58.

Longo N, Harding C O, Burton B K, Grange D K, Vockley J, Wasserstein M, Rice G M, Musson D G, Gu Z, Sile S. Single-dose, subcutaneous recombinant phenylalanine ammonia lyase conjugated with polyethylene glycol in adult patients with phenylketonuria: an open-label, multicenter, phase 1 dose-escalation trial. Lancet 2014, 384: 37-44.

Harding C O, Amato R S, Stuy M, Longo N, Burton B K, Posner J, Weng H H, Merilainen M, Gu Z, Jiang J, Vockley J; PRISM-2 Investigators. Pegvaliase for the treatment of phenylketonuria: A pivotal, double-blind randomized discontinuation Phase 3 clinical trial. Mol Genet Metab 2018, March 31 (abstract)

Thomas J, Levy H, Amato S, Vockley J, Zori R, Dimmock D, Harding C O, Bilder D A, Weng H H, Olbertz J, Merilainen M, Jiang J, Larimore K, Gupta S, Gu Z, Nortrup H, PRISM investigators. Mol Genet Metab 2018, March 18 (abstract).

Oh H-J, Park E-S, Kang S, Jo I, Jung S-C. Long-term enzymatic and phenotypic correction in the phenylketonuria mouse model by adeno-associated virus vector-mediated gene transfer. Pediatric Research 2004, 56:278-284.

Mochizuki S, Mizukami H, Ogura T, Kure S, Ichinohe A, Kojima K, Matsubara Y, Kobayahi E, Okada T, Hoshika A, Ozawa K, Kuma A. Long-term correction of hyperphenylalanemia by AAV-mediated gene transfer leads to behavioral recovery in phenylketonuria mice. Gene Ther 2004, 11:1081-1086.

Ding Z, Georgiev P, Thony B. Administration-route and gender-independent long-term therapeutic correction of phenylketonuria in a mouse model by recombinant adeno-associated virus 8 pseudotyped vector-mediated gene transfer. Gene Therapy 2006, 13:587-593.

Harding C O, Gillingham M B, Hamman K, Clark H, Goebel-Daghighi E, Bird A, Koeberl D D. Complete correction of hyperphenylalaninemia following liver-directed, recombinant AAV2/8 vector-mediated gene therapy in murine phenylketonuria. Gene Therapy 2006, 13:457-462.

Yagi H, Ogure T, Mizukami H, Urabe M, Hamada H, Yoshikawa H, Ozawa K, Kume A. Complete restoration of phenylalanine oxidation in phenylketonuria mouse by a self-complementary adeno-associated virus vector. J Gene Med 2011, 13:114-122.

Yagi H, Sanechika S, Ichinose H, Sumi-Ichinose C, Mizukami H, Urabe M, Ozawa K, Kume A. Recovery of neurogenic amines in phenylketonuria mice after liver-targeted gene therapy. NeuroReport 2012, 23:30-34.

Winn S R, Scherer T, Thony B, Ying M, Martinez A, Weber S, Raber J, Harding C O. Blood phenylalanine reduction corrects CNS dopamine and serotonin deficiencies and partially improves behavioral performance in adult phenylketonuric mice. Mol Gen Metabolism 2018, 123:6-20.

Hamman, K. J, Winn S. R, Harding C O. Hepatocytes from wild-type or heterozygous donors are equally effective in achieving successful therapeutic liver repopulation in murine phenylketonuria (PKU). Mol Genet Metab 2011, 104: 235-40.

Viecelli H M, Harbottle R P, Wong S P, Schlegel A, Chuah M K, VandenDriessche T, Harding C O, Thony B. Treatment of phenylketonuria using minicircle-based naked-DNA gene transfer to murine liver. Hepatology 2014, 60:1035-1043.

Chatterjee, S., Sivanandam, V, Wong, Jr, K. K. AAV and Hematopoietic Stem Cells: The Potential of AAVHSCs in Genetic Medicines. Human Gene Ther 2020, 31: 542-552.

Sabatino, D. E., Lange, A M., Altynova, E. S., Sarkar R., Zhou, S., Merricks, E. P., Franck, H. G., Nicols, T. C., Arruda, V. R., Kazazian Jr, H. H. Efficacy and safety of long-term prophylaxis in severe hemophilia A dogs following liver gene therapy using AAV vectors. Mol Ther 2011, 19: 442-9.

Singh K, Cornell C S, Jackson R, Kabiri M, Phipps M, Desai M, et al. CRISPR/Cas9 generated knockout mice lacking phenylalanine hydroxylase protein as a novel preclinical model for human phenylketonuria. Scientific Reports 202111: 7254.

Kankaanpää, A., Meririnne, E., Ariniemi, K. & Seppälä, T. Oxalic acid stabilizes dopamine, serotonin, and their metabolites in automated liquid chromatography with electrochemical detection. J. Chromatogr. B. Biomed. Sci. Appl 2001, 753: 413-419.

Kyostio-Moore S, Berthelette P, Piraino S, Sookdeo C, Nambiar B, Jackson R, Burnham B, O'Riordan C, Cheng S H, Armentano D. The impact of minimally oversized adeno-associated viral vectors encoding human Factor VIII on vector potency in vivo. Mol Ther Methods Clin Dev 2016, 3:16006.

Nambiar B, Cornell Sookdeo C, Berthelette P, Jackson R, Piraino S, Burnham B, Nass S, Souza D, O'Riordan C R, Vincent K A, Cheng S H, Armentano D, Kyostio-Moore S. Characteristics of minimally oversized adeno-associated virus vectors encoding human Factor VIII generated using producer cell lines and triple transfection. Hum Gene Ther Methods 2017, 28:23-38.

Deacon, R. M. J. Assessing nest building in mice. Nature Protocols 2006, 1:1117-1119.

McEachern K A, Nietupski J B, Chuang W-L, Armentano D, Johnson J, Hutto E, Grabowski G A, Cheng S H, Marshall J. AAV8-mediated expression of glucocerebrosidase ameliorates the storage pathology in the visceral organs of a mouse model of Gaucher disease. J Gene Med 2006, 8:719-729.

Jacobs F, Snoeys J, Feng Y, van Craeyveld E, Lievens J, Armentano D, Cheng S H, De Geest B. Direct comparison of hepatocyte-specific expression cassettes following adenoviral hydrodynamic gene transfer. Gene Ther 2008, 15:594-603.

Kramer M G, Barajas M, Razquin N, Berraondo P, Rodrigo M, Wu C, Qian C, Fortes P, Prieto J. In vitro and in vivo comparative study of liver-specific promoters. Mol Ther 2003, 7:375-385.

Chuah M K, Petrus I, De Bleser P, Le Guiner C, Gernoux G, Adjali O, Nair N, Willems J, Evens H, Rincon M Y, Matrai J, Di Matteo M, Samara-Kuko E, Yan B, Acosta-Sanchez A, Meliani A, Cherel G, Blouin V, Christophe O, Moullier P, Mingozzi F, VandenDriessche T. Liver-specific transcriptional modules identified by genome-wide in silico analysis enable efficient gene therapy in mice and non-human primates. Mol Ther 2014, 9:1605-1613.

Wooddell C I, Reppen T, Wolff J A, Herweijer H. Sustained liver-specific transgene expression from the albumin promoter in mice following hydrodynamic plasmid DNA delivery. J Gene Med 2008, 10:551-563.

Nathwani A C, Tuddenham E G D, Rangarajan S, Rosales C, McIntosh J, Linch D C, Chowdary P, Riddell A, Jaquilmac A, Harrington C, O'Beirne J, Rustagi P, Ng C Y C, Kay M A, Zhou J, Spence Y, Morton C L, Allay J, Coleman J, Sleep S, Cunningham J M, Srivastava D, Basner-Tschakarjan E, Mingozzi F, High K A, Gray J T, Reiss U, Nienhuis A, Davidoff A M. Jiang J, Larimore K, Gupta S, Gu Z, Northrup H; PRISM investigators. Mol Genet Metab. Adeno-associated virus vector-mediated gene transfer in hemophilia B. NEJM 2011, 365:2357-2365.

Martin Martin J, Frederick A, Luo Y, Jackson R, Joubert M, Sol B, Poulin F, Pastor E, Armentano D, Wadsworth S, Vincent K. Generation and characterization of adeno-associated virus cell lines for research and preclinical vector production. Hum Gene Ther Methods 2013; 24:253-269.

McDonald J D, Charlton C K. Characterization of mutations at the mouse phenylalanine hydroxylase locus. Genomics 1996, 39:402-405.

Yew N S. Yew, Dufour E, Przybylska M, Putelat J, Crawley C, Foster M, Gentry S, Reczek D, Kloss A, Meyzaud A, Horand F, Cheng S J, Godfrin Y. Erythrocytes encapsulated with phenylalanine hydroxylase exhibit improved pharmacokinetics and lowered plasma phenylalanine levels in normal mice. Mol Gen Metab 2013, 109:339-344.

Jiang, H, Lillicrap, D, Patarroyo-White, S, et al. Multiyear therapeutic benefit of AAV serotypes 2, 6, and 8 delivering factor VIII to hemophilia A mice and dogs. Blood 2006, 108:107-115.

Park J W, Lee M H, Choi J O, Park H Y, Jung S C. Tissue-specific activation of mitogen-activated kinases for expression of transthyretin by phenylalanine and its metabolite, phenylpyruvic acid. Exp Mol Med 2010, 42:105-115.

Ledley F D, Grenett H E, Dunbar B S, Woo S L. Mouse phenylalanine hydroxylase. Homology and divergence from human phenylalanine hydroxylase. Biochem J 1990, 267:399-406.

Charron C E, Lewin A S, Laipis P J. Evidence for dominant-negative interference in the Pahenu2 mouse model of PKU. Mol Ther 2004, 9:S334.

Heintz C, Troxler H, Martinez A, Thöny B, Blau N. Heintz C, et al. Quantification of phenylalanine hydroxylase activity by isotope-dilution liquid chromatography-electrospray ionization tandem mass spectrometry. Mol Genet Metab. 2012 April; 105(4):559-65.

SEQUENCES

```
Human phenylalanine hydroxylase (GenBank AAA60082.1/NP_000268.1
protein/NM_000277.3 mRNA; WT PAH amino acid sequence with E183)
MSTAVLENPGLGRKLSDFGQETSYIEDNCNQNGAISLIFSLKEEVGALAKVLRLFEENDVNLTHIESRPS
RLKKDEYEFFTHLDKRSLPALTNIIKILRHDIGATVHELSRDKKKDTVPWFPRTIQELDRFANQILSYGA
ELDADHPGFKDPVYRARRKQFADIAYNYRHGQPIPRVEYMEEEKKTWGTVEKTLKSLYKTHACYEYNHIF
PLLEKYCGFHEDNIPQLEDVSQFLQTCTGFRLRPVAGLLSSRDFLGGLAFRVFHCTQYIRHGSKPMYTPE
PDICHELLGHVPLFSDRSFAQFSQEIGLASLGAPDEYIEKLATIYWFTVEFGLCKQGDSIKAYGAGLLSS
FGELQYCLSEKPKLLPLELEKTAIQNYTVTEFQPLYYVAESENDAKEKVRNFAATIPRPFSVRYDPYTQR
IEVLDNTQQLKILADSINSEIGILCSALQKIK (SEQ ID NO: 1)

Human WT PAH coding sequence
ATGAGCACAGCCGTGCTGGAAAACCCCGGCCTGGGCAGAAAGCTGAGCGACTTCGGCCAGGAAACCAGCTACATCGA
GGACAACTGCAACCAGAACGGCGCCATCAGCCTGATCTTCAGCCTGAAAGAAGAAGTGGGCGCCCTGGCCAAGGTGC
TGCGGCTGTTCGAGGAGAACGACGTGAACCTGACCCACATCGAGAGCCGGCCCAGCAGACTGAAGAAGGACGAGTAC
GAGTTCTTCACCCACCTGGACAAGCGGAGCCTGCCCGCCCTGACCAACATCATCAAGATCCTGCGGCACGACATCGG
CGCCACCGTGCACGAGCTGAGCCGGGACAAGAAAAAGGACACCGTGCCCTGGTTCCCCAGAACCATCCAGGAACTGG
ACAGATTCGCCAACCAGATCCTGTCCTACGGCGCCGAGCTGGATGCCGACCACCCTGGCTTCAAGGACCCCGTGTAC
CGGGCCAGACGGAAGCAGTTCGCCGATATCGCCTACAACTACCGGCACGGCCAGCCCATCCCCAGAGTCGAGTACAT
GGAAGAGGAGAAGAAAACCTGGGGCACCGTGTTCAAGACCCTGAAGTCCCTGTACAAGACCCACGCCTGCTACGAGT
ACAACCACATCTTCCCACTGCTCGAAAAGTACTGCGGCTTCCACGAGGACAATATCCCTCAGCTGGAGGACGTGTCC
CAGTTTCTGCAGACCTGCACCGGCTTCAGACTCAGGCCTGTGGCCGGCCTGCTGAGCAGCAGAGATTTTCTGGGCGG
ACTGGCCTTCCGGGTGTTCCACTGCACCCAGTACATCAGACACGGCAGCAAGCCCATGTACACCCCTGAGCCCGACA
TCTGCCACGAGCTGCTGGGACATGTGCCCCTGTTCAGCGACCGAAGCTTCGCCCAGTTCAGCCAGGAAATCGGCCTG
GCCTCTCTGGGCGCTCCCGACGAGTATATCGAGAAGCTGGCCACCATCTACTGGTTCACCGTGGAATTCGGCCTGTG
CAAGCAGGGCGACAGCATCAAGGCCTATGGCGCCGGACTCCTGTCCAGCTTCGGCGAGCTGCAGTACTGTCTGAGCG
AGAAGCCCAAGCTGCTGCCCCTGGAACTGGAAAAGACCGCCATCCAGAACTACACCGTGACCGAGTTCCAGCCCCTG
TACTACGTGGCCGAGAGCTTCAACGACGCCAAAGAAAAAGTGCGGAACTTCGCCGCCACCATCCCTCGGCCCTTCAG
CGTCAGATACGACCCCTACACCCAGCGGATCGAGGTGCTGGACAACACACAGCAGCTGAAAATTCTGGCCGACTCCA
TCAACAGCGAGATCGGCATCCTGTGCAGCGCCCTGCAGAAAATCAAGTGA (SEQ ID NO: 2)
```

SEQUENCES

XL32 & XL32.1 capsid amino acid sequence
MAADGYLPDWLEDNLSEGIREWWALKPGAPKPKANQQKQDDGRGLVLPGYKYLGPFNGLDKGEPVNAADAAALEHDK
AYDQQLQAGDNPYLRYNHADAEFQERLQEDTSFGGNLGRAVFQAKKRVLEPLGLVEEGAKTAPGKKRPVEPSPQRSP
DSSTGIGKKGQQPARKRLNFGQTGDSESVPDPQPLGEPPAAPSGVGPNTMASGGGAPMADNNEGADGVGNASGNWHC
DSTWLGDRVITTSTRTWALPTYNNHLYKQISSASTGASNDNHYFGYSTPWGYFDFNRFHCHFSPRDWQRLINNNWGF
RPKRLNFKLFNIQVKEVTTNDGVTTIANNLTSTVQVFSDSEYQLPYVLGSAHQGCLPPFPADVFMIPQYGYLTLNNG
SQAVGRSSFYCLEYFPSQMLRTGNNFTFSYTFEEVPFHSSYAHSQSLDRLMNPLIDQYLYYLNRTQNQSGSAQNKDL
LFSRGSPAGMSVQPKNWLPGPCYRQQRVSKTKTDNNNSNFTWTGASKYNLNGRESIINPGTAMASHKDDKDKFFPMS
GVMIEGKESAGASNTALDNVMITDEEEIKATNPVATEREGTVAVNLQSSSTDPATGDVHVMGALPGMVWQDRDVYLQ
GPIWAKIPHTDGHFHPSPLMGGFGLKHPPPQILIKNTPVPANPPAEFSATKFASFITQYSTGQVSVEIEWELQKENS
KRWNPEVQYTSNYAKSANVDFTVDNNGLYTEPRPIGTRYLTRPL (SEQ ID NO: 3)

XL32 capsid DNA sequence
ATGGCTGCCGATGGTTATCTTCCAGATTGGCTCGAGGACAACCTCTCTGAGGGCATTCGCGAGTGGTGGGCGCTGAA
ACCTGGAGCCCCGAAGCCCAAAGCCAACCAGCAAAAGCAGGACGACGGCCGGGGTCTGGTGCTTCCTGGCTACAAGT
ACCTCGGACCCTTCAACGGACTCGACAAGGGGGAGCCCGTCAACGCGGCGGACGCAGCGGCCTTGGAGCACGACAAG
GCCTACGACCAGCAGCTGCAGGCGGGTGACAATCCGTACCTGCGGTATAACCACGCCGACGCCGAGTTTCAGGAGCG
TCTGCAAGAAGATACGTCTTTTGGGGCAACCTCGGGCGAGCAGTCTTCCAGGCCAAGAAGCGGGTTCTCGAACCTC
TCGGTCTGGTTGAGGAAGGCGCTAAGACGGCTCCTGGAAAGAAGAGACCGGTAGAGCCATCACCCCAGCGTTCTCCA
GACTCCTCTACGGGCATCGGCAAGAAAGGCCAACAGCCCGCCAGAAAAGACTCAATTTTGGTCAGACTGGCGACTC
AGAGTCAGTTCCAGACCCTCAACCTCTCGGAGAACCTCCAGCAGCGCCCTCTGGTGTGGGACCTAATACAATGGCTT
CAGGCGGTGGCGCACCAATGGCAGACAATAACGAAGGCGCCGACGGAGTGGGTAATGCCTCAGGAAATTGGCATTGC
GATTCCACATGGCTGGGCGACAGAGTCATCACCACCAGCACCCGAACATGGGCCTTGCCCACCTATAACAACCACCT
CTACAAGCAAATCTCCAGTGCTTCAACGGGGCCAGCAACGACAACCACTACTTCGGCTACAGCACCCCCTGGGGGT
ATTTTGATTTCAACAGATTCCACTGCCATTTCTCACCACGTGACTGGCAGCGACTCATCAACAACAATTGGGGATTC
CGGCCCAAGAGACTCAACTTCAAGCTCTTCAACATCCAAGTCAAGGAGGTCACGACGAATGATGGCGTCACGACCAT
CGCTAATAACCTTACCAGCACGGTTCAAGTCTTCTCGGACTCGGAGTACCAGTTGCCGTACGTCCTCGGCTCTGCGC
ACCAGGGCTGCCTCCCTCCGTTCCCGGCGGACGTGTTCATGATTCCGCAATACGGCTACCTGACGCTCAACAATGGC
AGCCAAGCCGTGGGACGTTCATCCTTTTACTGCCTGGAATATTTCCCTTCTCAGATGCTGAGAACGGGCAACAACTT
TACCTTCAGCTACACCTTTGAGGAAGTGCCTTTCCACAGCAGCTACGCGCACAGCCAGAGCCTGGACCGGCTGATGA
ATCCTCTCATCGACCAGTACCTGTATTACCTGAACAGAACTCAGAATCAGTCCGGAAGTGCCCAAAACAAGGACTTG
CTGTTTAGCCGTGGGTCTCCAGCTGGCATGTCTGTTCAGCCCAAAAACTGGCTACCTGGACCCTGTTACCGGCAGCA
GCGCGTTTCTAAAACAAAACAGACAACAACAACAGCAACTTTACCTGGACTGGTGCTTCAAATATAACCTCAATG
GGCGTGAATCCATCATCAACCCTGGCACTGCTATGGCCTCACACAAAGACGACAAAGACAAGTTCTTTCCCATGAGC
GGTGTCATGATTTTTGGAAAGGAGAGCGCCGGAGCTTCAAACACTGCATTGGACAATGTCATGATCACAGACGAAGA
GGAAATCAAAGCCACTAACCCCGTGGCCACCGAAAGATTTGGGACTGTGGCCGTCAATCTCCAGAGCAGCAGCACAG
ACCCTGCGACCGGAGATGTGCATGTTATGGGAGCCTTACCTGGAATGGTGTGGCAAGACAGAGACGTATACCTGCAG
GGTCCTATTTGGGCCAAAATTCCTCACACGGATGGACACTTTCACCCGTCTCCTCTCATGGGCGGCTTTGGACTTAA
GCACCCGCCTCCTCAGATCCTCATCAAAAACACGCCTGTTCCTGCGAATCCTCCGGCAGAGTTTTCGGCTACAAAGT
TTGCTTCATTCATCACCCAGTATTCCACAGGACAAGTGAGCGTGGAGATTGAATGGGAGCTGCAGAAAGAAAACAGC
AAACGCTGGAATCCCGAAGTGCAGTATACATCTAACTATGCAAAATCTGCCAACGTTGATTTTACTGTGGACAACAA
TGGACTTTATACTGAGCCTCGCCCCATTGGCACCCGTTACCTCACCCGTCCCCTGTAA (SEQ ID NO: 4)

XL32.1 capsid DNA sequence
ATGGCTGCCGATGGTTATCTTCCAGATTGGCTCGAGGACAACCTCTCTGAGGGCATTCGCGAGTGGTGGGCGCTGAA
ACCTGGAGCCCCGAAGCCCAAAGCCAACCAGCAAAAGCAGGACGACGGCCGGGGTCTGGTGCTTCCTGGCTACAAGT
ACCTCGGACCCTTCAACGGACTCGACAAGGGGGAGCCCGTCAACGCGGCGGACGCAGCGGCCTTCGAGCACGACAAG
GCCTACGACCAGCAGCTGCAGGCGGGTGACAATCCGTACCTGCGGTATAACCACGCCGACGCCGAGTTTCAGGAGCG
TCTGCAAGAAGATACGTCTTTTGGGGCAACCTCGGGCGAGCAGTCTTCCAGGCCAAGAAGCGGGTTCTCGAACCTC
TCGGTCTGGTTGAGGAAGGCGCTAAGACGGCTCCTGGAAAGAAGAGACCGGTAGAGCCATCACCCCAGCGTTCTCCA
GACTCCTCTACGGGCATCGGCAAGAAAGGCCAACAGCCCGCCAGAAAAGACTCAATTTTGGTCAGACTGGCGACTC
AGAGTCAGTTCCAGACCCTCAACCTCTCGGAGAACCTCCAGCAGCGCCCTCTGGTGTGGGACCTAATACAATGGCTT
CAGGCGGTGGCGCACCAATGGCAGACAATAACGAAGGCGCCGACGGAGTGGGTAATGCCTCAGGAAATTGGCATTGC
GATTCCACATGGCTGGGCGACAGAGTCATCACCACCAGCACCCGAACATGGGCCTTGCCCACCTATAACAACCACCT
CTACAAGCAAATCTCCAGTGCTTCAACGGGGCCAGCAACGACAACCACTACTTCGGCTACAGCACCCCCTGGGGGT
ATTTTGATTTCAACAGATTCCACTGCCATTTCTCACCACGTGACTGGCAGCGACTCATCAACAACAATTGGGGATTC
CGGCCCAAGAGACTCAACTTCAAGCTCTTCAACATCCAAGTCAAGGAGGTCACGACGAATGATGGCGTCACGACCAT
CGCTAATAACCTTACCAGCACGGTTCAAGTCTTCTCGGACTCGGAGTACCAGTTGCCGTACGTCCTCGGCTCTGCGC
ACCAGGGCTGCCTCCCTCCGTTCCCGGCGGACGTGTTCATGATTCCGCAATACGGCTACCTGACGCTCAACAATGGC
AGCCAAGCCGTGGGACGTTCATCCTTTTACTGCCTGGAATATTTCCCTTCTCAGATGCTGAGAACGGGCAACAACTT
TACCTTCAGCTACACCTTTGAGGAAGTGCCTTTCCACAGCAGCTACGCGCACAGCCAGAGCCTGGACCGGCTGATGA
ATCCTCTCATCGACCAGTACCTGTATTACCTGAACAGAACTCAGAATCAGTCCGGAAGTGCCCAAAACAAGGACTTG
CTGTTTAGCCGTGGGTCTCCAGCTGGCATGTCTGTTCAGCCCAAAAACTGGCTACCTGGACCCTGTTACCGGCAGCA
GCGCGTTTCTAAAACAAAACAGACAACAACAACAGCAACTTTACCTGGACTGGTGCTTCAAATATAACCTCAATG
GGCGTGAATCCATCATCAACCCTGGCACTGCTATGGCCTCACACAAAGACGACAAAGACAAGTTCTTTCCCATGAGC
GGTGTCATGATTTTTGGAAAGGAGAGCGCCGGAGCTTCAAACACTGCATTGGACAATGTCATGATCACAGACGAAGA
GGAAATCAAAGCCACTAACCCCGTGGCCACCGAAAGATTTGGGACTGTGGCCGTCAATCTCCAGAGCAGCAGCACAG
ACCCTGCGACCGGAGATGTGCATGTTATGGGAGCCTTACCTGGAATGGTGTGGCAAGACAGAGACGTATACCTGCAG
GGTCCTATTTGGGCCAAAATTCCTCACACGGATGGACACTTTCACCCGTCTCCTCTCATGGGCGGCTTTGGACTTAA
GCACCCGCCTCCTCAGATCCTCATCAAAAACACGCCTGTTCCTGCGAATCCTCCGGCAGAGTTTTCGGCTACAAAGT
TTGCTTCATTCATCACCCAGTATTCCACAGGACAAGTGAGCGTGGAGATTGAATGGGAGCTGCAGAAAGAAAACAGC
AAACGCTGGAATCCCGAAGTGCAGTATACATCTAACTATGCAAAATCTGCCAACGTTGATTTTACTGTGGACAACAA
TGGACTTTATACTGAGCCTCGCCCCATTGGCACCCGTTACCTCACCCGTCCCCTGTAA (SEQ ID NO: 6)

SEQUENCES

Modified PrT2 enhancer sequence
GCGAGAACTTGTGCCTCCCCGTGTTCCTGACCTTTGACCCTCTGTCCTACTTAGACTAATATTGACTTTGGGTACTG
CAAACAGGAAATGGGGGAGGGATTCGATGCGAGAACTTGTGCCTCCCCGTGTTCCTGACCTTTGACCCTCTGTCCTA
CTTAGACTAATATTGACTTTGGGTACTGCAAACAGGAAATGGGGGAGGGA (SEQ ID NO: 7)
Underlined, hepatic nuclear factor binding sites; bold, modifications introduced to
generated higher affinity binding sites, italics, repeat sequence Modified A1MB2 enhancer
GGCCCCAGGTTAATTTTTAAAAAGCAGTCAAAGGTCAAAGTGGCCCTTGGCAGCATTTACTCTCTCTATTGACTTTG
GTTAATAATCTCAGGAGCACAAACATTCCTGGAGGCAGGAGAAGAAATCAACATCCTGGACTTATCCTCTGGGCCTC
TCCCCACCTTCGATGGCCCCAGGTTAATTTTTAAAAAGCAGTCAAAGGTCAAAGTGGCCCTTGGCAGCATTTACTCT
CTCTATTGACTTTGGTTAATAATCTCAGGAGCACAAACATTCCTGGAGGCAGGAGAAGAAATCAACATCCTGGACTT
ATCCTCTGGGCCTCTCCCCACC (SEQ ID NO: 8)
Underlined, hepatic nuclear factor binding sites; bold, modifications introduced to
generated higher affinity binding sites, italics, repeat sequence Modified Ealb sequence
GTTCCTAGATTACATTACACATTCTGCAAGCATAGCACAGGTCAAAGTTCAACTTTAATTACTTTCATTTTCTTGTA
TCCTCACAGCCTAGAAAATAACCTGCGTTACAGCATCCACTCAGTATCCCTTGAGCATGAGGTGACACTACTTAACA
TAGGGACGAGATGGTACTTTGTGTCTCCTGCTCTGTCAGCAGGGCACTGTACTTGCTGATACCAGGGAATATTGA**TT
TGT**AAATACCATCATTCCGAACGTGTTTGCCTTGGCCAGTTTTCCATGTACATGCAGAAAGAAGTTTGGGACTGATC
AATACAGTCCTCTGCCTTTAAAGCAATAGGAAAAGGCCAACTTGTCTACGTTTAGTATGTGGCTGTAGA (SEQ ID
NO: 9)
Underlined, hepatic nuclear factor binding sites; bold, modifications introduced to
generated higher affinity binding sites, italics, repeat sequence HEII enhancer
CCATCAGATCCTGCCCAAGGTCTTACATAAGAGGACTCTTGGACTCCCAGCAATGTCAACGACCGACCTTGAGGCCT
ACTTCAAAGACTGTGTGTTTAAGGACTGGGAGGAGCTGGGGGAGGAGATTAGGTTAAAGGTCTTTGTATTAGGAGGC
TG (SEQ ID NO: 10)

CRM8 enhancer
GGGGAGGCTGCTGGTGAATATTAACCAAGGTCACCCCAGTTATCGGAGGAGCAAACAGGGGCTAAGTCCAC (SEQ
ID NO: 11)

3'Alb stability element
CTCAATTGGATGACACTAGTCATCACATTTAAAAGCATCTCAGGTAACTATATTTTGAATTTTTTAAAAAAGTAACT
ATAATAGTTATTATTAAAATAGCAAAGATTGACCATTTCCAAGAGCCATATAGACCAGCACCGACCACTATTCTAAA
CTATTTATGTATGTAAATATTAGCTTTTAAAATTCTCAAAATAGTTGCTGAGTTGGGAACCACTATTATTTCTATCG
ATTCAGCAGCCGTAAGTCTAGGACAGGCTTAAATTGTTTTCACTGGTGTAAATTGCAGAAAGATGATCTAAGTAATT
TGGCATTTATTTTAATAGGTTTGAAAAACACATGCCATTTTACAAATAAGACTTATATTTGTCCTTTTGTTTTTCAG
CCTACCATGAGAATAAGAGAAAGAAATGAAGATCAAAAGCTTATTCATCTGTTTTTCTTTTTCGTTGGTGTAAAGC
CAACACCCTGTCTAAAAAACATAAATTTCTTTAATCATTTTGCCTCTTTTCTCTGTGCTTCAATTAATAAAAAATGG
AAAGAATCTAATAGAGTGGTACAGCACTGTTATTTTTCAAAGATGTGTTGCTATCCTGAAAATTCTGTAGGTTCTGT
GGAAGTTCCAGTGTTCTCTCTTATTCCACTTCGGTAGAGGATTTCTAGTTTCTTGTGGGCTAATTAAATAAATCATT
AATACTCTTCTAAGTTATGGATTATAAACATTCAAAATAATATTTTGACATTATGATAATTCTGAATAAAAGAACAA
AAACCATGGTATAGGTAAGGAATATAAAACATGGCTTTTACCTTAGAAAAAACAATTCTAAAATTCATATGGAATCA
AAAAAGAGCCTGCAGGTACCCT (SEQ ID NO: 12)

3'alb and SMAR stability element
CTCAATTGGATGACACTAGTCATCACATTTAAAAGCATCTCAGGTAACTATATTTTGAATTTTTTAAAAAAGTAACT
ATAATAGTTATTATTAAAATAGCAAAGATTGACCATTTCCAAGAGCCATATAGACCAGCACCGACCACTATTCTAAA
CTATTTATGTATGTAAATATTAGCTTTTAAAATTCTCAAAATAGTTGCTGAGTTGGGAACCACTATTATTTCTATCT
ACTGTTTTAATTAAAATTATCTCTAAGGCATGTGAACTGGCTGTCTTGGTTTTCATCTGTACTTCATCTGCTACCTC
TGTGACCTGAAACATATTTATAATTCCATTAAGCTGTGCATATGATAGATTTATCATATGTATTTTCCTTAAAGGAT
TTTTGTAAGAACTAATTGAATTGATACCTGTAAAGTCTTTATCACACTACCCAATAAATAATAAATCTCTTTGTTCA
GCTCTCTGTTTCTATAAATATGTACCAGTTTTATTGTTTTTAGTGGTAGTGATTTTATTCTCTTTCTATATATATAC
ACACACATGTGTGCATTCATAAATATATACAATTTTTATGAATAAAAAATTATTAGCAATCAATATTGAAAACCACT
GATTTTTGTTTATGTGAGCAAACAGCAGATTAAAAGGAATTCCTGCAGATTCAGCAGCCGTAAGTCTAGGACAGGCT
TAAATTGTTTTCACTGGTGTAAATTGCAGAAAGATGATCTAAGTAATTTGGCATTTATTTTAATAGGTTTGAAAAAC
ACATGCCATTTTACAAATAAGACTTATATTTGTCCTTTTGTTTTTCAGCCTACCATGAGAATAAGAGAAAGAAAATG
AAGATCAAAAGCTTATTCATCTGTTTTTCTTTTTCGTTGGTGTAAAGCCAACACCCTGTCTAAAAAACATAAATTTC
TTTAATCATTTTGCCTCTTTTCTCTGTGCTTCAATTAATAAAAAATGGAAAGAATCTAATAGAGTGGTACAGCACTG
TTATTTTTCAAAGATGTGTTGCTATCCTGAAAATTCTGTAGGTTCTGTGGAAGTTCCAGTGTTCTCTCTTATTCCAC
TTCGGTAGAGGATTTCTAGTTTCTTGTGGGCTAATTAAATAAATCATTAATACTCTTCTAAGTTATGGATTATAAAC
ATTCAAAATAATATTTTGACATTATGATAATTCTGAATAAAAGAACAAAAACCATGTATAGGTAAGGAATATAAAA
CATGGCTTTTACCTTAGAAAAAACAATTCTAAAATTCATATGGAATCAAAAAAGAGCCTGCAGGTACCCT (SEQ ID
NO: 13)

ITR-mA1MB2-mTTR482-HI2-WT hPAH/E-BGHpA-stuffer-ITR sequence; Coding
sequence for WT PAH is underlined
TTGGCCACTCCCTCTCTGCGCGCTCGCTCGCTCACTGAGGCCGCCCGGGCAAAGCCCGGGCGTCGGGCGACCTTTGG
TCGCCCGGCCTCAGTGAGCGAGCGAGCGCGCAGAGAGGGAGTGGCCAACTCCATCACTAGGGGTTCCTTACCGCGTG
GCCCCAGGTTAATTTTTAAAAAGCAGTCAAAGGTCAAAGTGGCCCTTGGCAGCATTTACTCTCTCTATTGACTTTGG
TTAATAATCTCAGGAGCACAAACATTCCTGGAGGCAGGAGAAGAAATCAACATCCTGGACTTATCCTCTGGGCCTCT
CCCCACCTTCGATGGCCCCAGGTTAATTTTTAAAAAGCAGTCAAAGGTCAAAGTGGCCCTTGGCAGCATTTACTCTC

SEQUENCES

```
TCTATTGACTTTGGTTAATAATCTCAGGAGCACAAACATTCCTGGAGGCAGGAGAAGAAATCAACATCCTGGACTTA
TCCTCTGGGCCTCTCCCCACCGATATCTACCTGCTGATCGCCCGGCCCCTGTTCAAACATGTCCTAATACTCTGTCG
GGGCAAAGGTCGGCAGTAGTTTTCCATCTTACTCAACATCCTCCCAGTGTACGTAGGATCCTGTCTGTCTGCACATT
TCGTAGAGCGAGTGTTCCGATACTCTAATCTCCCGGGGCAAAGGTCGTATTGACTTAGGTTACTTATTCTCCTTTTG
TTGACTAAGTCAATAATCAGAATCAGCAGGTTTGGAGTCAGCTTGGCAGGGATCAGCAGCCTGGGTTGGAAGGAGGG
GGTATAAAAGCCCCTTCACCAGGAGAAGCCGTCACACAGATCCACAAGCTCCTGCTAGCCAATTGAGTCGCTGCGCG
CTGCCTTCGCCCCGTGCCCCGCTCCGCCGCCGCCTCGCGCCGCCCCCGGCTCTGACTGACCGCGTTACTCCCAC
AGGTGAGCGGGCGGGACGGCCCTTCTCCTCCGGGCTGTAATTAGCGCTTGGTTTATTGACGGCTTGTTTCTTTTCTG
TGGCTGCGTGAAAGCCTTGAGGGGCTCCGGGAAGGCCCTTTGTGCGGGGGGAGCGGCTCGGGGGGTGCGTGCGTGTG
TGTGTGCGTGGGGAGCGCCGCGTGCGGCTCCGCGCTGCCCGGCGGCTGTGAGCGCTGCGGGCGCGGCGCGGGGCTTT
GTGCGCTCCGCAGTGTGCGCGAGGGGAGCGGGGCCGGGGGCGGTGCCCCGCGGTGCGGGGGGGGCTGCGAGGGGAAC
AAAGGCTGCGTGCGGGGTGTGTGCGTGGGGGGGTGAGCAGGGGGTGTGGGCGCGTCGGTCGGGCTGCAACCCCCCCT
GCACCCCCTCCCCGAGTTGCTGAGCACGGCCCGGCTTCGGGTGCGGGGCTCCGTACGGGGCGTGGCGCGGGGCTCG
CCGTGCCGGCGGGGGTGGCGGCAGGTGGGGGTGCCGGGCGGGGCGGGGCCGCCTCGGGCCGGGGAGGGCTCGGGG
GAGGGGCGCGGCGGCCCCCGGAGCGCCGGCGGCTGTCGAGGCGCGGCGAGCCGCAGCCATTGCCTTTTTTGGTAATC
GTGCGAGAGGGCGCAGGGACTTCCTTTGTCCCAAATCTGTGCGGAGCCGAAATCTGGGAGGCGCCGCCGCCACCCCT
CTAGCGGGCGCGGGGCGAAGCGGTGCGGCGCCGGCAGGAAGGAATTGGGCGGGAGGGCCTTCGTGCGTCGCCGCGC
CGCCGTCCCCTTCTCCCTCTCCAGCCTCGGGGCTGTCCGCGGGGGGACGGCTGCCTTCGGGGGGGACGGGGCAGGGC
GGGGTTCGGCTTCTGGCGTGTGACCGGCGGCTCTAGAGCCTCTGCTAACCTTGTTCTTGCCTTCTTCTTTTTCCTAC
AGCTCCTGGGCAACGTGCTGGTTATTGTGCTGTCTCATCATTTTGGCAAAGAATTCATTTCGAAGCCGCCACCATGA
GCACAGCCGTGCTGGAAAACCCCGGCCTGGGCAGAAAGCTGAGCGACTTCGGCCAGGAAACCAGCTACATCGAGGAC
AACTGCAACCAGAACGGCGCCATCAGCCTGATCTTCAGCCTGAAAGAAGAAGTGGGCGCCCTGGCCAAGGTGCTGCG
GCTGTTCGAGGAGAACGACGTGAACCTGACCCACATCGAGAGCCGGCCCAGCAGACTGAAGAAGGACGAGTACGAGT
TCTTCACCCACCTGGACAAGCGGAGCCTGCCCGCCCTGACCAACATCATCAAGATCCTGCGGCACGACATCGGCGCC
ACCGTGCACGAGCTGAGCCGGGACAAGAAAAAGGACACCGTGCCCTGGTTCCCCAGAACCATCCAGGAACTGGACAG
ATTCGCCAACCAGATCCTGTCCTACGGCGCCGAGCTGGATGCCGACCACCCTGGCTTCAAGGACCCCGTGTACCGGG
CCAGACGGAAGCAGTTCGCCGATATCGCCTACAACTACCGGCACGGCCAGCCCATCCCCAGAGTCGAGTACATGAA
GAGGAGAAGAAACCTGGGGCACCGTGTTCAAGACCCTGAAGTCCCTGTACAAGACCCACGCTGCTACGAGTACAA
CCACATCTTCCCACTGCTCGAAAAGTACTGCGGCTTCCACGAGGACAATATCCCTCAGCTGGAGGACGTGTCCCAGT
TTCTGCAGACCTGCACCGGCTTCGACTCAGGCCTGTGGCCGGCCTGCTGAGCAGCAGAGATTTCTGGGCGGACTG
GCCTTCCGGGTGTTCCACTGCACCCAGTACATCAGACACGGCAGCAAGCCCATGTACACCCCTGAGCCCGACATCTG
CCACGAGCTGCTGGACATGTGCCCCTGTTCAGCGACGAGACTTCGCCCAGTTCAGCCAGGAAATCGGCCTGGCCT
CTCTGGGCGCTCCCGACGAGTATATCGAGAAGCTGGCCACCATCTACTGGTTCACCGTGGAATTCGGCCTGTGCAAG
CAGGGCGACAGCATCAAGGCCTATGGCGCCGGACTCCTGTCCAGCTTCGGCGAGCTGCAGTACTGTCTGAGCGAGAA
GCCCAAGCTGCTGCCCCTGGAACTGGAAAAGACCGCATCCAGAACTACACCGTGACCGAGTTCCAGCCCCTGTACT
ACGTGCCGAGAGCTTCAACGACGCCAAAGAAAAAGTGCGGAACTTCGCCGCCACCATCCCTCGGCCCTTCAGCGTC
AGATACGACCCCTACACCCAGCGGATCGAGGTGCTGGACAACACACAGCAGCTGAAAATTCTGGCCGACTCCATCAA
CAGCGAGATCGGCATCCTGTGCAGCGCCCTGCAGAAAATCAAGTGAACTAGTCTGTGCCTTCTAGTTGCCAGCCATC
TGTTGTTTGCCCCTCCCCCGTGCCTTCCTTGACCCTGGAAGGTGCCACTCCCACTGTCCTTTCCTAATAAAATGAGG
AAATTGCATCGCATTGTCTGAGTAGGTGTCATTCTATTCTGGGGGTGGGTGGGGCAGGACAGCAAGGGGGAGGAT
TGGGAAGACAATAGCAGGCATGCTGGGGATGCGGTGGGCTCTATGGTACCACCGGTCCAGGGGTGAGTGAAGGTTTG
GAAGAGTGTAGCAGAATAAGAAACCATGAGTCCCCTCCCTGAGAAGCCCTGAGCCCCCTTGACGACACACATCCCTC
GAGGCTCAGCTTCATCATCTGTAAAAGGTGCTGAAACTGACCATCCAAGCTGCCGAAAAAGATTGTGTGGGGATAAT
TCAAAACTAGAGGAAGATGCAGAATTTCTACATCGTGGCGATGTCAGGCTAAGAGTTGCCATCGTGGCTGTCCATCG
ATTTATTGGAATCATATGTTTATTTGAGGGTGTCTTGGATATTACAAATAAATTGTTGGAGCATCAGCATATTG
GTAATTCTGTCTAAGGCTCCCTGCCCCTTGTTAATTGGCAGCTCAGTTATTCATCCAGGGCAAACATTCTGCTTACT
ATTCCTGAGAGCTTTCCTCATCCTCTAGATTGGCAGGGGAATTGCAGTTGCCTGAGCAGCCTCCCCTCTGCCATACC
AACAGAGCTTCACCATCGAGGCTTGCAGAGTGGACAGGGGCCTCAGGGACCCCTGATCCCAGCTTTCTCATTGGACA
GAAGGAGGAGACTGGGGCTGGAGAGGGAACCTGGGCCCCCACTAAGGCCACAGCAGAGCCAGGACTTTAGCTGTGCTG
ACTGCAGCCTGGCTTGCCTCCACTGCCCTCCTTTGCCTCAAGAGCAAGGGAGCCTCAGAGTGGAGGAAGCAGCCCCT
GGCCTTGCCTCCCACCTCCCCTCCCCTTTGCTGTTTTCCTGGGACAGTGGGAGCTGGCTTAGATTGCCCTGGGGCCC
CCAGGACCCTGGCATTTTAACCCCTCAGGGGCAGGAAGGCAGCCTGAGATACAGAAGAGTCCATCACCTGCTGTATG
CCACACACCATCCCCACAGTCGACATTTAAATTAGGAACCCCTAGTGATGAGTTGGCCACTCCCTCTCTGCGCGCT
CGCTCGCTCACTGAGGCCGCCCGGGCAAAGCCCGGGCGTCGGGCGACCTTTGGTCGCCCGGCCTCAGTGAGCGAGCG
AGCGCGCAGAGAGGGAGTGGCCAA (SEQ ID NO: 14)
```

Modified chicken β-actin (CBA)/rabbit β-globin hybrid /intron (HU)
```
AGTCGCTGCGCGCTGCCTTCGCCCCGTGCCCCGCTCCGCCGCCGCCTCGCGCCGCCCGCCCCGGCTCTGACTGACCG
CGTTACTCCCACAGGTGAGCGGGCGGGACGGCCCTTCTCCTCCGGGCTGTAATTAGCGCTTGGTTTATTGACGGCTT
GTTTCTTTTCTGTGGCTGCGTGAAAGCCTTGAGGGGCTCCGGGAAGGCCCTTTGTGCGGGGGGAGCGGCTCGGGGGG
TGCGTGCGTGTGTGTGCGTGGGGAGCGCCGCGTGCGGCTCCGCGCTGCCCGGCGGCTGTGAGCGCTGCGGGCGCG
GCGCGGGGCTTTGTGCGCTCCGCAGTGTGCGCGAGGGGAGCGGGGCCGGGGGCGGTGCCCCGCGGTGCGGGGGGGC
TGCGAGGGGAACAAAGGCTGCGTGCGGGGTGTGTGCGTGGGGGGGTGAGCAGGGGGTGTGGGCGCGTCGGTCGGGCT
GCAACCCCCCTGCACCCCCTCCCCGAGTTGCTGAGCACGGCCCGGCTTCGGGTGCGGGGCTCCGTACGGGGCGTG
GCGCGGGGCTCGCCGTGCCGGCGGGGGTGGCGGCAGGTGGGGGTGCCGGGCGGGGCGGGGCCGCCTCGGGCCGGG
GAGGGCTCGGGGGAGGGGCGCGGCGGCCCCCGGAGCGCCGGCGGCTGTCGAGGCGCGGCGAGCCGCAGCCATTGCCT
TTTTTGGTAATCGTGCGAGAGGGCGCAGGGACTTCCTTTGTCCCAAATCTGTGCGGAGCCGAAATCTGGGAGGCGCC
GCCGCACCCCCTCTAGCGGGCGCGGGGCGAAGCGGTGCGGCGCCGGCAGGAAGGAATTGGGCGGGAGGGCCTTCGT
GCGTCGCCGCGCCGCCGTCCCCTTCTCCCTCTCCAGCCTCGGGGCTGTCCGCGGGGGGACGGCTGCCTTCGGGGGGG
ACGGGGCAGGGCGGGGTTCGGCTTCTGGCGTGTGACCGGCGGCTCTAGAGCCTCTGCTAACCTTGTTCTTGCCTTCT
TCTTTTTCCTACAGCTCCTGGGCAACGTGCTGGTTATTGTGCTGTCTCATCATTTTGGCAAAGAATTC (SEQ ID
NO: 15)
```

0.9 kb A1AT intron stuffer sequence
```
CCAGGGGTGAGTGAAGGTTTGGAAGAGTGTAGCAGAATAAGAAACCATGAGTCCCCTCCCTGAGAAGCCCTGAGCCC
CCTTGACGACACACATCCCTCGAGGCTCAGCTTCATCATCTGTAAAAGGTGCTGAAACTGACCATCCAAGCTGCCGA
AAAAGATTGTGTGGGGATAATTCAAAACTAGAGGAAGATGCAGAATTTCTACATCGTGGCGATGTCAGGCTAAGAGT
```

| SEQUENCES |
|---|
| TGCCATCGTGGCTGTCCATCGATTTTATTGGAATCATATGTTTATTTGAGGGTGTCTTGGATATTACAAATAAATTG<br>TTGGAGCATCAGGCATATTTGGTAATTCTGTCTAAGGCTCCCTGCCCCTTGTTAATTGGCAGCTCAGTTATTCATCC<br>AGGGCAAACATTCTGCTTACTATTCCTGAGAGCTTTCCTCATCCTCTAGATTGGCAGGGGAATTGCAGTTGCCTGAG<br>CAGCCTCCCCTCTGCCATACCAACAGAGCTTCACCATCGAGGCTTGCAGAGTGGACAGGGGCCTCAGGGACCCCTGA<br>TCCCAGCTTTCTCATTGGACAGAAGGAGGAGACTGGGGCTGGAGAGGGACCTGGGCCCCACTAAGGCCACAGCAGA<br>GCCAGGACTTTAGCTGTGCTGACTGCAGCCTGGCTTGCCTCCACTGCCCTCCTTTGCCTCAAGAGCAAGGGAGCCTC<br>AGAGTGGAGGAAGCAGCCCCTGGCCTTGCCTCCCACCTCCCCTCCCCTTTGCTGTTTTCCTGGGACAGTGGGAGCTG<br>GCTTAGATTGCCCTGGGGCCCCAGGACCCTGGCATTTTAACCCCTCAGGGGCAGGAAGGCAGCCTGAGATACAGAA<br>GAGTCCATCACCTGCTGTATGCCACACACCATCCCCACAGTCGACATTTAAATT (SEQ ID NO: 16) |

What is claimed is:

1. A recombinant adeno-associated virus (rAAV) particle comprising an rAAV vector, wherein the rAAV vector comprises an expression cassette for expressing a transgene in a liver cell, wherein the expression cassette comprises a transgene operably linked to a promoter and enhancer, wherein the promoter comprises a mouse transthyretin (mTTR) promoter and the enhancer comprises one or two modified alpha1-microbikunin enhancers (mA1MB2), wherein the transgene encodes a PAH polypeptide;
wherein the AAV viral particle comprises an AAV-XL32 or an AAV-XL32.1 capsid.

2. The rAAV particle of claim 1, wherein the mTTR promoter is a mTTR482 promoter.

3. The rAAV particle of claim 1, wherein the enhancer is 5' to the mTTR promoter.

4. The rAAV particle of claim 1, wherein the expression cassette further comprises an intron.

5. The rAAV particle of claim 4, wherein the intron is a chicken β-actin/rabbit β-globin hybrid intron.

6. The rAAV particle of claim 1, wherein the expression cassette further comprises a polyadenylation signal.

7. The rAAV particle of claim 6, wherein the polyadenylation signal is a bovine growth hormone polyadenylation signal.

8. The rAAV particle of claim 1, wherein the PAH polypeptide is a wild type PAH polypeptide.

9. The rAAV particle of claim 1, wherein the PAH polypeptide is a human PAH polypeptide.

10. The rAAV particle of claim 1, wherein the PAH polypeptide comprises the amino acid sequence of SEQ ID NO:1.

11. The rAAV particle of claim 1, wherein the transgene is at least 80% identical to the nucleic acid sequence of SEQ ID NO:2.

12. The rAAV particle of claim 1, wherein the rAAV vector comprises the expression cassette flanked by one or more AAV inverted terminal repeat (ITR) sequences.

13. The rAAV particle of claim 12, wherein the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs.

14. The rAAV particle of claim 12, wherein the AAV ITRs are AAV2 ITRs.

15. The rAAV particle of claim 12, wherein the expression cassette is flanked by two AAV ITRs.

16. The rAAV particle of claim 1, wherein the vector is a self-complementing vector.

17. The rAAV particle of claim 16, wherein the vector comprises a first nucleic acid sequence encoding the PAH polypeptide and a second nucleic acid sequence encoding a complement of the PAH polypeptide, wherein the first nucleic acid sequence can form intrastrand base pairs with the second nucleic acid sequence along most or all of their length.

18. The rAAV particle of claim 17, wherein the first nucleic acid sequence and the second nucleic acid sequence are linked by a mutated AAV ITR, wherein the mutated AAV ITR comprises (1) a deletion of a D region; (2) a deletion of a portion of a D region comprising a terminal resolution sequence; or (3) a mutation of a terminal resolution sequence.

19. The rAAV particle of claim 1, wherein the rAAV vector comprises 5' to 3' an AAV2 ITR, a modified alpha1-microbikunin enhancer (mA1MB2), a mouse transthyretin (mTTR) promoter, a chicken β-actin/rabbit β-globin hybrid intron, a codon-optimized human PAH gene, a bovine growth hormone polyadenylation signal, a stuffer fragment derived from an alpha-1-antitrypsin gene and an AAV2 ITR.

20. The rAAV particle of claim 19, wherein the mA1MB2 comprises the sequence of SEQ ID NO: 8.

21. The rAAV particle of claim 19, wherein the chicken β-actin/rabbit β-globin hybrid intron comprises the sequence of SEQ ID NO: 15.

22. The rAAV particle of claim 19, wherein the stuffer fragment derived from an alpha-1-antitrypsin gene comprises the sequence of SEQ ID NO: 16.

23. The rAAV particle of claim 19, wherein the codon-optimized human PAH gene comprises the nucleic acid sequence of SEQ ID NO:2.

24. The rAAV particle of claim 19, wherein the rAAV vector comprises the nucleic acid sequence of SEQ ID NO:14.

25. The rAAV particle of claim 1, wherein the AAV capsid is an AAV-XL32 capsid.

26. The rAAV particle of claim 25, wherein the AAV-XL32 capsid comprises an AAV-XL32 capsid protein comprising an amino acid sequence at least 90%, 95%, 99% or 100% identical to SEQ ID NO:3.

27. The rAAV particle of claim 26, wherein the AAV-XL32 capsid comprises a VP1, a VP2, and a VP3, wherein the VP1, VP2, and VP3 are encoded by the nucleic acid sequence of SEQ ID NO: 4.

28. The rAAV particle of claim 1, wherein the AAV capsid is an AAV-XL32.1 capsid.

29. The rAAV particle of claim 28, wherein the AAV-XL32.1 capsid comprises an amino acid sequence at least 90%, 95%, 99%, or 100% identical to SEQ ID NO:3.

30. The rAAV particle of claim 28, wherein the AAV-XL32.1 capsid comprises a VP1, a VP2, and a VP3, wherein the VP1, VP2, and VP3 are encoded by the nucleic acid sequence of SEQ ID NO: 6.

31. A composition comprising the rAAV particle of claim 1.

32. A kit comprising the rAAV particle of claim 1.

33. The rAAV particle of claim 1, wherein the transgene comprises the nucleic acid sequence of SEQ ID NO:2.

34. The rAAV particle of claim 1, wherein the transgene is operably linked to a 3' element.

35. The rAAV particle of claim 34, wherein the 3' element is an albumin 3' element (3'Alb).

36. The rAAV particle of claim 35, wherein the albumin 3' element is linked to a human alpha 1 antitrypsin scaffold/matrix attachment region (SMAR) (3'AlbSMAR).

37. A recombinant adeno-associated virus (rAAV) particle comprising an rAAV vector, wherein the rAAV vector comprises the nucleic acid sequence of SEQ ID NO: 14, and wherein the AAV viral particle comprises an AAV-XL32 capsid protein comprising the amino acid sequence of SEQ ID NO: 3.

* * * * *

SEQUENCE LISTING

<160> NUMBER OF SEQ ID NOS: 17

<210> SEQ ID NO 1
<211> LENGTH: 452
<212> TYPE: PRT
<213> ORGANISM: Homo sapiens

<400> SEQUENCE: 1

```
Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
                20                  25                  30

Gly Ala Ile Ser Leu Ile Phe Ser Leu Lys Glu Glu Val Gly Ala Leu
            35                  40                  45

Ala Lys Val Leu Arg Leu Phe Glu Glu Asn Asp Val Asn Leu Thr His
        50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
                100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
        130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
                180                 185                 190

Thr Leu Lys Ser Leu Tyr Lys Thr His Ala Cys Tyr Glu Tyr Asn His
            195                 200                 205

Ile Phe Pro Leu Leu Glu Lys Tyr Cys Gly Phe His Glu Asp Asn Ile
        210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
                260                 265                 270

Ser Lys Pro Met Tyr Thr Pro Glu Pro Asp Ile Cys His Glu Leu Leu
```

```
                275                 280                 285
Gly His Val Pro Leu Phe Ser Asp Arg Ser Phe Ala Gln Phe Ser Gln
            290                 295                 300

Glu Ile Gly Leu Ala Ser Leu Gly Ala Pro Asp Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
                355                 360                 365

Leu Glu Lys Thr Ala Ile Gln Asn Tyr Thr Val Thr Glu Phe Gln Pro
370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
                420                 425                 430

Leu Ala Asp Ser Ile Asn Ser Glu Ile Gly Ile Leu Cys Ser Ala Leu
            435                 440                 445

Gln Lys Ile Lys
    450

<210> SEQ ID NO 2
<211> LENGTH: 1359
<212> TYPE: DNA
<213> ORGANISM: Homo sapiens

<400> SEQUENCE: 2
atgagcacag ccgtgctgga aaaccccggc ctgggcagaa agctgagcga cttcggccag      60
gaaaccagct acatcgagga caactgcaac cagaacggcg ccatcagcct gatcttcagc     120
ctgaaagaag aagtgggcgc cctggccaag gtgctgcggc tgttcgagga gaacgacgtg     180
aacctgaccc acatcgagag ccggcccagc agactgaaga aggacgagta cgagttcttc     240
acccacctgg acaagcggag cctgcccgcc ctgaccaaca tcatcaagat cctgcggcac     300
gacatcggcg ccaccgtgca cgagctgagc cgggacaaga aaaaggacac cgtgccctgg     360
ttccccagaa ccatccagga actggacaga ttcgccaacc agatcctgtc ctacggcgcc     420
gagctggatg ccgaccaccc tggcttcaag gaccccgtgt accgggccag acggaagcag     480
ttcgccgata tcgcctacaa ctaccggcac ggccagccca tccccagagt cgagtacatg     540
gaagaggaga agaaacctg gggcaccgtg ttcaagaccc tgaagtccct gtacaagacc     600
cacgcctgct acgagtacaa ccacatcttc ccactgctcg aaaagtactg cggcttccac     660
gaggacaata tccctcagct ggaggacgtg tcccagtttc tgcagacctg caccggcttc     720
agactcaggc ctgtggccgg cctgctgagc agcagagatt ttctgggcgg actggccttc     780
cgggtgttcc actgcaccca gtacatcaga cacggcagca agcccatgta cacccctgag     840
cccgacatct gccacgagct gctgggacat gtgcccctgt tcagcgacag aagcttcgcc     900
cagttcagcc aggaaatcgg cctggcctct ctgggcgctc ccgacgagta tatcgagaag     960
ctggccacca tctactggtt caccgtggaa ttcggcctgt gcaagcaggg cgacagcatc    1020
aaggcctatg gcgccggact cctgtccagc ttcggcgagc tgcagtactg tctgagcgag    1080
```

```
aagcccaagc tgctgcccct ggaactggaa aagaccgcca tccagaacta caccgtgacc   1140
gagttccagc ccctgtacta cgtggccgag agcttcaacg acgccaaaga aaaagtgcgg   1200
aacttcgccg ccaccatccc tcggcccttc agcgtcagat acgacccta cacccagcgg    1260 atcgaggtgc tggacaacac acagcagctg aaaattctgg ccgactccat caacagcgag   1320
atcggcatcc tgtgcagcgc cctgcagaaa atcaagtga                          1359
```

<210> SEQ ID NO 3
<211> LENGTH: 737
<212> TYPE: PRT
<213> ORGANISM: Artificial Sequence
<220> FEATURE:
<223> OTHER INFORMATION: Synthetic Construct

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ser Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320
```

```
Gln Val Lys Glu Val Thr Thr Asn Asp Gly Val Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Glu Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Asn
            435                 440                 445

Arg Thr Gln Asn Gln Ser Gly Ser Ala Gln Asn Lys Asp Leu Leu Phe
        450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
                485                 490                 495

Asn Asn Asn Ser Asn Phe Thr Trp Thr Gly Ala Ser Lys Tyr Asn Leu
                500                 505                 510

Asn Gly Arg Glu Ser Ile Ile Asn Pro Gly Thr Ala Met Ala Ser His
            515                 520                 525

Lys Asp Asp Lys Asp Lys Phe Phe Pro Met Ser Gly Val Met Ile Phe
530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575

Arg Phe Gly Thr Val Ala Val Asn Leu Gln Ser Ser Ser Thr Asp Pro
            580                 585                 590

Ala Thr Gly Asp Val His Val Met Gly Ala Leu Pro Gly Met Val Trp
        595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Val Gln Tyr Thr Ser
690                 695                 700

Asn Tyr Ala Lys Ser Ala Asn Val Asp Phe Thr Val Asp Asn Asn Gly
705                 710                 715                 720

Leu Tyr Thr Glu Pro Arg Pro Ile Gly Thr Arg Tyr Leu Thr Arg Pro
                725                 730                 735
```

Leu

<210> SEQ ID NO 4
<211> LENGTH: 2214
<212> TYPE: DNA
<213> ORGANISM: Artificial Sequence
<220> FEATURE:
<223> OTHER INFORMATION: Synthetic Construct

<400> SEQUENCE: 4

```
atggctgccg atggttatct tccagattgg ctcgaggaca acctctctga gggcattcgc      60
gagtggtggg cgctgaaacc tggagccccg aagcccaaag ccaaccagca aaagcaggac     120
gacggccggg gtctggtgct tcctggctac aagtacctcg acccttcaa cggactcgac      180
aaggggagc ccgtcaacgc ggcggacgca gcggccctgg agcacgacaa ggcctacgac     240
cagcagctgc aggcgggtga caatccgtac ctgcggtata accacgccga cgccgagttt     300
caggagcgtc tgcaagaaga tacgtctttt ggggcaacc tcgggcgagc agtcttccag      360
gccaagaagc gggttctcga acctctcggt ctggttgagg aaggcgctaa gacggctcct     420
ggaaagaaga gaccggtaga gccatcaccc cagcgttctc cagactcctc tacgggcatc     480
ggcaagaaag ccaacagcc cgccagaaaa agactcaatt ttggtcagac tggcgactca     540
gagtcagttc cagaccctca acctctcgga gaacctccag cagcgccctc tggtgtggga     600
cctaatacaa tggcttcagg cggtggcgca ccaatggcag acaataacga aggcgccgac     660
ggagtgggta tgcctcagg aaattggcat gcgattcca catggctggg cgacagagtc      720
atcaccacca gcacccgaac atgggccttg cccacctata caaccaccct ctacaagcaa     780
atctccagtg cttcaacggg ggccagcaac gacaaccact acttcggcta cagcaccccc     840
tgggggtatt ttgatttcaa cagattccac tgccatttct caccacgtga ctggcagcga     900
ctcatcaaca caattggggg attccggccc aagagactca acttcaagct cttcaacatc     960
caagtcaagg aggtcacgac gaatgatggc gtcacgacca cgctaataa ccttaccagc    1020
acggttcaag tcttctcgga ctcggagtac cagttgccgt acgtcctcgg ctctgcgcac    1080
cagggctgcc tccctccgtt cccggcgac gtgttcatga ttccgcaata cggctacctg    1140
acgctcaaca atggcagcca agccgtggga cgttcatcct tttactgcct ggaatatttc    1200
ccttctcaga tgctgagaac gggcaacaac tttaccttca gctacacctt tgaggaagtg    1260
ccttttccaca gcagctacgc gcacagccag agcctggacc ggctgatgaa tcctctcatc    1320
gaccagtacc tgtattacct gaacagaact cagaatcagt ccggaagtgc ccaaaacaag    1380
gacttgctgt ttagccgtgg gtctccagct ggcatgtctg ttcagcccaa aaactggcta    1440
cctggaccct gttaccggca gcagcgcgtt tctaaaacaa aaacagacaa caacaacagc    1500
aactttacct ggactggtgc ttcaaaatat aacctcaatg ggcgtgaatc catcatcaac    1560
cctggcactg ctatggcctc acacaaagac gacaaagaca gttctttcc catgagcggt    1620
gtcatgattt ttggaaagga gagcgccgga gcttcaaaca ctgcattgga caatgtcatg    1680
atcacagacg aagaggaaat caaagccact aaccccgtgg ccaccgaaag atttgggact    1740
gtggcagtca atcccagag cagcagcaca gaccctgcga ccgagatgt gcatgttatg    1800
ggagccttac ctgaatggt gtggcaagac agagacgtat acctgcaggg tcctatttgg    1860
gccaaaattc ctcacacgga tggacacttt caccgtctc ctctcatggg cggctttgga    1920
cttaagcacc cgcctcctca gatcctcatc aaaaacacgc tgttcctgc gaatcctccg    1980
gcagagtttt cggctacaaa gtttgcttca ttcatcaccc agtattccac aggacaagtg    2040
```

```
agcgtggaga ttgaatggga gctgcagaaa gaaaacagca aacgctggaa tcccgaagtg    2100
cagtatacat ctaactatgc aaaatctgcc aacgttgatt ttactgtgga caacaatgga    2160
ctttatactg agcctcgccc cattggcacc cgttacctca cccgtcccct gtaa          2214

<210> SEQ ID NO 5

<400> SEQUENCE: 5

000

<210> SEQ ID NO 6
<211> LENGTH: 2214
<212> TYPE: DNA
<213> ORGANISM: Artificial Sequence
<220> FEATURE:
<223> OTHER INFORMATION: Synthetic Construct

<400> SEQUENCE: 6
atggctgccg atggttatct tccagattgg ctcgaggaca acctctctga gggcattcgc      60
gagtggtggg cgctgaaacc tggagccccg aagcccaaag ccaaccagca aaagcaggac    120
gacggccggg tctggtgct tcctggctac aagtacctcg acccttcaa cggactcgac      180 aaggggagc ccgtcaacgc ggcggacgca gcggccctcg agcacgacaa ggcctacgac     240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggcttcagg cggtggcgca ccaatggcag acaataacga aggcgccgac    660
ggagtgggta atgcctcagg aaattggcat tgcgattcca catggctggg cgacagagtc    720
atcaccacca gcacccgaac atgggccttg cccacctata acaaccacct ctacaagcaa    780
atctccagtg cttcaacggg ggccagcaac gacaaccact acttcggcta cagcaccccc    840
tgggggtatt ttgatttcaa cagattccac tgccatttct caccacgtga ctggcagcga    900
ctcatcaaca caatggggg attccggccc aagagactca acttcaagct cttcaacatc    960
caagtcaagg aggtcacgac gaatgatggc gtcacgacca cgctaataa ccttaccagc   1020 acggttcaag tcttctcgga ctcggagtac cagttgccgt acgtcctcgg ctctgcgcac   1080
cagggctgcc tccctccgtt cccggcggac gtgttcatga ttccgcaata cggctacctg   1140
acgctcaaca atggcagcca agcgtgggga cgttcatcct tttactgcct ggaatatttc   1200
ccttctcaga tgctgagaac gggcaacaac tttaccttca gctacacctt tgaggaagtg   1260
cctttccaca gcagctacgc gcacagccag agcctggacc ggctgatgaa tcctctcatc   1320
gaccagtacc tgtattacct gaacagaact cagaatcagt ccggaagtgc caaaacaag   1380 gacttgctgt ttagccgtgg gtctccagct ggcatgtctg ttcagccaa aaactggcta   1440 cctggaccct gttaccggca gcagcgcgtt tctaaaacaa aaacagacaa caacaacagc   1500
aactttacct ggactggtgc ttcaaaatat aacctcaatg ggcgtgaatc catcatcaac   1560
cctggcactg ctatggcctc acacaaagac gacaaagaca gttcttttcc catgagcggt   1620
gtcatgattt ttggaaagga gagcgccgga gcttcaaaca ctgcattgga caatgtcatg   1680
```

-continued

```
atcacagacg aagaggaaat caaagccact aacccgtgg ccaccgaaag atttgggact    1740
gtggcagtca atctccagag cagcagcaca gaccctgcga ccggagatgt gcatgttatg    1800
ggagccttac ctggaatggt gtggcaagac agagacgtat acctgcaggg tcctatttgg    1860
gccaaaattc ctcacacgga tggacacttt cacccgtctc ctctcatggg cggctttgga    1920
cttaagcacc cgcctcctca gatcctcatc aaaaacacgc ctgttcctgc gaatcctccg    1980
gcagagtttt cggctacaaa gtttgcttca ttcatcaccc agtattccac aggacaagtg    2040
agcgtggaga ttgaatggga gctgcagaaa gaaaacagca aacgctggaa tcccgaagtg    2100
cagtatacat ctaactatgc aaaatctgcc aacgttgatt ttactgtgga caacaatgga    2160
ctttatactg agcctcgccc cattggcacc cgttacctca cccgtcccct gtaa           2214
```

<210> SEQ ID NO 7
<211> LENGTH: 204
<212> TYPE: DNA
<213> ORGANISM: Artificial Sequence
<220> FEATURE:
<223> OTHER INFORMATION: Synthetic Construct

<400> SEQUENCE: 7

```
gcgagaactt gtgcctcccc gtgttcctga cctttgaccc tctgtcctac ttagactaat     60
attgactttg ggtactgcaa acaggaaatg ggggagggat tcgatgcgag aacttgtgcc    120
tccccgtgtt cctgaccttt gaccctctgt cctacttaga ctaatattga ctttgggtac    180
tgcaaacagg aaatggggga ggga                                           204
```

<210> SEQ ID NO 8
<211> LENGTH: 330
<212> TYPE: DNA
<213> ORGANISM: Artificial Sequence
<220> FEATURE:
<223> OTHER INFORMATION: Synthetic Construct

<400> SEQUENCE: 8

```
ggccccaggt taattttta aaaagcagtca aaggtcaaag tggcccttgg cagcatttac     60
tctctctatt gactttggtt aataatctca ggagcacaaa cattcctgga ggcaggagaa    120
gaaatcaaca tcctggactt atcctctggg cctctcccca ccttcgatgg ccccaggtta    180 attttaaaa agcagtcaaa ggtcaaagtg gcccttggca gcatttactc tctctattga    240
ctttggttaa taatctcagg agcacaaaca ttcctggagg caggagaaga atcaacatc    300 ctggacttat cctctgggcc tctccccacc                                     330
```

<210> SEQ ID NO 9
<211> LENGTH: 377
<212> TYPE: DNA
<213> ORGANISM: Artificial Sequence
<220> FEATURE:
<223> OTHER INFORMATION: Synthetic Construct

<400> SEQUENCE: 9

```
gttcctagat tacattacac attctgcaag catagcacag gtcaaagttc aactttaatt     60
actttcattt tcttgtatcc tcacagccta gaaaataacc tgcgttacag catccactca    120
gtatcccttg agcatgaggt gacactactt aacatagggA cgagatggta ctttgtgtct    180
cctgctctgt cagcagggca ctgtacttgc tgataccagg gaatattgat ttgtaaatac    240
catcattccg aacgtgtttg ccttggccag ttttccatgt acatgcagaa agaagtttgg    300
```

```
gactgatcaa tacagtcctc tgcctttaaa gcaataggaa aaggccaact tgtctacgtt    360
tagtatgtgg ctgtaga                                                  377

<210> SEQ ID NO 10
<211> LENGTH: 156
<212> TYPE: DNA
<213> ORGANISM: Artificial Sequence
<220> FEATURE:
<223> OTHER INFORMATION: Synthetic Construct

<400> SEQUENCE: 10
ccatcagatc ctgcccaagg tcttacataa gaggactctt ggactcccag caatgtcaac     60
gaccgacctt gaggcctact tcaaagactg tgtgtttaag gactgggagg agctgggga    120 ggagattagg ttaaaggtct tgtattagg aggctg                              156

<210> SEQ ID NO 11
<211> LENGTH: 71
<212> TYPE: DNA
<213> ORGANISM: Artificial Sequence
<220> FEATURE:
<223> OTHER INFORMATION: Synthetic Construct

<400> SEQUENCE: 11
ggggaggctg ctggtgaata ttaaccaagg tcaccccagt tatcggagga gcaaacaggg     60
gctaagtcca c                                                         71

<210> SEQ ID NO 12
<211> LENGTH: 869
<212> TYPE: DNA
<213> ORGANISM: Artificial Sequence
<220> FEATURE:
<223> OTHER INFORMATION: Synthetic Construct

<400> SEQUENCE: 12
ctcaattgga tgacactagt catcacattt aaaagcatct caggtaacta tattttgaat     60
ttttttaaaa agtaactata atagttatta ttaaaatagc aaagattgac catttccaag    120
agccatatag accagcaccg accactattc taaactattt atgtatgtaa atattagctt    180
ttaaaattct caaaatagtt gctgagttgg gaaccactat tatttctatc gattcagcag    240
ccgtaagtct aggacaggct taaattgttt tcactggtgt aaattgcaga agatgatct    300 aagtaatttg gcatttattt taataggttt gaaaaacaca tgccatttta caaataagac    360
ttatatttgt cctttttgttt ttcagcctac catgagaata agagaaagaa atgaagatc    420 aaaagcttat tcatctgttt ttcttttttcg ttggtgtaaa gccaacaccc tgtctaaaaa    480
acataaattt ctttaatcat tttgcctctt ttctctgtgc ttcaattaat aaaaaatgga    540
aagaatctaa tagagtggta cagcactgtt atttttcaaa gatgtgttgc tatcctgaaa    600
attctgtagg ttctgtggaa gttccagtgt tctctcttat tccacttcgg tagaggattt    660
ctagtttctt gtgggctaat taaataaatc attaatactc ttctaagtta tggattataa    720
acattcaaaa taatatttg acattatgat aattctgaat aaaagaacaa aaaccatggt    780
ataggtaagg aatataaaac atggcttta ccttagaaaa aacaattcta aaattcatat    840
ggaatcaaaa aagagcctgc aggtaccct                                      869

<210> SEQ ID NO 13
<211> LENGTH: 1302
<212> TYPE: DNA
<213> ORGANISM: Artificial Sequence
```

```
<220> FEATURE:
<223> OTHER INFORMATION: Synthetic Construct

<400> SEQUENCE: 13
ctcaattgga tgacactagt catcacattt aaaagcatct caggtaacta tattttgaat       60
ttttaaaaa agtaactata atagttatta ttaaaatagc aaagattgac catttccaag       120
agccatatag accagcaccg accactattc taaactattt atgtatgtaa atattagctt     180
ttaaaattct caaatagtt gctgagttgg gaaccactat tatttctatc tactgtttta      240
attaaaatta tctctaaggc atgtgaactg gctgtcttgg ttttcatctg tacttcatct     300
gctacctctg tgacctgaaa catatttata attccattaa gctgtgcata tgatagattt     360
atcatatgta ttttccttaa aggattttg taagaactaa ttgaattgat acctgtaaag      420
tctttatcac actacccaat aaataataaa tctctttgtt cagctctctg tttctataaa     480
tatgtaccag ttttattgtt tttagtggta gtgatttat tctctttcta tatatataca      540
cacacatgtg tgcattcata aatatataca attttatga ataaaaatt attagcaatc       600
aatattgaaa accactgatt tttgtttatg tgagcaaaca gcagattaaa aggaattcct     660
gcagattcag cagccgtaag tctaggacag gcttaaattg ttttcactgg tgtaaattgc     720
agaaagatga tctaagtaat ttggcattta ttttaatagg tttgaaaaac acatgccatt    780
ttacaaataa gacttatatt tgtccttttg ttttcagcc taccatgaga ataagagaaa      840
gaaaatgaag atcaaaagct tattcatctg tttttctttt tcgttggtgt aaagccaaca    900
ccctgtctaa aaaacataaa tttctttaat cattttgcct cttttctctg tgcttcaatt    960
aataaaaaat ggaaagaatc taatagagtg gtacagcact gttattttttc aaagatgtgt    1020
tgctatcctg aaaattctgt aggttctgtg gaagttccag tgttctctct tattccactt    1080
cggtagagga tttctagttt cttgtgggct aattaaataa atcattaata ctcttctaag    1140
ttatggatta taaacattca aaataatatt ttgacattat gataattctg aataaaagaa    1200
caaaaaccat ggtataggta aggaatataa aacatggctt ttaccttaga aaaaacaatt    1260
ctaaaattca tatggaatca aaaaagagcc tgcaggtacc ct                       1302

<210> SEQ ID NO 14
<211> LENGTH: 4567
<212> TYPE: DNA
<213> ORGANISM: Artificial Sequence
<220> FEATURE:
<223> OTHER INFORMATION: Synthetic Construct

<400> SEQUENCE: 14
ttggccactc cctctctgcg cgctcgctcg ctcactgagg ccgcccgggc aaagcccggg       60
cgtcgggcga cctttggtcg cccggcctca gtgagcgagc gagcgcgcag agagggagtg      120
gccaactcca tcactagggg ttccttaccg cgtggcccca ggttaatttt taaaaagcag     180
tcaaaggtca aagtggccct tggcagcatt tactctctct attgactttg gttaataatc     240
tcaggagcac aaacattcct ggaggcagga gaagaaatca acatcctgga cttatcctct     300
gggcctctcc ccaccttcga tggccccagg ttaatttta aaaagcagtc aaaggtcaaa      360
gtggcccttg gcagcattta ctctctctat tgactttggt taataatctc aggagcacaa    420
acattcctgg aggcaggaga agaaatcaac atcctggact tatcctctgg gcctctcccc    480
accgatatct acctgctgat cgcccggccc ctgttcaaac atgtcctaat actctgtcgg    540
ggcaaaggtc ggcagtagtt ttccatctta ctcaacatcc tcccagtgta cgtaggatcc    600
```

-continued

```
tgtctgtctg cacatttcgt agagcgagtg ttccgatact ctaatctccc ggggcaaagg      660
tcgtattgac ttaggttact tattctcctt ttgttgacta agtcaataat cagaatcagc      720
aggtttggag tcagcttggc agggatcagc agcctgggtt ggaaggaggg ggtataaaag      780
ccccttcacc aggagaagcc gtcacacaga tccacaagct cctgctagcc aattgagtcg      840
ctgcgcgctg ccttcgcccc gtgccccgct ccgccgccgc ctcgcgccgc ccgccccggc      900
tctgactgac cgcgttactc ccacaggtga gcgggcggga cggcccttct cctccgggct      960
gtaattagcg cttggtttat tgacggcttg tttcttttct gtggctgcgt gaaagccttg     1020
aggggctccg ggaaggccct tgtgcgggg gagcggctc ggggggtgcg tgcgtgtgtg        1080
tgtgcgtggg gagcgccgcg tgcggctccg cgctgcccgg cggctgtgag cgctgcgggc     1140
gcggcgcggg gctttgtgcg ctccgcagtg tgcgcgaggg gagcggggcc ggggcggtg      1200
ccccgcggtg cgggggggc tgcgagggga acaaaggctg cgtgcggggt gtgtgcgtgg      1260
gggggtgagc aggggtgtg ggcgcgtcgg tcggctgca acccccctg caccccctc         1320
cccgagttgc tgagcacggc ccggcttcgg gtgcggggct ccgtacgggg cgtggcgcgg     1380
ggctcgccgt gccgggcggg gggtggcggc aggtgggggt gccgggcggg gcggggccgc     1440
ctcgggccgg ggagggctcg ggggaggggc gcggcggccc ccggagcgcc ggcggctgtc     1500
gaggcgcggc gagccgcagc cattgccttt tttggtaatc gtgcgagagg gcgcagggac     1560
ttcctttgtc ccaaatctgt gcggagccga atctgggag gcgccgccgc accccctcta     1620
gcgggcgcgg ggcgaagcgg tgcggcgccg gcaggaagga attgggcggg gagggccttc     1680
gtgcgtcgcc gcgccgccgt ccccttctcc ctctccagcc tcggggctgt ccgcgggggg     1740
acggctgcct tcgggggga cggggcaggg cggggttcgg cttctggcgt gtgaccggcg     1800
gctctagagc ctctgctaac cttgttcttg ccttcttctt tttcctacag ctcctgggca     1860
acgtgctggt tattgtgctg tctcatcatt ttggcaaaga attcatttcg aagccgccac     1920
catgagcaca gccgtgctgg aaaaccccgg cctgggcaga aagctgagcg acttcggcca     1980
ggaaaccagc tacatcgagg acaactgcaa ccagaacggc gccatcagcc tgatcttcag     2040
cctgaaagaa gaagtgggcg ccctggccaa ggtgctgcgg ctgttcgagg agaacgacgt     2100
gaacctgacc cacatcgaga gccggcccag cagactgaag aaggacgagt acgagttctt     2160
cacccacctg gacaagcgga gcctgcccgc cctgaccaac atcatcaaga tcctgcggca     2220
cgacatcggc gccaccgtgc acgagctgag ccgggacaag aaaaaggaca ccgtgccctg     2280
gttccccaga accatccagg aactggacag attcgccaac cagatcctgt cctacggcgc     2340
cgagctggat gccgaccacc ctggcttcaa ggaccccgtg taccgggcca gacggaagca     2400
gttcgccgat atcgcctaca actaccggca cggccagccc atcccagag tcgagtacat     2460
ggaagaggag aagaaaacct ggggcaccgt gttcaagacc ctgaagtccc tgtacaagac     2520
ccacgcctgc tacgagtaca accacatctt cccactgctc gaaaagtact gcggcttcca     2580
cgaggacaat atccctcagc tggaggacgt gtcccagttt ctgcagacct gcaccggctt     2640
cagactcagg cctgtggccg gcctgctgag cagcagagat tttctgggcg gactggcctt     2700
ccgggtgttc cactgcaccc agtacatcag acacggcagc aagcccatgt acacccctga     2760
gcccgacatc tgccacgagc tgctgggaca tgtgcccctg ttcagcgaca gaagcttcgc     2820
ccagttcagc caggaaatcg gcctggcctc tctgggcgct cccgacgagt atatcgagaa     2880
gctggccacc atctactggt tcaccgtgga attcggcctg tgcaagcagg gcgacagcat     2940
caaggcctat ggcgccggac tcctgtccag cttcggcgag ctgcagtact gtctgagcga     3000
```

```
gaagcccaag ctgctgcccc tggaactgga aaagaccgcc atccagaact acaccgtgac    3060
cgagttccag cccctgtact acgtggccga gagcttcaac gacgccaaag aaaaagtgcg    3120
gaacttcgcc gccaccatcc ctcggcccct cagcgtcaga tacgacccct acacccagcg    3180
gatcgaggtg ctggacaaca cacagcagct gaaaattctg ccgactcca tcaacagcga     3240 gatcggcatc ctgtgcagcg ccctgcagaa aatcaagtga actagtctgt gccttctagt    3300
tgccagccat ctgttgtttg cccctccccc gtgccttcct tgaccctgga aggtgccact    3360
cccactgtcc tttcctaata aaatgaggaa attgcatcgc attgtctgag taggtgtcat    3420
tctattctgg ggggtggggt ggggcaggac agcaagggg  aggattggga agacaatagc    3480
aggcatgctg gggatgcggt gggctctatg gtaccaccgg tccagggggtg agtgaaggtt   3540 tggaagagtg tagcagaata agaaaccatg agtcccctcc ctgagaagcc ctgagccccc    3600
ttgacgacac acatccctcg aggctcagct tcatcatctg taaaaggtgc tgaaactgac    3660
catccaagct gccgaaaaag attgtgtggg gataattcaa aactagagga agatgcagaa    3720
tttctacatc gtggcgatgt caggctaaga gttgccatcg tggctgtcca tcgattttat    3780
tggaatcata tgtttatttg agggtgtctt ggatattaca aataaattgt tggagcatca    3840
ggcatatttg gtaattctgt ctaaggctcc ctgcccctng ttaattggca gctcagttat    3900
tcatccaggg caaacattct gcttactatt cctgagagct ttcctcatcc tctagattgg    3960
caggggaatt gcagttgcct gagcagcctc ccctctgcca taccaacaga gcttcaccat    4020
cgaggcttgc agagtggaca ggggcctcag ggacccctga tcccagcttt ctcattggac    4080
agaaggagga gactggggct ggagagggac ctgggccccc actaaggcca cagcagagcc    4140
aggactttag ctgtgctgac tgcagcctgg cttgcctcca ctgccctcct ttgcctcaag    4200
agcaagggag cctcagagtg gaggaagcag cccctggcct tgcctcccac ctcccctccc    4260
ctttgctgtt ttcctgggac agtgggagct ggcttagatt gccctggggc cccaggaacc   4320
ctggcatttt aaccccctcag gggcaggaag gcagcctgag atacagaaga gtccatcacc    4380
tgctgtatgc cacacaccat ccccacagtc gacatttaaa ttaggaaccc ctagtgatgg    4440
agttggccac tccctctctg cgcgctcgct cgctcactga ggccgcccgg gcaaagcccg    4500
ggcgtcgggc gacctttggt cgcccggcct cagtgagcga gcgagcgcgc agagagggag    4560
tggccaa                                                              4567
```

<210> SEQ ID NO 15  
<211> LENGTH: 1069  
<212> TYPE: DNA  
<213> ORGANISM: Artificial Sequence  
<220> FEATURE:  
<223> OTHER INFORMATION: Synthetic Construct

<400> SEQUENCE: 15

```
agtcgctgcg cgctgccttc gccccgtgcc ccgctccgcc gccgcctcgc gccgccgcc      60 ccggctctga ctgaccgcgt tactcccaca ggtgagcggg cgggacggcc cttctcctcc    120
gggctgtaat tagcgcttgg tttattgacg gcttgtttct tttctgtggc tgcgtgaaag    180
ccttgagggg ctccgggaag gcccctttgtg cggggggagc ggctcggggg gtgcgtgcgt   240
gtgtgtgtgc gtggggagcg ccgcgtgcgg ctccgcgctg cccggcggct gtgagcgctg    300
cgggcgcggc gcggggcttt gtgcgctccg cagtgtgcgc gaggggagcg gggcggggg     360 cggtgccccg cggtgcgggg ggggctgcga ggggaacaaa ggctgcgtgc ggggtgtgtg    420
```

```
cgtgggggg  tgagcagggg  gtgtgggcgc  gtcggtcggg  ctgcaacccc  ccctgcaccc      480
ccctccccga  gttgctgagc  acggcccggc  ttcgggtgcg  ggctccgta   cggggcgtgg     540 cgcggggctc  gccgtgccgg  gcgggggtg   gcggcaggtg  ggggtgccgg  gcggggcggg     600
gccgcctcgg  gccggggagg  gctcgggga   ggggcgcggc  ggccccgga   gcgccggcgg     660 ctgtcgaggc  gcggcgagcc  gcagccattg  ccttttttgg  taatcgtgcg  agagggcgca     720
gggacttcct  ttgtcccaaa  tctgtgcgga  gccgaaatct  gggaggcgcc  gccgcacccc    780
ctctagcggg  cgcggggcga  agcggtgcgg  cgccggcagg  aaggaattgg  gcgggagggg    840
ccttcgtgcg  tcgccgcgcc  gccgtcccct  tctccctctc  cagcctcggg  gctgtccgcg     900
gggggacggc  tgccttcggg  ggggacgggg  cagggcgggg  ttcggcttct  ggcgtgtgac     960
cggcggctct  agagcctctg  ctaaccttgt  tcttgcctc   ttcttttcc   tacagctcct   1020 gggcaacgtg  ctggttattg  tgctgtctca  tcattttggc  aaagaattc                1069

<210> SEQ ID NO 16
<211> LENGTH: 901
<212> TYPE: DNA
<213> ORGANISM: Artificial Sequence
<220> FEATURE:
<223> OTHER INFORMATION: Synthetic Construct

<400> SEQUENCE: 16 ccagggtga   gtgaaggttt  ggaagagtgt  agcagaataa  gaaaccatga  gtcccctccc    60
tgagaagccc  tgagcccct   tgacgacaca  catccctcga  ggctcagctt  catcatctgt   120
aaaaggtgct  gaaactgacc  atccaagctg  ccgaaaaaga  ttgtgtgggg  ataattcaaa   180
actagaggaa  gatgcagaat  ttctacatcg  tggcgatgtc  aggctaagag  ttgccatcgt   240
ggctgtccat  cgatttttatt ggaatcatat  gtttatttga  gggtgtcttg  gatattacaa   300
ataaattgtt  ggagcatcag  gcatatttgg  taattctgtc  taaggctccc  tgccccttgt   360 taattgcag   ctcagttatt  catccagggc  aaacattctg  cttactattc  ctgagagctt   420
tcctcatcct  ctagattggc  aggggaattg  cagttgcctg  agcagcctcc  cctctgccat    480
accaacagag  cttcaccatc  gaggcttgca  gagtggacag  gggcctcagg  gacccctgat   540
cccagctttc  tcattggaca  gaaggaggag  actggggctg  gagagggacc  tgggccccca   600
ctaaggccac  agcagagcca  ggactttagc  tgtgctgact  gcagcctggc  ttgcctccac    660
tgccctcctt  tgcctcaaga  gcaagggagc  ctcagagtgg  aggaagcagc  ccctggcctt    720
gcctcccacc  tcccctcccc  tttgctgttt  tcctgggaca  gtgggagctg  gcttagattg    780
ccctggggcc  cccaggaccc  tggcatttta  acccctcagg  ggcaggaagg  cagcctgaga    840
tacagaagag  tccatcacct  gctgtatgcc  acacaccatc  cccacagtcg  acatttaaat    900
t                                                                        901

<210> SEQ ID NO 17
<211> LENGTH: 78
<212> TYPE: DNA
<213> ORGANISM: Artificial Sequence
<220> FEATURE:
<223> OTHER INFORMATION: Synthetic Construct

<400> SEQUENCE: 17
cactccctct  ctgcgcgctc  gctcgctcac  tgaggccggg  cgaccaaagg  tcgcccacgc     60
ccgggctttg  cccgggcg                                                       78
```